US006458433B1

(12) United States Patent
Kato et al.

(10) Patent No.: US 6,458,433 B1
(45) **Date of Patent: *Oct. 1, 2002**

(54) DIFLUOROPHENYL DERIVATIVES, LIQUID-CRYSTAL COMPOUNDS, AND LIQUID-CRYSTAL COMPOSITION

(75) Inventors: Takashi Kato, Chiba (JP); Shuichi Matsui, Chiba (JP); Kazutoshi Miyazawa, Chiba (JP); Fusayuki Takeshita, Chiba (JP); Etsuo Nakagawa, Chiba (JP)

(73) Assignee: Chisso Corporation, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/331,058

(22) PCT Filed: Dec. 16, 1997

(86) PCT No.: PCT/JP97/04633

§ 371 (c)(1), (2), (4) Date: Jun. 16, 1999

(87) PCT Pub. No.: WO98/27036

PCT Pub. Date: Jun. 25, 1998

(30) Foreign Application Priority Data

Dec. 16, 1996 (JP) .......................................... 8-353203

(51) Int. Cl.$^7$ ...................... C09K 19/34; C09K 19/30; C07C 25/13; C07C 25/18; C07D 239/02; C07D 319/06

(52) U.S. Cl. ............. 428/1.1; 252/299.61; 252/299.63; 252/299.66; 544/242; 544/298; 544/335; 546/192; 546/251; 549/13; 549/369; 549/428; 570/127; 570/129; 570/131

(58) Field of Search ...................... 252/299.61, 299.63, 252/299.66; 428/1.1; 544/242, 298, 335; 546/192, 251; 549/13, 369, 428; 570/127, 129, 131

(56) References Cited

U.S. PATENT DOCUMENTS

| | | | | |
|---|---|---|---|---|
| 4,627,933 A | | 12/1986 | Eidenschink et al. .... | 252/299.6 |
| 5,232,624 A | * | 8/1993 | Reiffenrath et al. .... | 252/299.61 |
| 5,346,647 A | * | 9/1994 | Kelly et al. ............ | 252/299.63 |
| 5,468,421 A | * | 11/1995 | Matsui et al. .......... | 252/299.63 |

FOREIGN PATENT DOCUMENTS

| | | |
|---|---|---|
| EP | 0410233 | 1/1991 |
| JP | 57-114532 | 7/1982 |
| JP | 2-503435 | 10/1990 |
| JP | 2-503441 | 10/1990 |
| JP | 3-66632 | 3/1991 |
| JP | 5-229980 | 9/1993 |
| JP | 6-157371 | 6/1994 |
| JP | 8-40953 | 2/1996 |

OTHER PUBLICATIONS

Kelly, "The Synthesis and Liquid Crystal Transition Temperatures of a Broad Range of Mesogens Incorporating Four–Unit–Linking Groups I", Mol. Cryst. Liq. Cryst., 1991, vol. 204, pp. 27–35.

Kelly, "Four unit linking groups III. Liquid crystals of negative dielectric anisotropy", Liquid Crystals, 1991, vol. 10, No. 2, 261–272.

* cited by examiner

*Primary Examiner*—Shean C. Wu
(74) *Attorney, Agent, or Firm*—Wenderoth, Lind & Ponack, L.L.P.

(57) ABSTRACT

Disclosed are liquid crystalline compounds which (i) are characterized in that the compounds have a wide temperature range in which the compounds exhibit a liquid crystal phase, are low in viscosity, and have a negative and large $\Delta\epsilon$, (ii) are readily mixed with other various liquid crystal materials even at low temperatures, and (iii) are useful as component of liquid crystal compositions suitable both for TFT type display mode and IPS mode; and liquid crystal composition comprising the liquid crystalline compound; the compounds are expressed by the general formula (1)

(1)

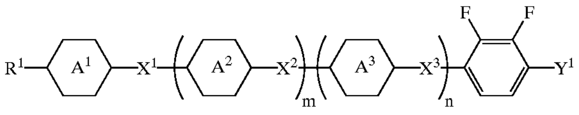

wherein $R^1$ represents an alkyl group having 1 to 15 carbon atoms; ring $A^1$, ring $A^2$, and ring $A^3$ independently represent trans-1,4-cyclohexylene group, trans-1,4-silacyclohexylene group, pyrimidine-2,5-diyl group, pyridine-2,5-diyl group, 1,3-dioxane-2,5-diyl group, tetrahydropyran-2,5-diyl group, 1,3-dithian-2,5-diyl group, or tetrahydrothiopyran-2,5-diyl group, or 1,4-phenylene group in which one or more hydrogen atoms on the six-membered ring may be replaced by a halogen atom; $X^1$, $X^2$, and $X^3$ independently represent $-(CH_2)_4-$, $-(CH_2)_3O-$, $-O(CH_2)_3-$, or single bond; $Y^1$ represents hydrogen atom or an alkyl group having 1 to 15 carbon atoms; m and n are independently 0 or 1; and any atom which constitutes this compound may be replaced by its isotope.

18 Claims, No Drawings

DIFFLUOROPHENYL DERIVATIVES, LIQUID-CRYSTAL COMPOUNDS, AND LIQUID-CRYSTAL COMPOSITION

This application is a 371 application of International Application No. PCT/JP97/04633 filed Dec. 16, 1997.

TECHNICAL FIELD

The present invention relates to liquid crystalline compounds and liquid crystal compositions. More specifically, the invention relates to novel liquid crystalline compounds simultaneously having butylene group or propylenoxy group, and 2,3-difluorophenyl group in the compounds; to liquid crystal compositions comprising the compound; and further to liquid crystal display devices fabricated by using the liquid crystal composition.

BACKGROUND ART

Display devices produced by employing optical anisotropy and dielectric anisotropy which are characteristics of liquid crystalline compounds (the term "liquid crystalline compounds" is used in this specification as a general term for the compounds which exhibit a liquid crystal phase and for the compounds which do not exhibit a liquid crystal phase but are useful as component of liquid crystal compositions) have widely been utilized for tabletop calculators, word processors, and TV sets including watches, and the demand for the devices are rising year after year.

Liquid crystal phase is broadly classified into nematic phase, smectic phase, and cholesteric phase. Among them, nematic phase has most widely been employed for display devices. As display mode applied for liquid crystal display, TN (twisted nematic) display mode, DS (dynamic scattering) display mode, guest-host display mode, and DAP (Deformation of Aligned Phases) display mode have been developed corresponding to electro-optic effects.

In recent years, coloring of liquid crystal displays has rapidly been advanced, and thin film transistor (TFT) display mode and super twisted nematic (STN) display mode are main streams in TN display mode as display mode. On the other hand, CRT which is a main stream of current television screen is expected to be replaced by liquid crystal displays sooner or later. In order to realize the replacement, liquid crystal displays must have display characteristics comparable to those of CRT.

In the research and development of liquid crystal displays, one's energies have been devoted to the improvement of response speed, contrast, and viewing angle as important subject. Among them, response speed and contrast became such an extent as equal to those of CRT as a result of repeated improvements in TFT display mode. However, a wide viewing angle comparable to that of CRT has not yet been actualized, whereas some improvements such as an improvement in the orientational direction of liquid crystal molecules and the use of a phase difference plate have been made as to viewing angle.

Although it is an active matrix mode similar to that of TFT display mode, in-plane-switching (IPS) display mode which is characterized in that comb type electrodes are formed only one side of substrate is lately performed on the stage as a mode for actualizing a wide viewing angle (G. Baur, Freiburger Arbeistagung Flussigkristalle, Abstract No. 22 (1993) and M. Oh-e et al., ASIA DISPLAY '95, 577 (1995)). When liquid crystalline compounds having a negative dielectric anisotropy value (Δε) was used in IPS display mode, a dramatically wide viewing angle was obtained.

However, this IPS display mode has such a defect that response speed is considerably low compared with conventional TFT display mode or STN display mode. Then, liquid crystalline compounds having a negative and large Δε and a low viscosity have been required in IPS display mode.

Also, since active matrix driving mode is employed in IPS mode as described above, liquid crystalline compounds having a high voltage holding ratio (V. H. R.) are more preferable.

Various compounds having a negative dielectric anisotropy value are already known. In Laid-open Japanese Patent Publication No. Hei 2-4724 and Tokuhyo (Laid-open Japanese WO publication) No. Hei 2-503441, compounds having 2,3-difluoro-1,4-phenylene group in their partial structure are disclosed as liquid crystal compound having a negative Δε.

It is considered that in the compounds having such partial structure, fluorine atoms substituted at positions 2 and 3 act so as to increase dipole moment in the direction of the minor axis of molecules to make dipole moment of the major axis smaller than the dipole moment in the direction of minor axis, and as the result, the compounds come to have a negative dielectric anisotropy value. However, compounds having such partial structure become slightly narrow in their temperature range exhibiting a liquid crystal phase compared with compounds in which hydrogen atoms of phenylene group are not replaced by fluorine atoms, their miscibility with other liquid crystalline compounds particularly at very low temperatures can hardly be said to be excellent, and sometimes such phenomena that smectic phase is developed and crystals are separated in liquid crystal compositions in a low temperature region are observed.

Compounds expressed by the following formula (a) are described in Tokuhyo No. Hei 2-503441:

(a)

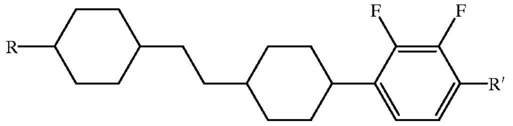

wherein R and R' represent an alkyl group and alkoxy group, respectively.

Whereas structural formula of the compounds is described in the publication mentioned above, physical properties and the likes necessary for judging the utility of the compounds as liquid crystalline compound are not described at all therein. Based on the consideration by the present inventors, whereas an improvement in miscibility by the compounds of the formula (a) described above compared with compounds having no 1,2-ethylene group can be surmised since the compounds of the formula (a) have 1,2-ethylene group as bonding group in skeleton structure, their effect can not be said to be sufficient.

DISCLOSURE OF THE INVENTION

An object of the present invention is to provide liquid crystalline compounds which are wide particularly in temperature range of liquid crystal phase, have a low viscosity, have a negative and large Δε, and are improved in solubility at low temperatures; to provide liquid crystal compositions comprising the compound; and to provide liquid crystal display devices fabricated by using the liquid crystal composition, thereby to overcome the problems in conventional technologies described above.

Then, compounds expressed by the general formula (1) and simultaneously having butylene group or propylenoxy group, and 2,3-difluoro-1,4-phenylene group in the structure of compounds were diligently investigated by the present inventors. As the result of the investigation, it has been found out that the compounds are characterized in that they are wide in temperature range exhibiting a liquid crystal phase, are low in viscosity, and have a negative and large Δ∈, as well as they are remarkably excellent in miscibility at low temperatures, leading to the accomplishment of the present invention.

That is, the present invention is summarized as follows:

[1] A liquid crystalline compound expressed by the general formula (1)

(1)

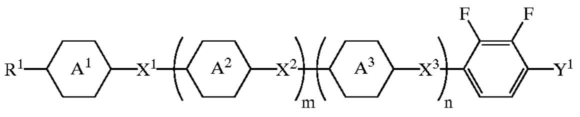

wherein $R^1$ represents an alkyl group having 1 to 15 carbon atoms in which alkyl group, not-adjacent any methylene group may be replaced by oxygen atom or vinylene group, and any hydrogen atom in the alkyl group may be replaced by fluorine atom; ring $A^1$, ring $A^2$, and ring $A^3$ independently represent trans-1,4-cyclohexylene group, trans-1,4-silacyclohexylene group, pyrimidine-2,5-diyl group, pyridine-2,5-diyl group, 1,3-dioxane-2,5-diyl group, tetrahydropyran-2,5-diyl group, 1,3-dithian-2,5-diyl group, or tetrahydrothiopyran-2,5-diyl group, or 1,4-phenylene group in which one or more hydrogen atoms on the six-membered ring may be replaced by a halogen atom; $X^1$, $X^2$, and $X^3$ independently represent $-(CH_2)_4-$, $-(CH_2)_3O-$, $-O(CH_2)_3-$, or single bond; $Y^1$ represents hydrogen atom or an alkyl group having 1 to 15 carbon atoms in which alkyl group not-adjacent any methylene group may be replaced by oxygen atom or vinylene group; m and n are independently 0 or 1; and any atom which constitutes this compound may be replaced by its isotope.

[2] The liquid crystalline compound recited in paragraph [1] above wherein ring $A^1$ represents trans-1,4-cyclohexylene group, or 1,4-phenylene group in which one or more hydrogen atoms on the six-membered ring may be replaced by fluorine atom; $X^1$ represents $-(CH_2)_4-$ or $-(CH_2)_3O-$; and either m and n are 0 in the general formula (1).

[3] The liquid crystalline compound recited in paragraph [1] above wherein ring $A^1$and ring $A^2$ independently represent trans-1,4-cyclohexylene group, or 1,4-phenylene group in which one or more hydrogen atoms on the six-membered ring may be replaced by fluorine atom; $X^1$ represents $-(CH_2)_4-$ or $-(CH_2)_3O-$; $X^2$ represents single bond; and m is 1 and n is 0 in the general formula (1).

[4] The liquid crystalline compound recited in paragraph [1] above wherein ring $A^1$ and ring $A^2$ independently represent trans-1,4-cyclohexylene group, or 1,4-phenylene group in which one or more hydrogen atoms on the six-membered ring may be replaced by fluorine atom; $X^2$ represents $-(CH_2)_4-$ or $-(CH_2)_3O-$; $X^1$ represents single bond; and m is 1 and n is 0 in the general formula (1).

[5] The liquid crystalline compound recited in paragraph [1] above wherein ring $A^1$, ring $A^2$, and ring $A^3$ independently represent trans-1,4-cyclohexylene group, or 1,4-phenylene group in which one or more hydrogen atoms on the six-membered ring may be replaced by fluorine atom; $X^1$ represent $-(CH_2)_4-$ or $-(CH_2)_3O-$; either $X^2$ and $X^3$ represent single bond; and m is 1 and n is 1 in the general formula (1).

[6] The liquid crystalline compound recited in paragraph [1] above wherein ring $A^1$, ring $A^2$, and ring $A^3$ independently represent trans-1,4-cyclohexylene group, or 1,4-phenylene group in which one or more hydrogen atoms on the six-membered ring may be replaced by fluorine atom; $X^2$ represents $-(CH_2)_4-$ or $-(CH_2)_3O-$; either $X^1$ and $X^3$ represent single bond; and m is 1 and n is 1 in the general formula (1).

[7] The liquid crystalline compound recited in paragraph [1] above wherein ring $A^1$, ring $A^2$, and ring $A^3$ independently represent trans-1,4-cyclohexylene group, or 1,4-phenylene group in which one or more hydrogen atoms on the six-membered ring may be replaced by fluorine atom; $X^3$ represents $-(CH_2)_4-$ or $-(CH_2)_3O-$; either $X^1$ and $X^2$ represent single bond; and m is 1 and n is 1 in the general formula (1).

[8] A liquid crystal composition comprising at least two components and comprising at least one liquid crystalline compound expressed by the general formula (1)

(1)

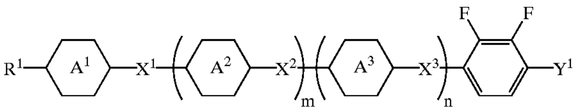

wherein $R^1$ represents an alkyl group having 1 to 15 carbon atoms in which alkyl group not-adjacent any methylene group may be replaced by oxygen atom or vinylene group, and any hydrogen atom in the alkyl group may be replaced by fluorine atom; ring $A^1$, ring $A^2$, and ring $A^3$ independently represent trans-1,4-cyclohexylene group, trans-1,4-silacyclohexylene group, pyrimidine-2,5-diyl group, pyridine-2,5-diyl group, 1,3-dioxane-2,5-diyl group, tetrahydropyran-2,5-diyl group, 1,3-dithian-2,5-diyl group, or tetrahydrothiopyran-2,5-diyl group, or 1,4-phenylene group in which one or more hydrogen atoms on the six-membered ring may be replaced by a halogen atom; $X^1$, $X^2$, and $X^3$ independently represent $-(CH_2)_4-$, $-(CH_2)_3O-$, $-O(CH_2)_3-$, or single bond; $Y^1$ represents hydrogen atom or an alkyl group having 1 to 15 carbon atoms in which alkyl group not-adjacent any methylene group may be replaced by oxygen atom or vinylene group; m and n are independently 0 or 1; and any atom which constitutes this compound may be replaced by its isotope.

[9] A liquid crystal composition comprising, as a first component, at least one liquid crystalline compound recited in any one of paragraphs [1] to [7] above, and comprising, as a second component, at least one compound selected from the group consisting of the compounds expressed by any one of the general formulas (2), (3), and (4)

(2)

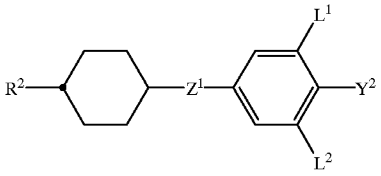

(3)

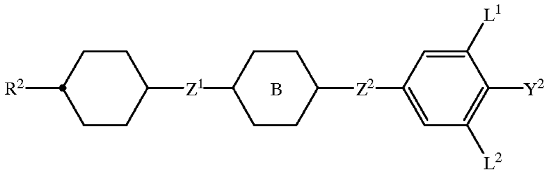

(4)

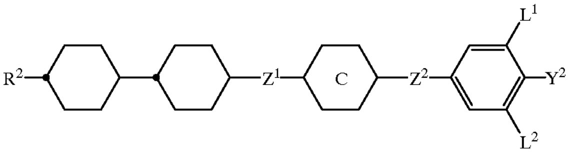

wherein $R^2$ represents an alkyl group having 1 to 10 carbon atoms in which alkyl group not-adjacent any methylene group may be replaced by oxygen atom or vinylene group; and any hydrogen atom in the alkyl group may be replaced by fluorine atom; $Y^2$ represents fluorine atom, chlorine atom, $—OCF_3$, $—OCF_2H$, $—CF_3$, $—CF_2H$, $—CFH_2$, $—OCF_2CF_2H$, or $—OCF_2CFHCF_3$; $L^1$ and $L^2$ independently represent hydrogen atom or fluorine atom; $Z^1$ and $Z^2$ independently represent 1,2-ethylene group, vinylene group, 1,4-butylene group, —COO—, $—CF_2O—$, $—OCF_2—$, or single bond; ring B represents trans-1,4-cyclohexylene group or 1,3-dioxane-2,5-diyl group, or 1,4-phenylene group in which hydrogen atom may be replaced by fluorine atom; ring C represents trans-1,4-cyclohexylene group, or 1,4-phenylene group in which hydrogen atom may be replaced by fluorine atom; and each atom which constitutes those compounds may be replaced by its isotope.

[10] A liquid crystal composition comprising, as a first component, at least one liquid crystalline compound recited in any one of paragraphs [1] to [7] above, and comprising, as a second component, at least one compound selected from the group consisting of the compounds expressed by the general formula (5) or (6)

(5)

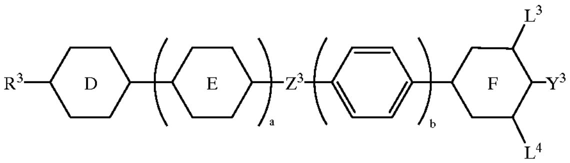

-continued (6)

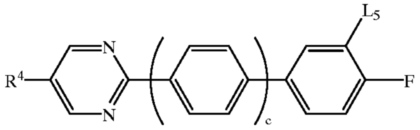

wherein $R^3$ and $R^4$ independently represent an alkyl group having 1 to 10 carbon atoms in which alkyl group not-adjacent any methylene group may be replaced by oxygen atom or vinylene group, and any hydrogen atom in the alkyl group may be replaced by fluorine atom; $Y^3$ represents —CN or —C≡C—CN; ring D represents trans-1,4-cyclohexylene group, 1,4-phenylene group, pyrimidine-2,5-diyl group, or 1,3-dioxane-2,5-diyl group; ring E represents trans-1,4-cyclohexylene group or pyrimidine-2,5-diyl group, or 1,4-phenylene group in which hydrogen atom may be replaced by fluorine atom; ring F represents trans-1,4-cyclohexylene group or 1,4-phenylene group; $Z^3$ represents 1,2-ethylene group, —COO—, or single bond; $L^3$, $L^4$, and $L^5$ independently represent hydrogen atom or fluorine atom; a, b, and c are independently 0 or 1; and each atom which constitutes those compounds may be replaced by its isotope.

[11] A liquid crystal composition comprising, as a first component, at least one liquid crystalline compound recited in any one of paragraphs [1] to [7] above, comprising, as a second component, at least one compound selected from the group consisting of the compounds expressed by any one of the general formulas (2), (3), and (4), and comprising, as a third component, at least one compound selected from the group consisting of the compounds expressed by any one of the general formulas (7), (8), and (9)

(7)

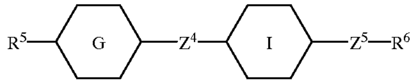

(8)

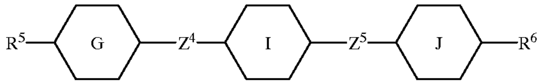

(9)

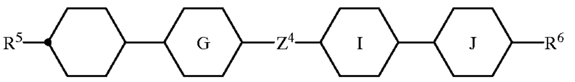

wherein $R^5$ and $R^6$ independently represent an alkyl group having 1 to 10 carbon atoms in which alkyl group not-adjacent any methylene group may be replaced by oxygen atom or vinylene group, and any hydrogen atom in the alkyl group may be replaced by fluorine atom; ring G, ring I, and ring J independently represent trans-1,4-cyclohexylene group or pyrimidine-2,5-diyl group, or 1,4-phenylene group in which one hydrogen atom may be replaced by fluorine atom; $Z^4$ and $Z^5$ independently represent 1,2-ethylene group, vinylene group, —COO—, —C≡C—, or single bond; and each atom which constitutes those compounds may be replaced by its isotope.

[12] A liquid crystal composition comprising, as a first component, at least one liquid crystalline compound recited in any one of paragraphs [1] to [7] above, comprising, as a second component, at least one compound selected from the group consisting of the compounds expressed by any one of the general formulas (2), (3), and (4), and comprising, as a third component, at least one compound selected from the group consisting of the compounds expressed by any one of the general formulas (10), (11), and (12)

(10)

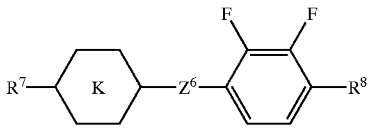

(11)

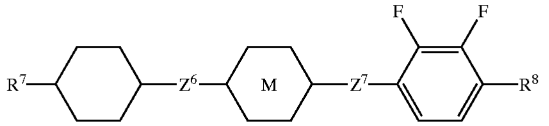

(12)

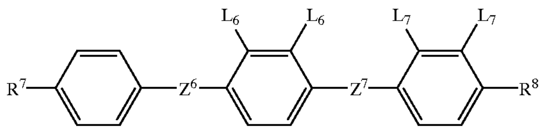

wherein $R^7$ and $R^8$ independently represent an alkyl group having 1 to 10 carbon atoms in which alkyl group not-adjacent any methylene group may be replaced by oxygen atom or vinylene group, and any hydrogen atom in the alkyl group may be replaced by fluorine atom; ring K and ring M independently represent trans-1,4-cyclohexylene or 1,4-phenylene; $L^6$ and $L^7$ independently represent hydrogen atom or fluorine atom, but in no case simultaneously represent $L^6$ and $L^7$ hydrogen atom; $Z^6$ and $Z^7$ independently represent $-CH_2CH_2-$, $-COO-$, or single bond; and each atom which constitutes those compounds may be replaced by its isotope.

[13] A liquid crystal composition comprising, as a first component, at least one liquid crystalline compound recited in any one of paragraphs [1] to [7] above, comprising, as a second component, at least one compound selected from the group consisting of the compounds expressed by any one of the general formulas (7), (8), and (9) described above, and comprising, as a third component, at least one compound selected from the group consisting of the compounds expressed by any one of the general formulas (10), (11), and (12) described above.

[14] A liquid crystal composition comprising, as a first component, at least one liquid crystalline compound recited in any one of paragraphs [1] to [7] above, comprising, as a second component, at least one compound selected from the group consisting of the compounds expressed by any one of the general formulas (2), (3), and (4) described above, and comprising, as a third component, at least one compound selected from the group consisting of the compounds expressed by any one of the general formulas (7), (8), and (9) described above.

[15] A liquid crystal composition comprising, as a first component, at least one liquid crystalline compound recited in any one of paragraphs [1] to [7] above, comprising, as a second component, at least one compound selected from the group consisting of the compounds expressed by the general formula (5) or (6) described above, and comprising, as a third component, at least one compound selected from the group consisting of the compounds expressed by any one of the general formulas (7), (8), and (9) described above.

[16] A liquid crystal composition comprising, as a first component, at least one liquid crystalline compound recited in any one of paragraphs [1] to [7] above, comprising, as a second component, at least one compound selected from the group consisting of the compounds expressed by any one of the general formulas (2), (3), and (4) described above, comprising, as a third component, at least one compound selected from the group consisting of the compounds expressed by the general formula (5) or (6) described above, and comprising, as a fourth component, at least one component selected from the group consisting of the compounds expressed by any one of the general formulas (7), (8), and (9) described above.

[17] A liquid crystal composition comprising at least one optically active compound in addition to the liquid crystal composition recited in any one of paragraphs [8] to [16] above.

[18] A liquid crystal display device fabricated by using the liquid crystal composition recited in any one of paragraphs [8] to [17] above.

Liquid crystalline compounds of the present invention expressed by the general formula (1) are two to four rings compounds having butylene group or propylenoxy group, and 2,3-difluorophenyl group at the same time in the molecular structure. As a matter of course, these liquid crystalline compounds are extremely stable physically and chemically under the environment in which liquid crystal display devices are used, and the compounds are characterized in that they are wide in temperature range exhibiting a liquid crystal phase, excellent in solubility in liquid crystal compositions even at low temperatures, and low in viscosity, and have a negative and large $\Delta\epsilon$.

As described in the section of BACKGROUND ART, whereas compounds having 2,3-difluoro-1,4-phenylene group as a partial structure are already disclosed in patent publications, it is a fact discovered for the first time by the present inventors that the compounds simultaneously having 1,4-butylene group or propylenoxy group as bonding group and 2,3-difluoro-1,4-phenylene group exhibit the characteristic described above, and it is difficult to expect such fact from conventional technology.

In the compounds of the present invention, it is possible to optionally adjust desired physical properties by selecting a proper ring structure, bonding group, and lateral structure among molecule constituting elements. Accordingly, novel liquid crystal compositions and liquid crystal display devices having excellent characteristics, specifically 1) having a wide temperature range of liquid crystal phase,
2) being low in viscosity, and having a negative and large $\Delta\epsilon$,
3) separating no crystals and developing no smectic phase even at very low temperatures,
4) being physically and chemically stable, and being possible to expand the temperature range of their usage, to drive at a low voltage, and to realize a high speed response and high contrast can be provided by using the compound of the present invention as component of liquid crystal compositions.

While any of the compounds of the present invention exhibits preferable physical properties, liquid crystal compositions having physical properties suitable for their use can be produced by using the compound which is expressed by the general formula (1) in which ring $A^1$, ring $A^2$, ring $A^3$, $X^1$, $X^2$, $X^3$, m, and n are properly selected.

That is, when compounds having a negative and large Δε are necessary, it is sufficient to suitably select 2,3-difluoro-1,4-phenylene group for any one of ring $A^1$, ring $A^2$, ring $A^3$, and when compounds having a high optical anisotropy value are necessary, it is sufficient to select compounds in which any one of ring $A^1$, ring $A^2$, and ring $A^3$ is 1,4-phenylene group, and every one of $X^1$, $X^2$, and $X^3$ is single bond. When compounds having their temperature range of liquid crystal phase at high temperature side are necessary, it is sufficient to suitably select three rings or four rings compounds, and when compounds having their temperature range of liquid crystal phase at low temperature side are necessary, it is sufficient to suitably select two rings compounds, respectively.

Compounds in which hydrogen atom on 1,4-phenylene group is replaced by fluorine atom exhibit an excellent solubility at low temperatures.

Compounds expressed by one of the following general formulas (1-1) to (1-12) can be mentioned as particularly preferable ones among the compounds expressed by the general formula (1):

(1-1)

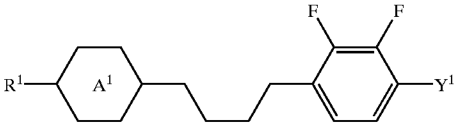

(1-2)

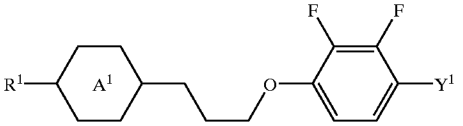

(1-3)

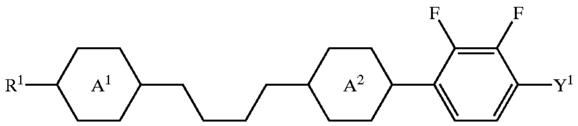

(1-4)

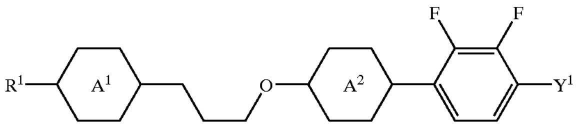

(1-5)

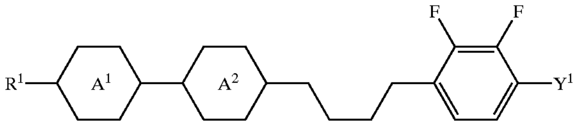

(1-6)

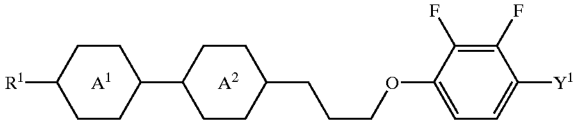

(1-7)

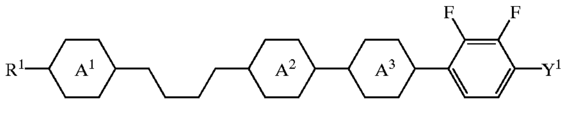

-continued (1-8)

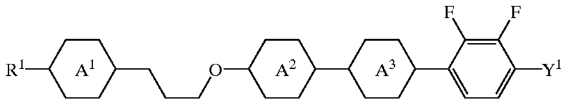

(1-9)

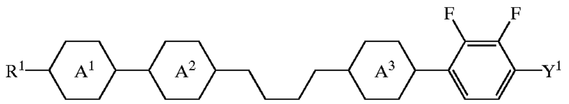

(1-10)

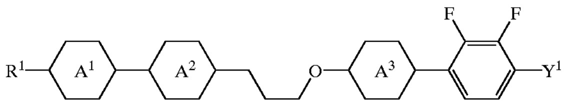

(1-11)

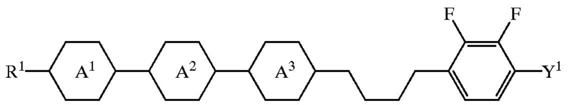

(1-12)

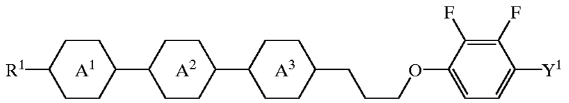

wherein $R^1$, ring $A^1$, ring $A^2$, ring $A^3$, and $Y^1$ have the same meaning as described above.

In the compounds described above, while $R^1$ represents an alkoxy group, alkoxyalkyl group, alkenyl group, alkenyloxy group, alkenyloxyalkyl group, or alkyloxyalkenyl group having 1 to 15 carbon atoms, particularly preferable groups among them are methyl, ethyl, propyl, butyl, pentyl, hexyl, heptyl, octyl, methoxy, ethoxy, propoxy, butoxy, pentyloxy, hexyloxy, heptyloxy, octyloxy, methoxymethyl, ethoxymethyl, propoxymethyl, butoxymethyl, methoxyethyl, ethoxyethyl, propoxyethyl, methoxypropyl, ethoxypropyl, propoxypropyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, 4-pentynyloxy, methoxy-1-propenyl, methoxy-1-pentenyl, and methoxy-3-pentenyl.

In the compounds described above, while $Y^1$ represents hydrogen atom, an alkyl group, alkoxy group, alkoxyalkyl group, alkenyl group, alkenyloxy group, alkenyloxyalkyl group, or alkyloxyalkenyl group having 1 to 15 carbon atoms, particularly preferable groups among them are methyl, ethyl, propyl, butyl, pentyl, hexyl, heptyl, octyl, methoxy, ethoxy, propoxy, butoxy, pentyloxy, hexyloxy, heptyloxy, octyloxy, methoxymethyl, ethoxymethyl, propoxymethyl, butoxymethyl, methoxyethyl, ethoxyethyl, propoxyethyl, methoxypropyl, ethoxypropyl, and propoxypropyl.

Liquid crystal compositions of the present invention are described below. Liquid crystal compositions of the present invention preferably comprise at least one compound expressed by the general formula (1) in the ratio of 0.1 to 99.9% by weight to develop excellent characteristics.

More preferably, the liquid crystal compositions provided by the present invention are completed by mixing compounds selected from the group consisting of the compounds expressed by one of the general formulas (2) to (12) depending on the purposes of the liquid crystal compositions in addition to the first component comprising at least one compound expressed by the general formula (1).

The present invention recited in the paragraphs [12] and [13] above are concerned with N type (having a negative $\Delta\epsilon$) liquid crystal compositions. In the same way as P type (having a positive $\Delta\epsilon$) liquid crystal compositions, N type liquid crystal compositions can be driven by various driving modes, for example, by IPS mode (In Plane Switching Mode). The present invention recited in paragraphs [9], [10], [11], [14], [15], and [16] are concerned with P type liquid crystal compositions. It is possible to control elastic constants of liquid crystal compositions and to improve the miscibility of the compositions at low temperatures by adding a N type liquid crystalline compound to P type liquid crystal compositions.

Following compounds can preferably be mentioned as ones used in the liquid crystal compositions of the present invention and expressed by one of the general formulas (2) to (4):

(2-1)

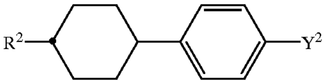

(2-2)

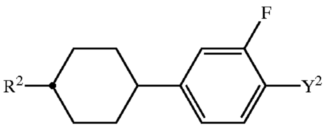

(2-3)

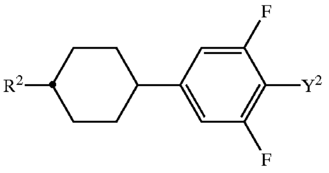

(2-4)

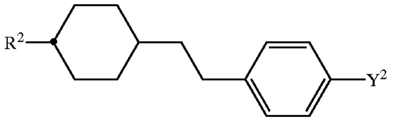

(2-5)

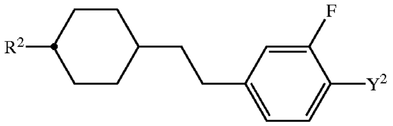

(2-6)

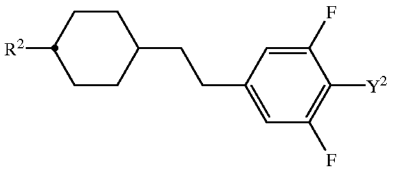

(2-7)

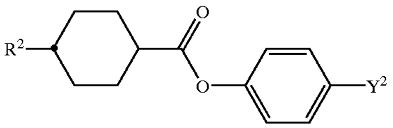

(2-8)

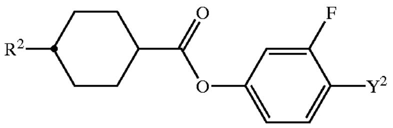

-continued (2-9)

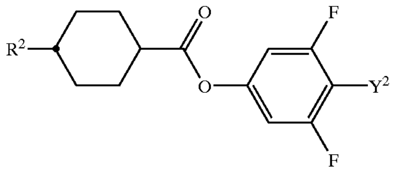

(3-1)

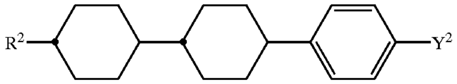

(3-2)

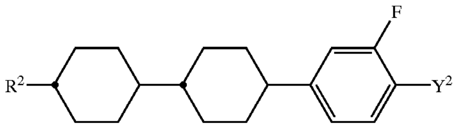

(3-3)

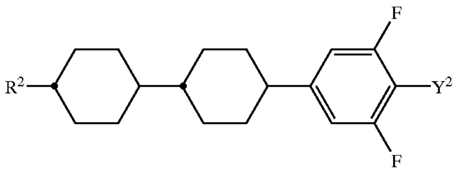

(3-4)

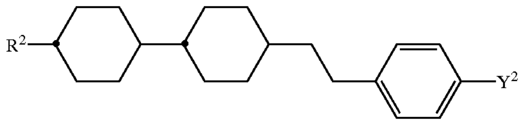

(3-5)

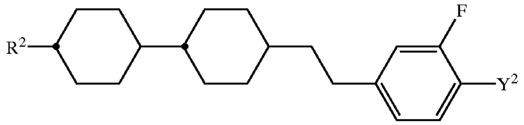

(3-6)

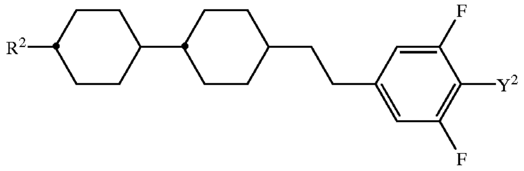

(3-7)

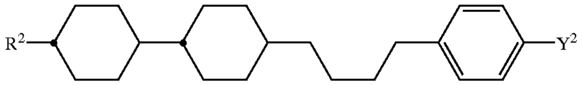

(3-8)

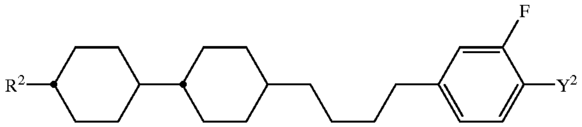

(3-9)

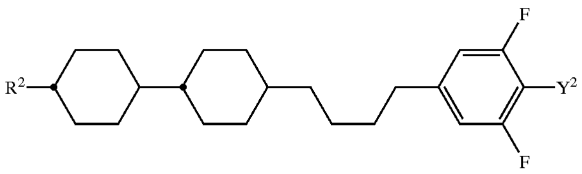

-continued
(3-10)
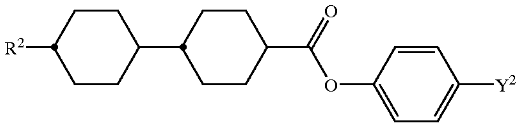
(3-11)
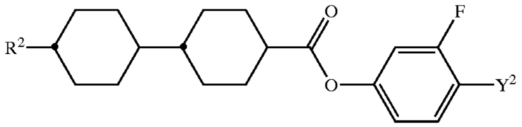
(3-12)
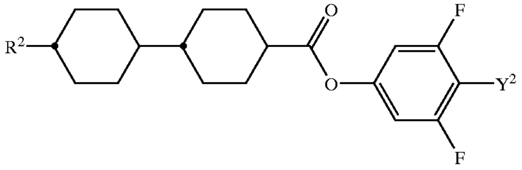
(3-13)
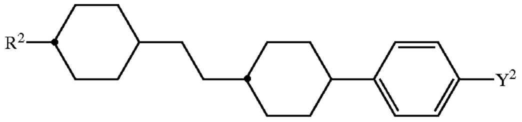
(3-14)
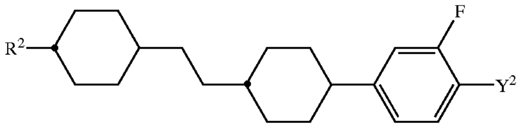
(3-15)
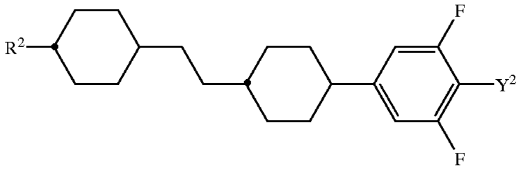
(3-16)
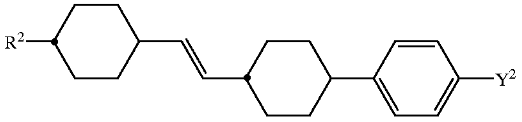
(3-17)
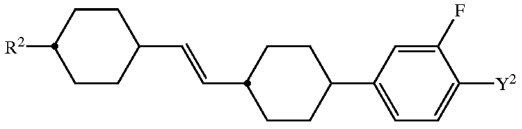
(3-18)
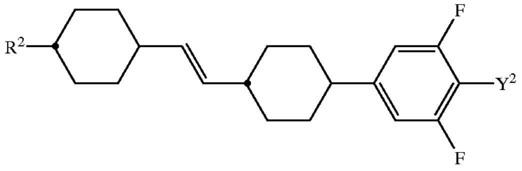
-continued
(3-19)
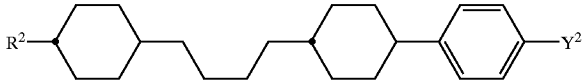
(3-20)
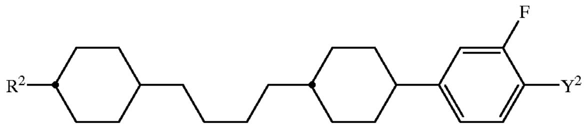
(3-21)
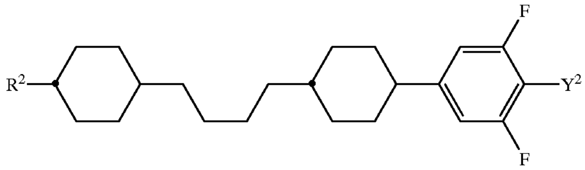
(3-22)
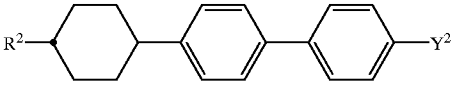
(3-23)
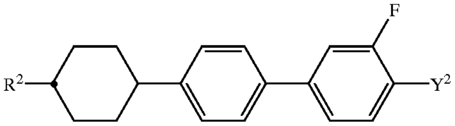
(3-24)
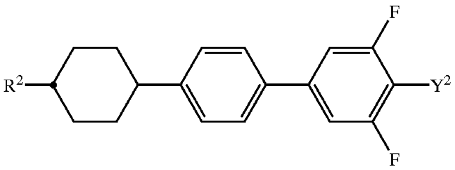
(3-25)
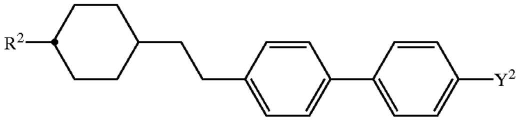
(3-26)
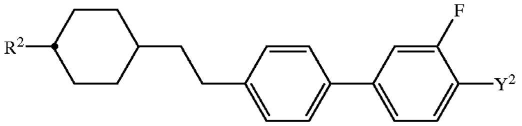
(3-27)
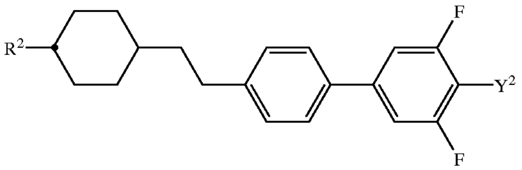
(3-28)
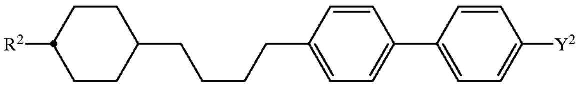

-continued
(3-29)
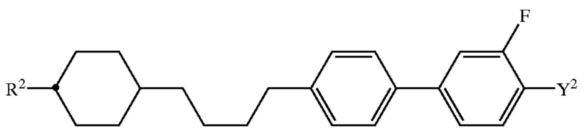
(3-30)
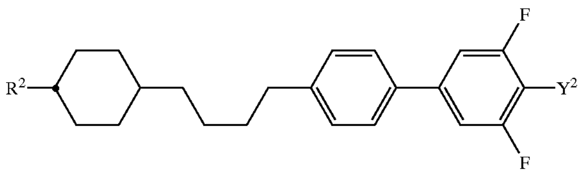
(3-31)
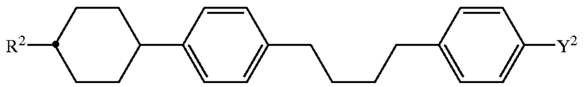
(3-32)
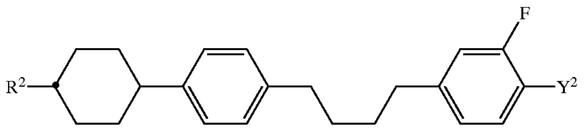
(3-33)
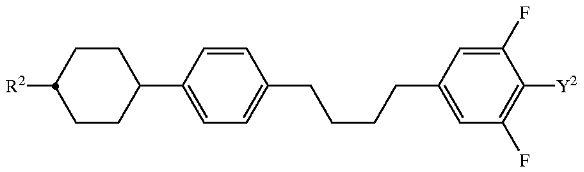
(3-34)
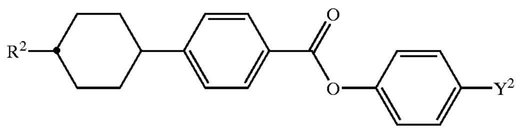
(3-35)
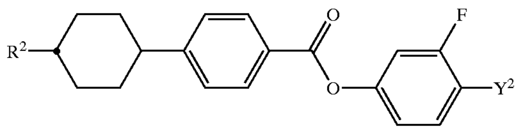
(3-36)
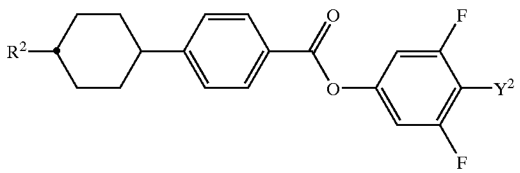
(3-37)
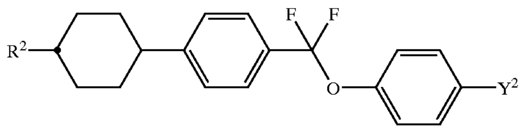
-continued
(3-38)
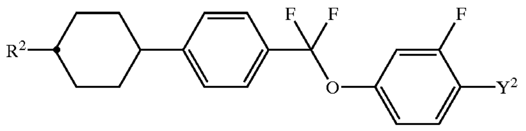
(3-39)
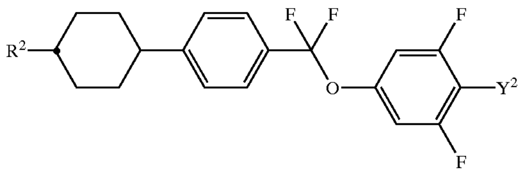
(3-40)
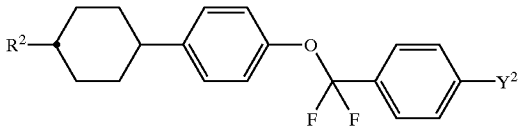
(3-41)
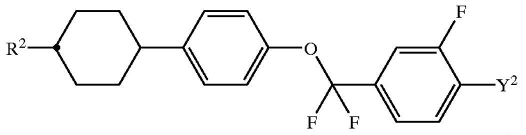
(3-42)
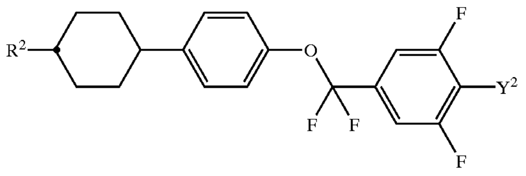
(3-43)
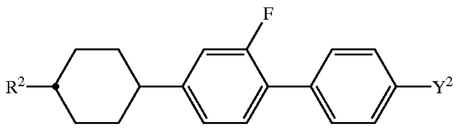
(3-44)
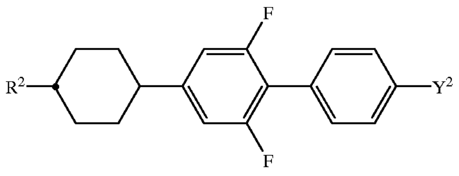
(3-45)
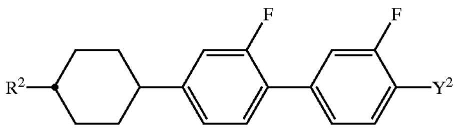
(3-46)
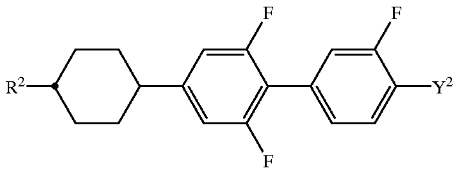

-continued
(3-47)
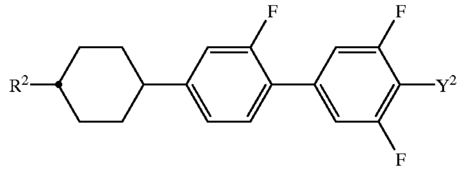
(3-48)
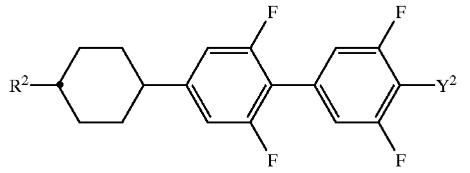
(3-49)
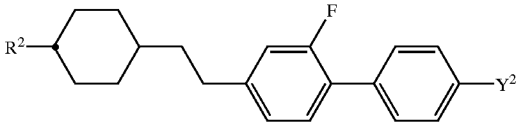
(3-50)
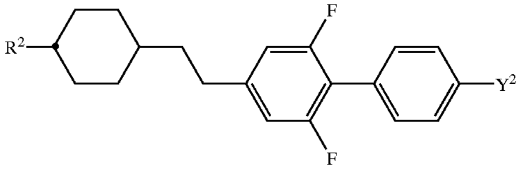
(3-51)
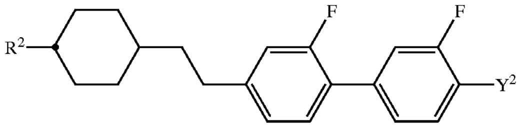
(3-52)
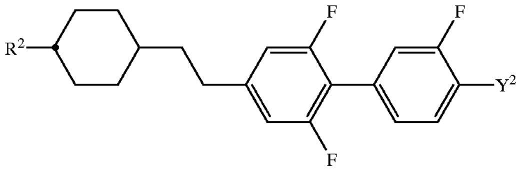
(3-53)
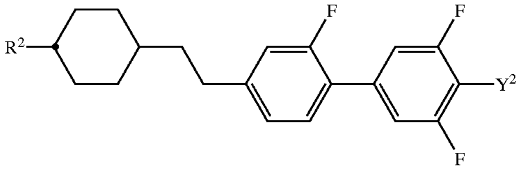
(3-54)
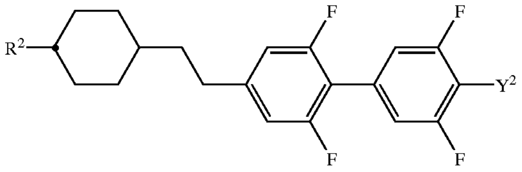
-continued
(3-55)
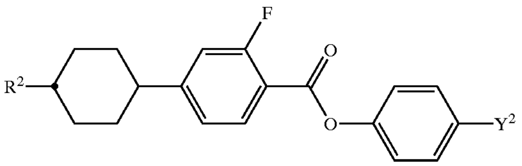
(3-56)
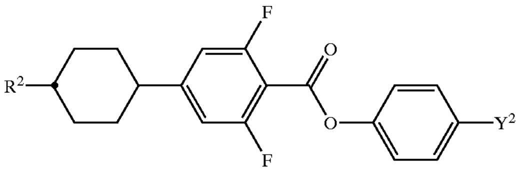
(3-57)
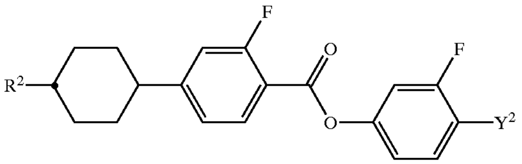
(3-58)
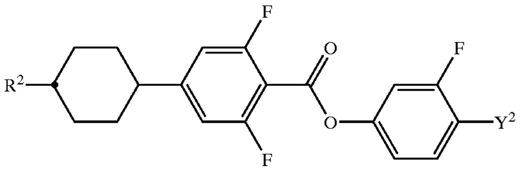
(3-59)
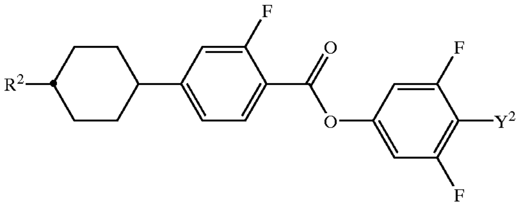
(3-60)
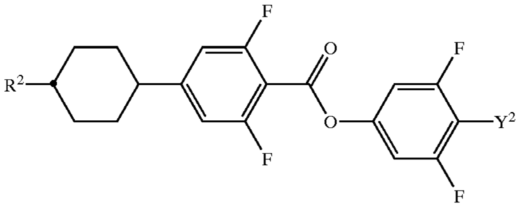
(3-61)
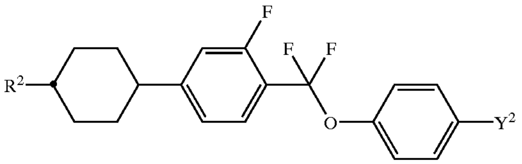

-continued
(3-62)
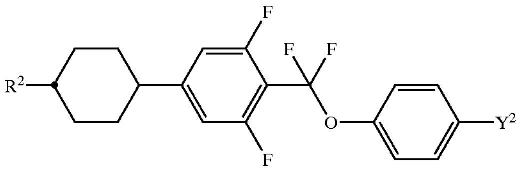
(3-63)
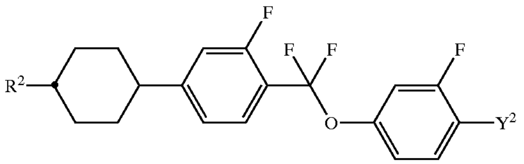
(3-64)
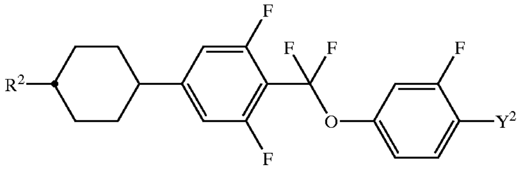
(3-65)
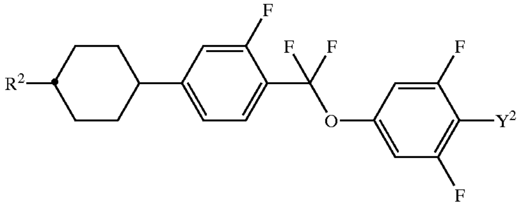
(3-66)
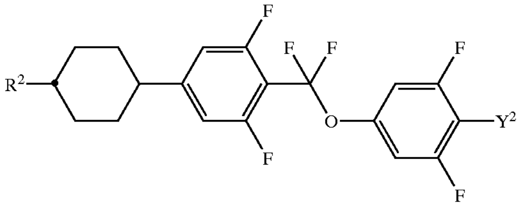
(3-67)
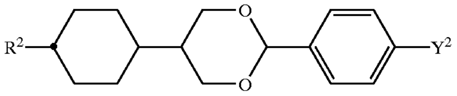
(3-68)
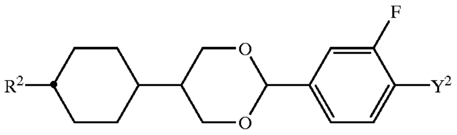
(3-69)
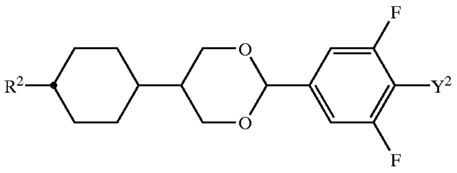
(4-1)
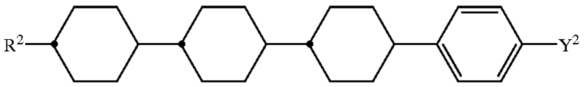
-continued
(4-2)
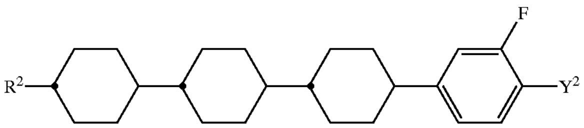
(4-3)
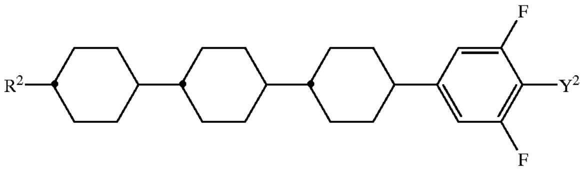
(4-4)
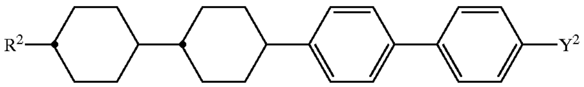
(4-5)
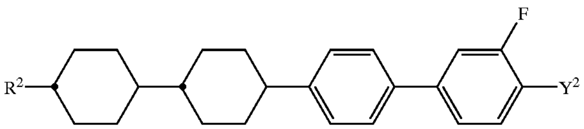
(4-6)
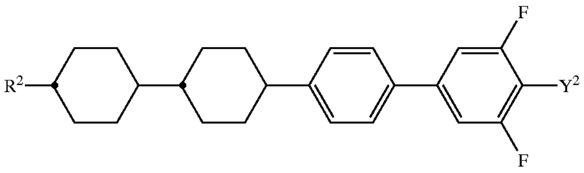
(4-7)
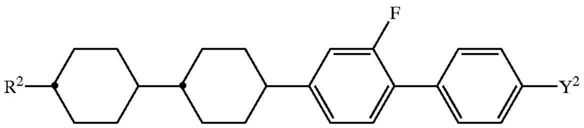
(4-8)
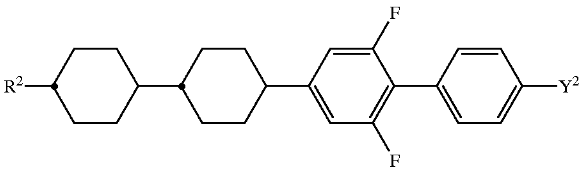
(4-9)
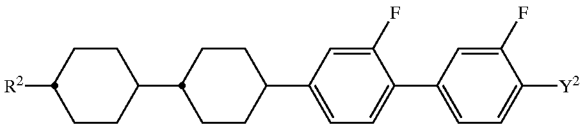
(4-10)
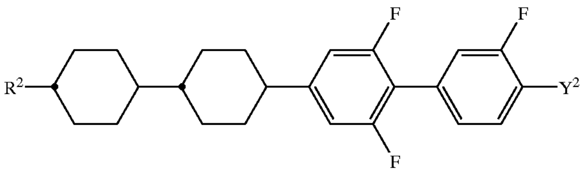

-continued (4-11)

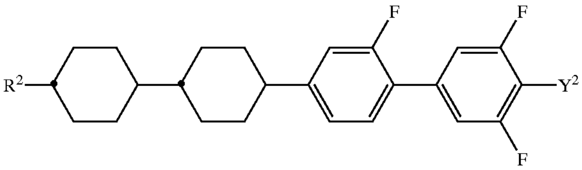

(4-12)

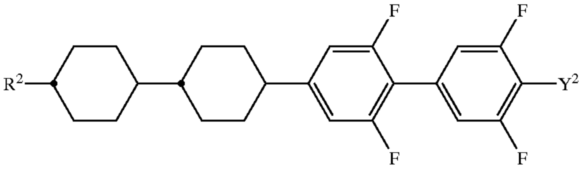

(4-13)

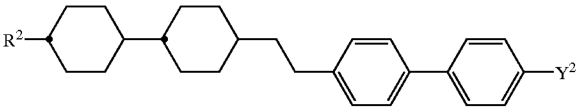

(4-14)

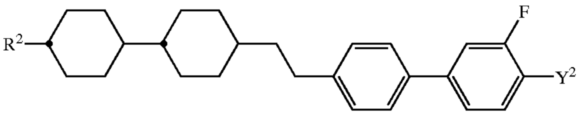

(4-15)

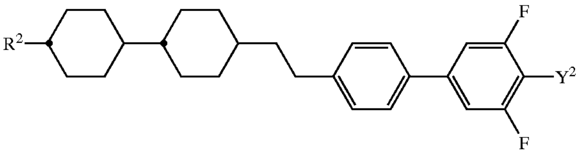

(4-16)

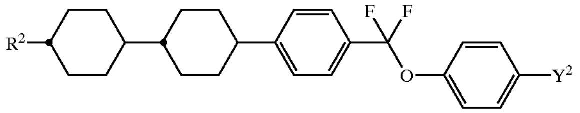

(4-17)

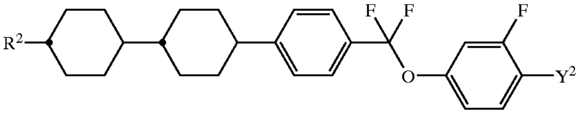

(4-18)

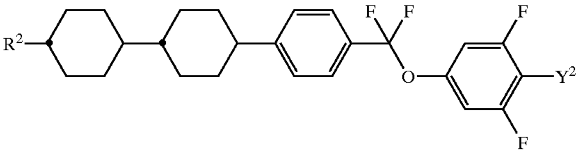

-continued (4-19)

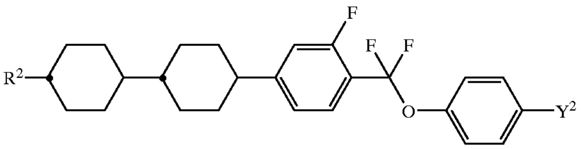

(4-20)

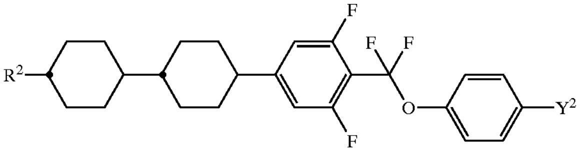

(4-21)

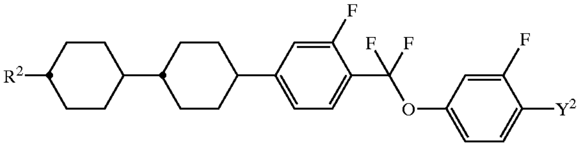

(4-22)

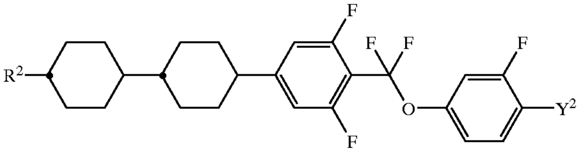

(4-23)

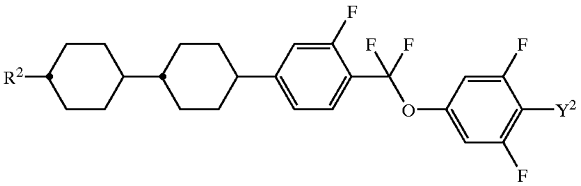

(4-24)

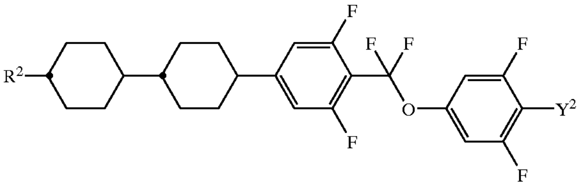

wherein $R^2$ and $Y^2$ have the same meaning as described above.

Compounds expressed by one of the general formulas (2) to (4) have a positive dielectric anisotropy value, are remarkably excellent in thermal stability and chemical stability, and are useful when liquid crystal compositions for TFT (AM-LCD) display mode of which a high reliability such as a particularly high voltage holding ratio or large specific resistivity is required are produced.

When the liquid crystal compositions for TFT display mode are produced, the compounds expressed by one of the general formulas (2) to (4) can be used in the range of 0.1 to 99.9% by weight based on the total amount of liquid crystal composition, and the amount is preferably 10 to 97% by weight and more desirably 40 to 95% by weight. Also, the compositions may further comprise the compound expressed by one of the general formulas (7) to (9) for the purpose of adjusting viscosity. Even when liquid crystal compositions for STN display mode or TN display mode are produced, the compound expressed by one of the general formulas (2) to (4) can be used. In this case, the amount of the compound to be used is preferably less than 50% by weight.
As the compound used in the liquid crystal compositions of the present invention expressed by the general formula (5) or (6), the following compounds can preferably be mentioned:
(5-1)
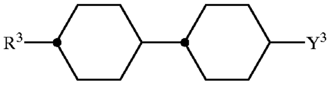
(5-2)
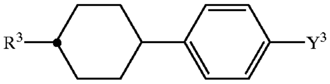
(5-3)
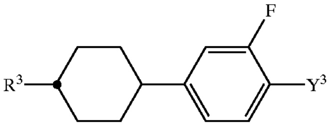
(5-4)
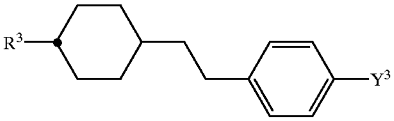
(5-5)
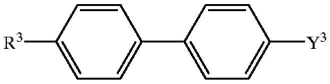
(5-6)
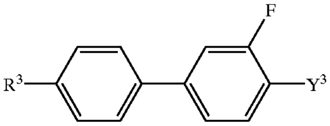
(5-7)
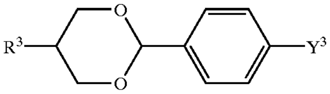
(5-8)
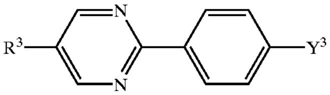
(5-9)
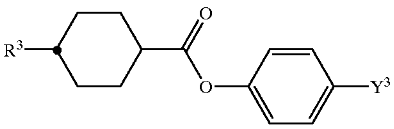
(5-10)
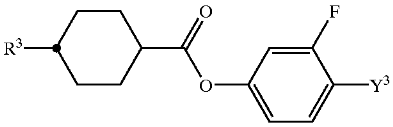
-continued
(5-11)
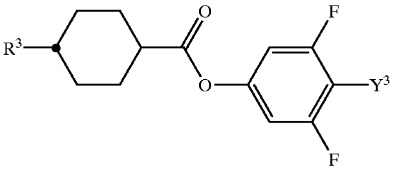
(5-12)
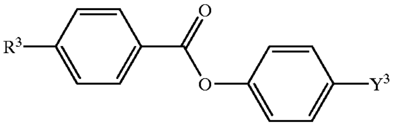
(5-13)
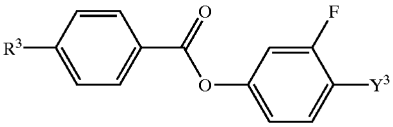
(5-14)
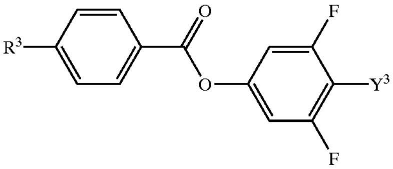
(5-15)
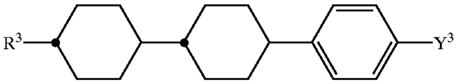
(5-16)
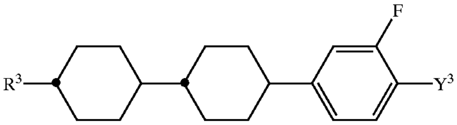
(5-17)
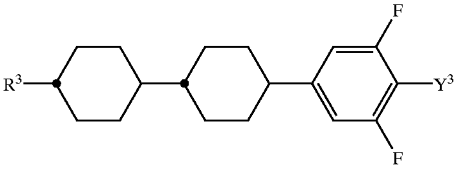
(5-18)
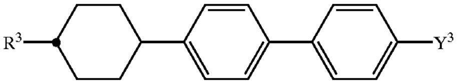
(5-19)
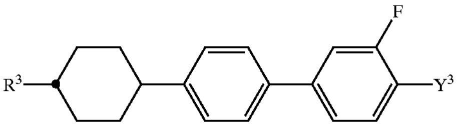
(5-20)
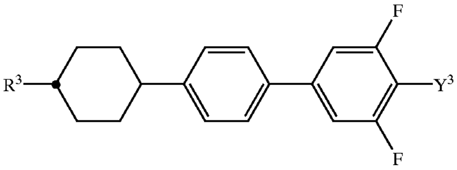
(5-21)
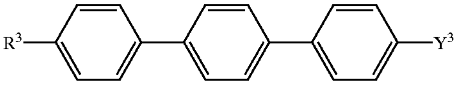

-continued
(5-22)
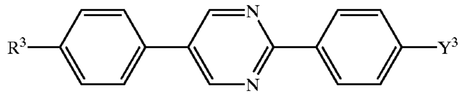
(5-23)
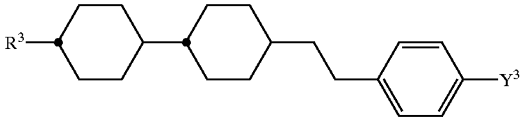
(5-24)
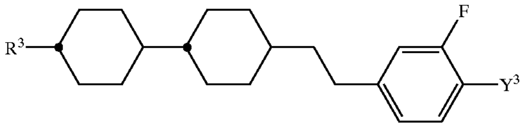
(5-25)
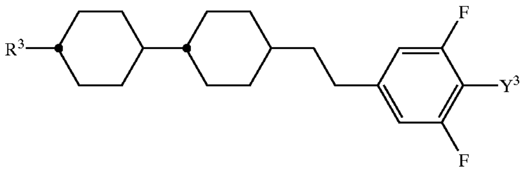
(5-26)
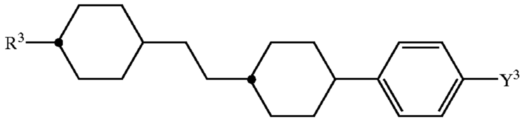
(5-27)
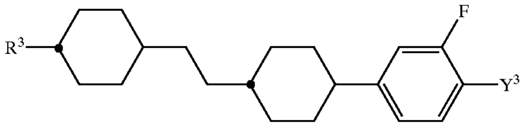
(5-28)
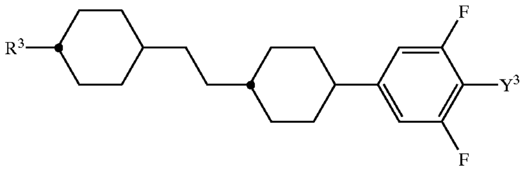
(5-29)
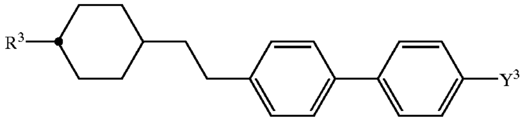
(5-30)
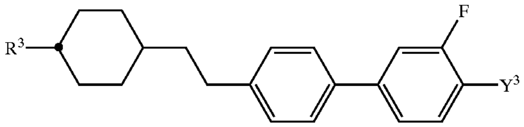
(5-31)
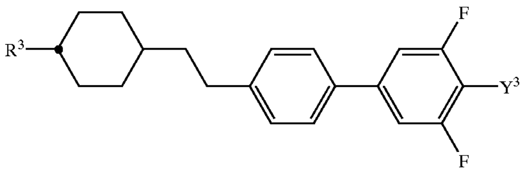
-continued
(5-32)
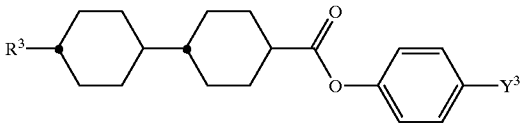
(5-33)
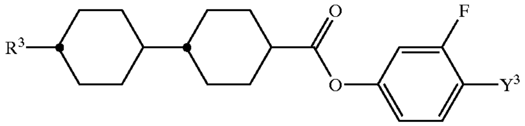
(5-34)
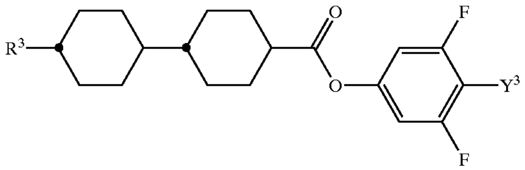
(5-35)
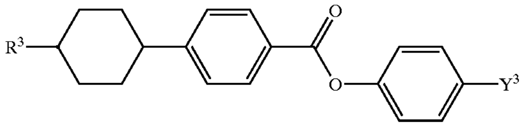
(5-36)
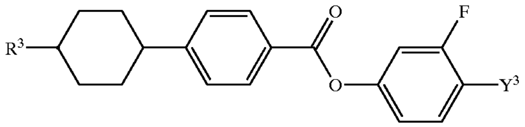
(5-37)
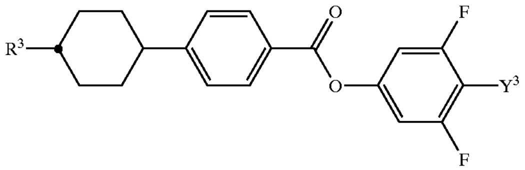
(5-38)
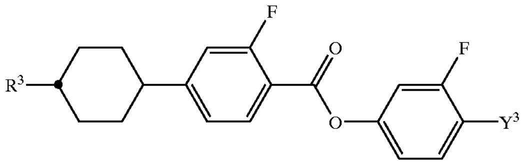
(5-39)
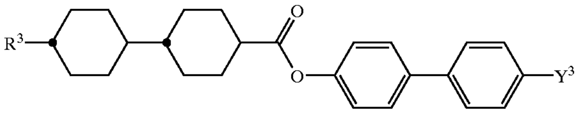
(5-40)
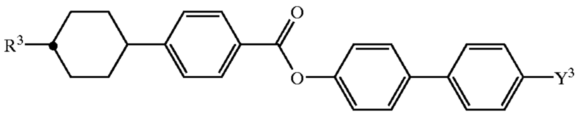
(6-1)
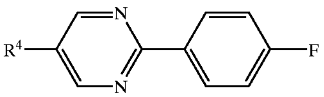

-continued (6-2)

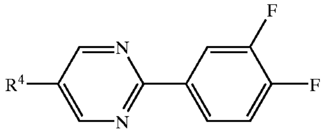

(6-3)

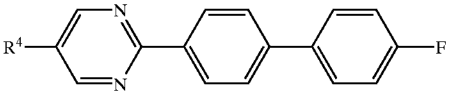

wherein $R^3$, $R^4$, and $Y^3$ have the same meaning as described above.

Compounds expressed by the general formula (5) or (6) have a positive and large dielectric anisotropy value, and are used particularly for the purpose of lowering threshold voltage of liquid crystal compositions. Also, they are used for the purpose of adjusting optical anisotropy value, and widening nematic range such as raising clearing point. Further, they are used even for the purpose of improving the steepness of V-T curve of liquid crystal compositions for STN display mode or TN display mode.

Compounds expressed by the general formula (5) or (6) are useful when liquid crystal compositions particularly for STN display mode or TN display mode are produced.

When the content of the compound expressed by the general formula (5) or (6) in liquid crystal compositions is increased, threshold voltage of liquid crystal compositions lowers but viscosity increases. Accordingly, it is advantageous to use the compound in a large amount since driving at a low voltage becomes possible, so far as viscosity of liquid crystal compositions satisfies required characteristics.

When liquid crystal compositions for STN display mode or TN display mode are produced, the amount of the compound expressed by the general formula (5) or (6) to be used is in the range of 0.1 to 99.9% by weight, preferably 10 to 97% by weight, and more desirably 40 to 95% by weight.

As the compounds used in the liquid crystal compositions of the present invention and expressed by one of the general formulas (7) to (9), the following compounds can preferably be mentioned.

(7-1)

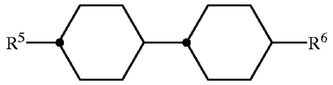

(7-2)

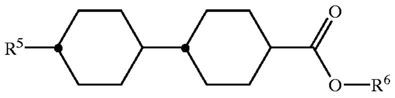

(7-3)

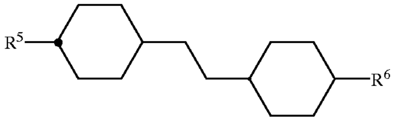

(7-4)

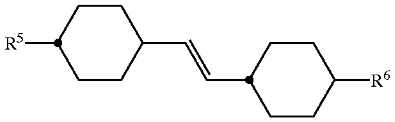

-continued (7-5)

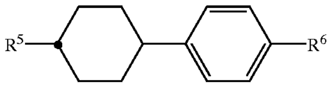

(7-6)

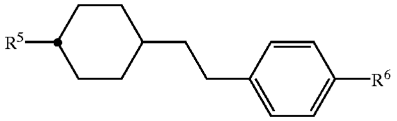

(7-7)

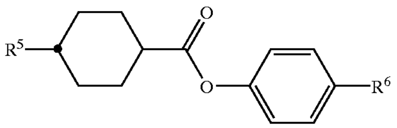

(7-8)

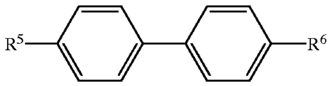

(7-9)

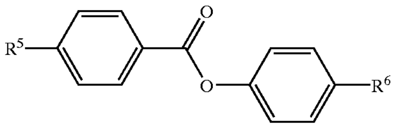

(7-10)

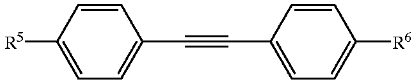

(7-11)

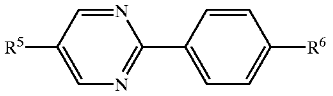

(8-1)

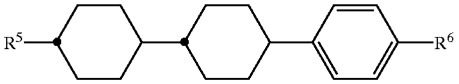

(8-2)

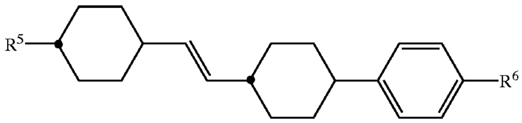

(8-3)

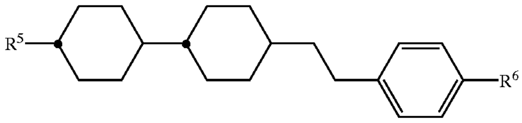

(8-4)

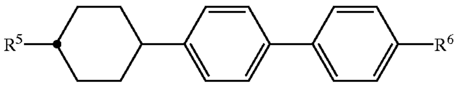

(8-5)

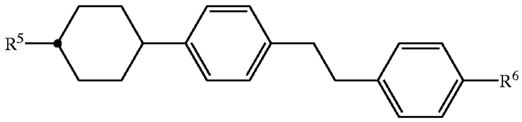

(8-6)

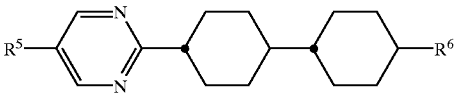

-continued (8-7)

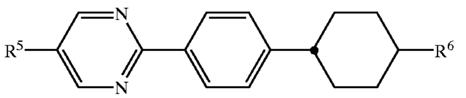

(8-8)

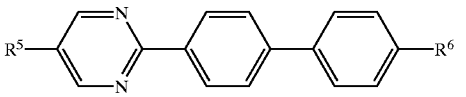

(8-9)

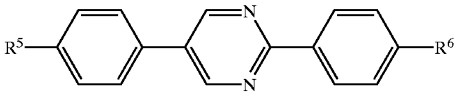

(8-10)

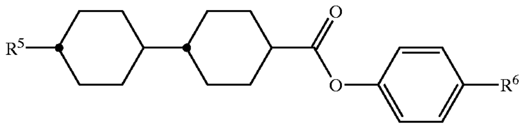

(8-11)

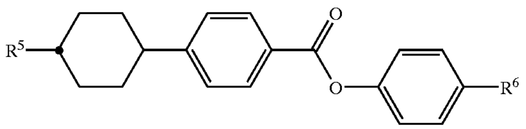

(8-12)

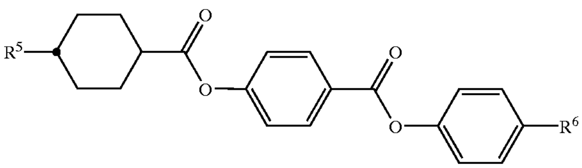

(8-13)

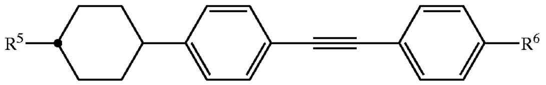

(8-14)

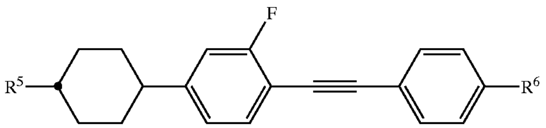

(8-15)

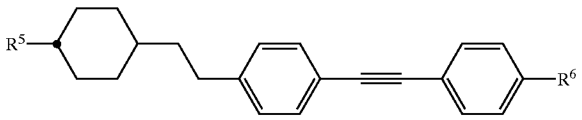

(8-16)

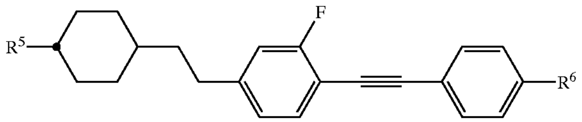

(8-17)

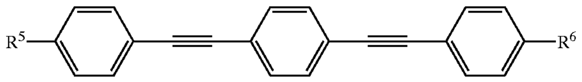

-continued (8-18)

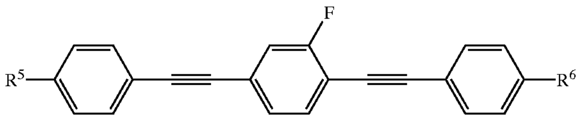

(9-1)

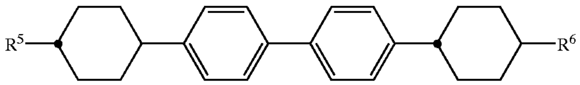

(9-2)

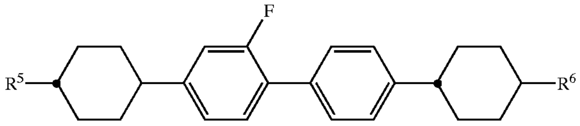

(9-3)

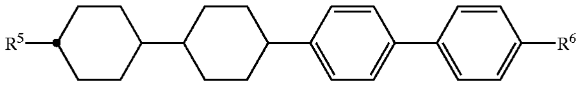

(9-4)

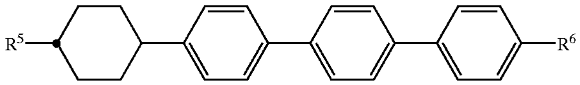

(9-5)

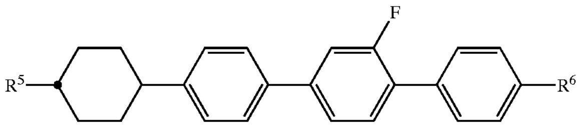

(9-6)

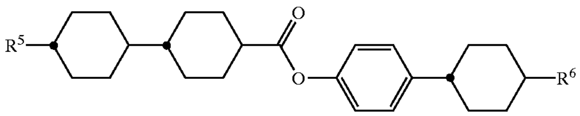

wherein $R^5$ and $R^6$ have the same meaning as described above.

Compounds expressed by one of the general formulas (7) to (9) have a small absolute value of dielectric anisotropy, and are close to neutral. Compounds expressed by the general formula (7) are used principally for the purpose of adjusting viscosity and adjusting optical anisotropy value of liquid crystal compositions. Compounds expressed by the general formula (8) or (9) are used for the purpose of widening nematic range such as raising clearing point, or for the purpose of adjusting optical anisotropy value.

When the content of the compound expressed by one of the general formulas (7) to (9) in liquid crystal compositions is increased, threshold voltage of liquid crystal compositions rises but viscosity reduces. Accordingly, it is desirable to use the compound in a large amount so far as threshold voltage of liquid crystal compositions satisfies required characteristics. When liquid crystal compositions for TFT are produced, the amount of the compound expressed by one of the general formulas (7) to (9) to be used is preferably less than 40% by weight and more desirably less than 35% by weight. When liquid crystal compositions for STN display mode or TN display mode are produced, the amount is preferably less than 70% by weight and more desirably less than 60% by weight.

As the compounds used in the liquid crystal compositions of the present invention and expressed by one of the general formulas (10) to (12), the following compounds can preferably be mentioned:

(10-1)

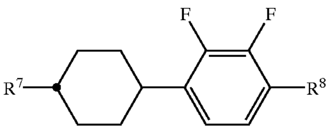

(10-2)

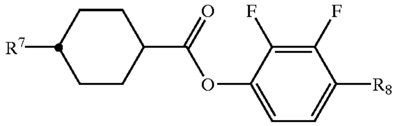

(10-3)

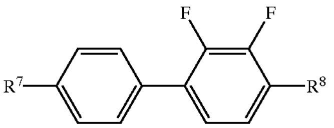

(11-1)

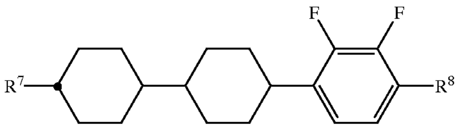

(11-2)

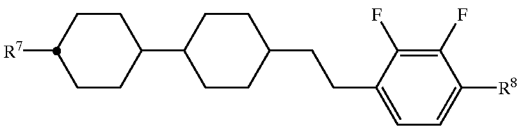

(11-3)

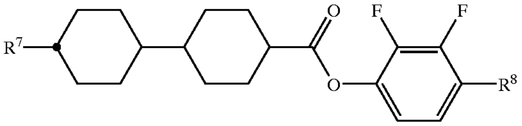

(11-4)

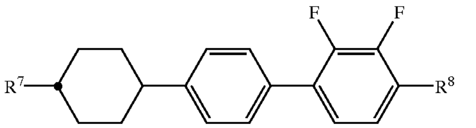

(11-5)

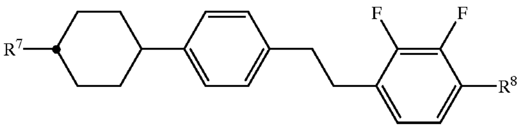

(12-1)

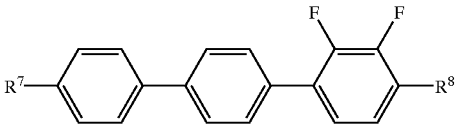

(12-2)

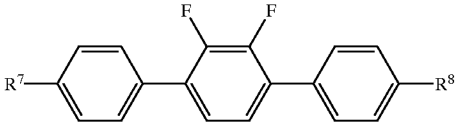

-continued (12-3)

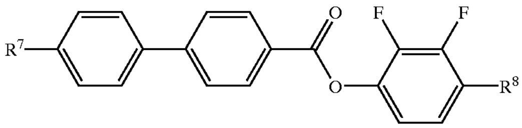

wherein $R^7$ and $R^8$ have the same meaning as described above.

Compounds expressed by one of the general formulas (10) to (12) have a negative dielectric anisotropy value. Compounds expressed by the general formula (10) are two rings compounds, and are used principally for the purpose of adjusting threshold voltage, adjusting viscosity, or adjusting optical anisotropy value. Compounds expressed by the general formula (11) are used for the purpose of widening nematic range such as raising clearing point, or for the purpose of adjusting optical anisotropy value. Compounds expressed by the general formula (12) are used for the purpose of widening nematic range as well as for the purpose of lowering threshold voltage and for the purpose of increasing optical anisotropy value.

Compounds expressed by one of the general formulas (10) to (12) are used principally for N type (having a negative dielectric anisotropy $\Delta\epsilon$) liquid crystal compositions. When the amount of the compound to be used is increased, threshold voltage of liquid crystal compositions lowers but viscosity increases. Accordingly, it is desirable to use the compound in a small amount so far as threshold voltage of liquid crystal compositions is satisfied. However, since these compounds have an absolute value of dielectric anisotropy value of lower than 5, when the amount of the compound used is less than 40% by weight, driving at a low voltage sometimes becomes impossible.

The amount of the compound expressed by one of the general formulas (10) to (12) to be used in liquid crystal compositions is preferably more than 40% by weight when liquid crystal compositions for N type TFT are produced and the amount is more desirably 50 to 95% by weight.

Further, for the purpose of control the elastic constants of liquid crystal compositions and regulating voltage-transmittance curve (V-T curve), the compound expressed by one of the general formulas (10) to (12) is sometimes added to P type (having positive dielectric anisotropy $\Delta\epsilon$) liquid crystal compositions. In such case, the amount of the compound expressed by one of the general formulas (10) to (12) to be used in liquid crystal compositions is preferably less than 30% by weight.

With the exception of such specific cases as liquid crystal compositions for OCB (optically Compensated Birefringence) mode and the likes, an optically active compound is usually added to the liquid crystal compositions of the present invention for the purpose of inducing helical structure of liquid crystal composition to adjust required twist angle and to prevent reverse twist. While any known optically active compounds used for such purposes can be added in the liquid crystal compositions of the present invention, the following optically active compounds can be mentioned as preferable examples:

(Symbol: C15)

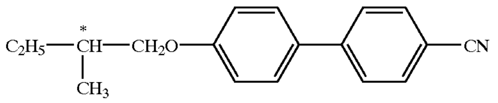

(Symbol: CB15)

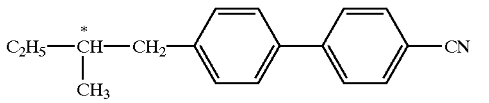

(Symbol: CM21)

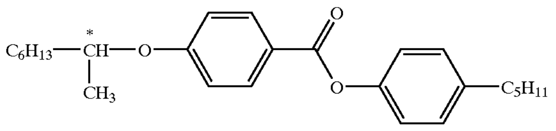

(Symbol: CM33)

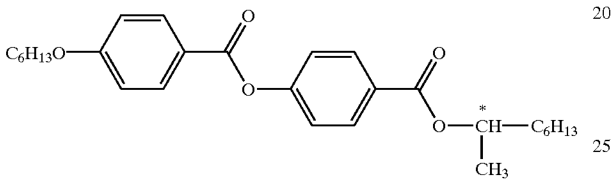

(Symbol: CM44)

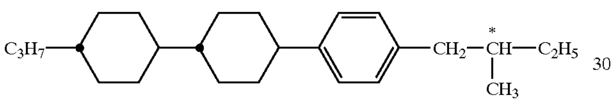

(Symbol: CM45)

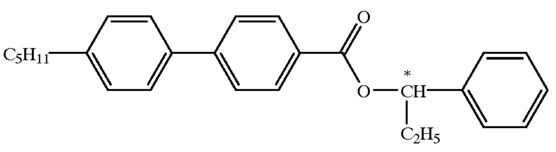

(Symbol: CM47)

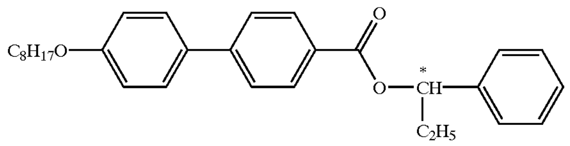

(Symbol: CN)

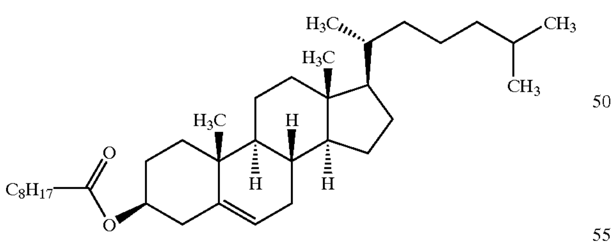

These optically active compounds are usually added to liquid crystal compositions of the present invention to adjust their pitch of twist. The twist pitch is preferably adjusted in the range of 40 to 200 μm in the case of liquid crystal compositions for TFT or TN, and preferably adjusted in the range of 6 to 20 μm in the case of liquid crystal compositions for STN. In the case for bistable TN mode, it is preferable to adjust the pitch in the range of 1.5 to 4 μm. Further, two or more kind of optically active compounds may be added for the purpose of adjusting the dependency of the pitch length on temperature.

Liquid crystal compositions of the present invention can be produced by methods which are conventional by themselves. Generally, a method in which various components are dissolved one another at a high temperature has been adopted.

Further, the liquid crystal compositions of the present invention can be used as ones for guest-host (GH) mode by adding a dichroic dye such as merocyanine type, styryl type, azo type, azomethine type, azoxy type, quinophthalone type, anthraquinone type, and tetrazine type thereto. Alternatively, the liquid crystal compositions can be used as NCAP which is prepared by the microencapsulation of a nematic liquid crystal, or as liquid crystal compositions for polymer dispersed liquid crystal display devices (PDLCD) represented by polymer net work liquid crystal display devices (PNLCD) prepared by forming a polymer of three-dimensional reticulated structure in a liquid crystal. Still further, the liquid crystal compositions of the present invention can be used as ones for electrically controlled birefringence (ECB) mode or dynamic scattering (DS) mode.

[Methods for Producing Compounds]

Compounds of the present invention expressed by the general formula (1) can readily be produced by using ordinary chemical procedures of organic synthesis. For instance, the compounds can readily be synthesized by selecting proper known reactions described in reference books such as Organic Synthesis, Organic Reactions, and Shin-Jikken Kagaku Kouza (Course of New Chemical Experiment), and magazines, and using the reactions in combination.

When butylene group is introduced at the position of a bonding group ($X^1$, $X^2$, and $X^3$), the compounds can be produced, for instance, by the following reaction paths.

In the following, MSG1 and MSG2 independently represent a mesogen (a residue of organic compounds); Hal represents Cl, Br, or I; ring A represents trans-1,4-cyclohexylene group, 1,4-phenylene group in which one or more hydrogen atoms on the six-membered ring may be replaced by a halogen atom, pyrimidine-2,5-diyl group, pyridine-2,5-diyl group, 1,3-dioxane-2,5-diyl group, tetrahydropyran-2,5-diyl group, 1,3-dithian-2,5-diyl group, or tetrahydrothiopyran-2,5-diyl group; and $Y^1$ have the same meaning as described above.

That is, 2-(1,3-dioxane-2-yl)ethyltriphenylphosphonium halide (12) and aldehyde derivative (11) are subjected to the Wittig reaction in an ether type solvent such as tetrahydrofuran (hereinafter abbreviated to THF) and diethyl ether in the presence of a base such as sodium methylate, potassium-t-butoxide (t-BuOK), and butyl lithium to obtain compound (13). Subsequently, aldehyde derivative (14) can be obtained by subjecting compound (13) to hydrogen reduction in a mixed solvent of toluene/Solmix in the presence of a metal catalyst such as palladium/carbon and Raney nickel, and then reacting with a mineral acid such as hydrochloric acid and sulfuric acid, or an organic acid such as formic acid and p-toluenesulfonic acid.

Further, in the same way as that wherein compound (13) is obtained from compound (11), compound (16) can be obtained by subjecting compound (14) and compound (15) to the wittig reaction, and aldehyde derivative (17) can be produced by reacting it with the same acid as described above. Subsequently, derivative (19) having butylene group can be produced by reacting Grignard reagent (18) with compound (17) to conduct Grignard reaction, reacting it with the same acid as described above to dehydrate, and further subjecting to hydrogen reduction by using the same metal catalyst as described above.

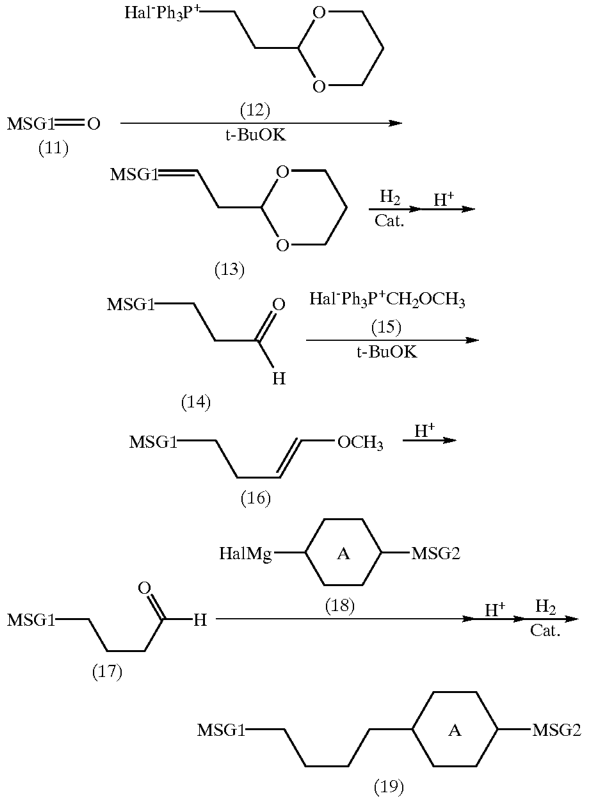

When propylenoxy group having ether bond is introduced at the position of a bonding group ($X^1$, $X^2$, and $X^3$), the compounds can be produced, for instance, by the following reaction paths.

Aldehyde derivative (14) is reacted with lithium aluminum hydride in a solvent such as toluene, THF, and diethyl ether to reduce thereby to obtain alcohol derivative (20). This alcohol derivative (20) is reacted with hydrobromic acid to produce compound (21). Compound (23) having ether bond can be produced by reacting compound (21) with compound (22) in the presence of sodium hydride.

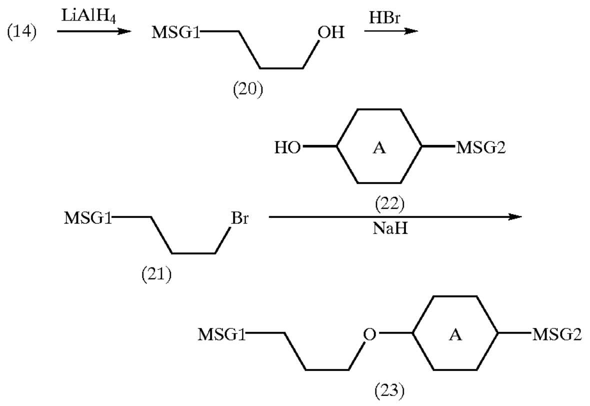

When 2,3-difluoro-1,4-phenylene group is introduced to a ring structure portion, the compounds can be produced, for instance, by the following reaction paths.

a) The case wherein the introduction portion is located at position 4 relative to MSG1 of benzene derivative:

Compound (25) can be obtained by reacting difluorobenzene derivative (24) with n-butyl lithium or sec-butyl lithium in an ether type solvent such as THF and diethyl ether, reacting with zinc chloride, and then reacting with 2,3-difluoro-1-bromobenzene in the presence of a metal catalyst of palladium (0).

b) The case wherein it is introduced in cyclohexanone derivative having MSG1 at position 4:

Compound (28) can be produced by reacting compound (26) with Grignard reagent (27) to conduct the Grignard reaction, dehydrating by the same procedure as described above, and then subjecting to hydrogen reduction.

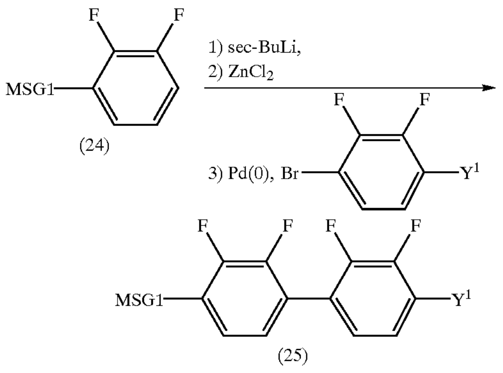

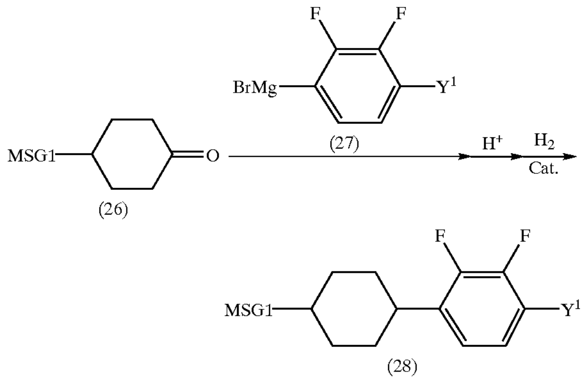

Compounds in which ring $A^1$, ring $A^2$, and ring $A^3$ are silacyclohexane rings can be produced according to the method disclosed in Laid-open Japanese Patent Publication No. Hei 7-70148, Laid-open Japanese Patent Publication No. 7-112990, and Laid-open Japanese Patent Publication Nol Hei 7-149770.

Compounds of the present invention expressed by the general formula (1) can be produced by selecting and using proper reactions described above.

Any of the liquid crystalline compounds of the present invention expressed by the general formula (1) thus obtained has such characteristics that the temperature range in which the compound exhibits a liquid crystal phase is wide, viscosity is low, and $\Delta\epsilon$ is negative and large, and the compound is readily mixed with other various liquid crystal materials even at low temperatures. Accordingly, the compound is remarkably excellent as constituent of nematic liquid crystal compositions suitable for TFT type display mode and IPS mode.

BEST MODE FOR CARRYING OUT THE INVENTION

Now, the present invention will be described in more detail with reference to Examples. However, it should be understood that the scope of the present invention is by no means restricted by such specific Examples. In the Examples, the structure of compounds was confirmed by nuclear magnetic resonance spectrum (hereinafter abbreviated to $^1$H-NMR) and mass spectrum (hereinafter abbreviated to MS). In the data of $^1$H-NMR in the Examples, t indicates triplet, q: quartet, M: multiplet, and J: coupling constant. In the data of MS, $M^+$ indicates molecular ion peak. Further, C indicates crystal, $S_A$: smectic phase A, $S_B$: smectic phase B, N: nematic phase, and Iso: isotropic liquid phase, and the unit of every phase transition temperature is °C.

EXAMPLE 1

Preparation of 2,3-difluoro-1-propyl-4-(trans-4-(4-(trans-4-pentylcyclohexyl)butyl)cyclohexyl)benzene [Compound expressed by the general formula (1) wherein $R^1$ is pentyl group, ring $A^1$ and ring $A^2$ are trans-1,4-cyclohexylene group, $X^1$ is butylene group, $X^2$ is single bond, $Y^1$ is propyl group, m is 1, n is 0 (Compound No. 20)]

First Step

Under nitrogen gas stream, 52.3 g (2150 mmol) of magnesium was added in 100 ml of THF, and a solution of 378 g (1960 mmol) of 2,3-difluoro-1-bromobenzene in 4.0 l of THF was added by drops thereto so that the reaction temperature was maintained at about 50° C. Further, after stirred at room temperature for 1 hour, a solution of 500 g (1630 mmol) of 4-(4-(trans-4-pentylcyclohexyl)butyl) cyclohexanone in 5.0 l of THF was added by drops to the solution and stirred at 50 to 60° C. for 2 hours, and then 1.0 l of saturated aqueous ammonium chloride solution was added to the solution to terminate the reaction. The reaction mixture was filtered with Celite, the solvent was distilled off under a reduced pressure, and then it was extracted with 2.0 l of toluene. The organic layer was washed with 1.0 l of water thrice and dried over anhydrous magnesium sulfate. After the anhydrous magnesium sulfate was removed by filtration, 23.7 g of p-toluenesulfonic acid monohydrate was added to the filtrate and heated to reflux for 4 hours. The organic layer was washed with 1.0 l of water thrice and dried over anhydrous magnesium sulfate. The solvent was distilled off under a reduced pressure, and the residue was subjected to silica gel column chromatography (eluent: heptane) to obtain 436 g of a crude 1,2-difluoro-3-(4-(4-(trans-4-pentylcyclohexyl)-butyl)cyclohexene-1-yl) benzene.

Second Step

In 4.0 l of mixed solvent of toluene/Solmix (1/1) was dissolved 436 g (1080 mmol) of the crude product obtained by the procedures described above, 21.8 g of 5% by weight-palladium/carbon catalyst was added thereto, and then they were stirred at room temperature under the condition of a hydrogen gas pressure of 1 to 2 kg/cm$^2$ for 6 hours. After the catalyst was removed by filtration, the solvent was distilled off under a reduced pressure, and the residue was subjected to silica gel column chromatography (eluent: heptane) and recrystallized from heptane twice to obtain 114 g of 1,2-difluoro-3-(trans-4-(4-(trans-4-pentylcyclohexyl)butyl) cyclohexyl)benzene.

Third Step

Under nitrogen gas stream, a solution prepared by dissolving 30.0 g (74.1 mmol) of 1,2-difluoro-3-(trans-4-(4-(trans-4-pentylcyclohexyl)butyl)cyclohexyl)benzene in 300 ml of THF was cooled down to −70° C., 88.9 ml of sec-butyl lithium (1.0M, cyclohexane solution) was added by drops thereto while being maintained at the same temperature, and stirred at the same temperature for further 2 hours. Subsequently, a suspension prepared by adding 9.98 g (88.9 mmol) of t-BuOK to 100 ml of THF was added by drops to the reaction liquid while being maintained at the same temperature, and stirred at the same temperature for further 1 hour. To the reaction liquid was added by drops a solution of 15.1 g (88.9 mmol) of propyliodide in 150 ml of THF while being maintained at the same temperature and stirred at the same temperature for 5 hours. The reaction was terminated by adding 200 ml of water to the reaction mixture, and the solvent was distilled off under a reduced pressure. Concentrated residue was extracted with 500 ml of toluene, and the organic layer was washed with 200 ml of water thrice and dried over anhydrous magnesium sulfate. The solvent was distilled off under a reduced pressure, and the residue was subjected to silica gel column chromatography (eluent: heptane) to obtain a crude 2,3-difluoro-1-propyl-4-(trans-4-(4-(trans-4-pentylcyclohexyl)butyl) cyclohexyl)benzene. This crude product was recrystallized from heptane thrice to obtain 5.40 g (yield 2.82%) of the subject compound.

Phase transition temperature: C 40.2 $S_B$ 90.9 N 98.0 Iso; $^1$H-NMR: δ: (ppm): 0.50~2.10 (m, 45H), 2.59 (t, 1H, J=7.3 Hz), 6.70~7.10 (m, 2H); MS: m/e=446 ($M^+$).

EXAMPLE 2

Preparation of 1-ethoxy-2,3-difluoro-4-(trans-4-(4-(trans-4-pentylcyclohexyl)butyl)cyclohexyl)benzene [Compound expressed by the general formula (1) wherein $R^1$ is pentyl group, either ring $A^1$ and ring $A^2$ are trans-1,4-cyclohexylene group, $X^1$ is butylene group, $X^2$ is single bond, $Y^1$ is ethoxy group, m is 1, and n is 0 (Compound No. 23)]

First Step

Under nitrogen gas stream, a solution of 60.0 g (148 mmol) of 1,2-difluoro-3-(trans-4-(4-(trans-4-pentylcyclohexyl)butyl)-cyclohexyl)benzene in 600 ml of THF was cooled down to −70° C., 178 ml of sec-butyl lithium (1.0M, cyclohexane solution) was added by drops thereto while being maintained at the same temperature, and stirred at the same temperature for 2 hours. Subsequently, a solution of 30.8 g (296 mmol) of trimethyl borate in 300 ml of THF was added by drops thereto while being at the same temperature, and stirred at the same temperature for further 2 hours. After the reaction temperature was gradually raised up to room temperature, 88.9 g (1480 mmol) of acetic acid was added, 134 g (1180 mmol) of 30% hydrogen peroxide was added by drops, and then stirred at room temperature for 3 hours. The reaction was terminated by adding 300 ml of saturated aqueous sodium thiosulfate solution to the reaction mixture, and the solvent was distilled off under a reduced pressure.

Concentrated residue was extracted with 500 ml of toluene and 100 ml of diethyl ether, the organic layer was washed with 150 ml of saturated aqueous sodium thiosulfate solution twice and with 200 ml of water thrice, and dried over anhydrous magnesium sulfate. The solvent was distilled off under a reduced pressure, and the residue was recrystallized from toluene to obtain 40.0 g of 2,3-difluoro-4-(trans-4-(4-(trans-4-pentylcyclohexyl)butyl)cyclohexyl) phenol.

Second Step

In 400 ml of N,N-dimethyl formamide (hereinafter abbreviated to DMF), was dissolved 40.0 g (95.1 mmol) of 2,3-difluoro- 4-(trans-4-(4-(trans-4-pentylcyclohexyl)butyl) cyclohexyl)phenol, and heated on a water bath up to 50° C. Oily 55% sodium hydride in an amount of 4.97 g (114 mmol) was added thereto, stirred at the same temperature for 10 minutes, and a solution of 15.5 g (142 mmol) of ethyl bromide in 150 ml of DMF was added by drops. After finishing of the dropping, the reaction temperature was raised up to 80° C., and stirred at the same temperature for 5 hours. After cooled down to room temperature, the reaction was terminated by adding 500 ml of water to the reaction mixture, and it was extracted with 1.0 l of toluene. The organic layer was washed with 500 ml of water thrice and dried over anhydrous magnesium sulfate. The solvent was distilled off under a reduced pressure, and the residue was subjected to silica gel column chromatography (eluent: heptane) to obtain a crude 1-ethoxy-2,3-difluoro-4-(trans-4-(4-(trans-4-pentylcyclohexyl)butyl)cyclohexyl)benzene. This crude product was recrystallized from heptane twice and from mixed solvent of heptane/ethanol (6/1) once to obtain 10.3 g (yield 15.5%) of the subject compound.

Phase transition temperature: C 79.2 $S_A$ 94.5 N 125.5 Iso; $^1$H-NMR: δ: (ppm): 0.50~2.05 (m, 41H), 2.73 (t, 1H, J=7.3 Hz), 4.09 (q, 2H, J=7.0 Hz), 6.50~7.00 (m, 2H); MS: m/e=448 ($M^+$).

EXAMPLE 3

Preparation of 1-ethoxy-2,3-difluoro-4-(4-(trans-4-(trans-4-propylcyclohexyl)cyclohexyl)butyl)benzene [Compound expressed by the general formula (1) wherein $R^1$ is propyl group, either ring $A^1$ and ring $A^2$ are trans-1,4-cyclohexylene group, $X^1$ is a single bond, $X^2$ is butylene group, $Y^1$ is ethoxy group, m is 1, and n is 0 (Compound No. 94)]

First Step

Under nitrogen gas stream, a mixture of 1330 g (2930 mmol) of 2-(1,3-dioxane-2-yl)ethyltriphenylphosphonium bromide with 6.0 l of THF was cooled down to −30° C., and 303 g (2700 mmol) of t-BuOK was added thereto and stirred for 1 hour. To this mixture was added by drops a solution of 500 g (2250 mmol) of 4-(trans-4-propylcyclohexyl) cyclohexanone in 3.0 l of THF while being maintained at a temperature lower than −30° C. After finishing of the adding, the reaction temperature was gradually raised up to room temperature and they were stirred for further 5 hours. The reaction mixture was filtered with Celite, the solvent was distilled off under a reduced pressure, and the residue was subjected to silica gel column chromatography (eluent: mixed solvent of toluene/ethyl acetate=9/1) to obtain 652 g of a crude 2-(2-(4-(trans-4-propylcyclohexyl) cyclohexylidene)-ethyl-1,3-dioxane.

Second Step

In 6.5 l of mixed solvent of toluene/Solmix (1/1) was dissolved 652 g (2030 mmol) of the crude product obtained by the procedures described above, 32.6 g of 5% by weight-palladium/carbon catalyst was added thereto, and then they were stirred at room temperature under the condition of a hydrogen gas pressure of 1 to 2 kg/$cm^2$ for 6 hours. After the catalyst was removed by filtration, the solvent was distilled off under a reduced pressure, and the residue was subjected to silica gel column chromatography (eluent: toluene) and recrystallized from heptane to obtain 366 g of 2-(2-(trans-4-(trans-4-propylcyclohexyl)cyclohexyl)ethyl)-1,3-dioxane.

Third Step

In 3.0 l of toluene was dissolved 300 g (930 mmol) of the 2-(2-(trans-4-(trans-4-propylcyclohexyl)cyclohexyl)ethyl)-1,3-dioxane obtained by the procedures described above, 428 g (9300 mmol) of formic acid was added thereto, and they were heated to reflux for 4 hours. The reaction mixture was washed with 600 ml of saturated aqueous sodium bicarbonate solution twice and with 1.0 l of water five times, and the solvent was distilled off under a reduced pressure to obtain 240 g of a crude 3-(trans-4-(trans-4-propylcyclohexyl)-cyclohexyl)propanal.

Fourth Step

Under nitrogen gas stream, a mixture of 405 g (1180 mmol) of methoxymethyltriphenylphosphonium chloride with 4.0 l of THF was cooled down to −30° C., 122 g (1090 mmol) of t-BuOK was added thereto, and they were stirred for 1 hour. To this mixture was added by drops a solution of 240 g (907 mmol) of the crude 3-(trans-4-(trans-4-propylcyclohexyl)cyclohexyl)propanal in 2.4 l of THF while being maintained at a temperature lower than −30° C. After finishing of the dropping, the reaction temperature was gradually raised up to room temperature, and the mixture was stirred for further 5 hours. The reaction mixture was filtered with Celite, the solvent was distilled off under a reduced pressure, and the residue was subjected to silica gel column chromatography (eluent: heptane) to obtain 152 g of a crude 1-methoxy-4-(trans-4-(trans-4-propylcyclohexyl) cyclohexyl)butene.

Fifth Step

In 500 ml of toluene was dissolved 50.0 g (171 ml ) of the crude 1-methoxy-4-(trans-4-(trans-4-propylcyclohexyl) cyclohexyl)butene obtained by the procedures in the fourth step, 78.7 g (1710 mmol) of formic acid was added thereto, and then they were heated to reflux for 4 hours. The reaction mixture was washed with 300 ml of saturated aqueous sodium bicarbonate solution twice and with 500 ml of water five times, and the solvent was distilled off under a reduced pressure to obtain 45.1 g of a crude 4-(trans-4-(trans-4-propylcyclohexyl)cyclohexyl)butanal.

Sixth Step

Under nitrogen gas stream, a solution of 30.7 g (194 mmol) of 1-ethoxy-2,3-difluorobenzene in 300 ml of THF was cooled down to −70° C., 194 ml of sec-butyl lithium (1.0M cyclohexane solution) was added by drops thereto while being maintained at the same temperature, and they were stirred at the same temperature for 2 hours. To this reaction mixture was added by drops a solution of 45.1 g (162 mmol) of the crude 4-(trans-4-(trans-4-propylcyclohexyl)cyclohexyl)butanal obtained by the reaction in the fifth step in 450 ml of THF while being maintained at the same temperature, and stirred for 2 hours. Subsequently, they were raised up to −50° C. and stirred for 2 hours. The reaction mixture was added to 200 ml of water to terminate the reaction, the solvent was distilled off under a reduced pressure, the residue was extracted with 500 ml of toluene, and the organic layer was washed with 100 ml of water thrice, and then dried over anhydrous magnesium sulfate. After the anhydrous magnesium sulfate was removed by filtration, 2.83 g of p-toluenesulfonic acid monohydrate was added to the filtrate, and heated to reflux for 4 hours. The organic layer was washed with 200 ml of water thrice and then dried over anhydrous magnesium sulfate. The solvent was distilled off under a reduced pressure and the residue was subjected to silica gel column chromatography (eluent: mixed solvent of heptane/toluene=7/3) to obtain 50.2 g of a crude 1-ethoxy-2,3-difluoro-4-(4-(trans-4-(trans-4-propylcyclohexyl)cyclohexyl)-1-butenyl) benzene.

Seventh Step

In 500 ml of mixed solvent of toluene/Solmix (1/1) was dissolved 50.2 g (120 mmol) of the crude product obtained by the procedures described above, 15.1 g of 5% by weight-palladium/carbon catalyst was added thereto, and they were stirred at room temperature under the condition of a hydrogen gas pressure of 1 to 2 kg/$cm^2$ for 6 hours. After the catalyst was removed by filtration, the solvent was distilled off under reduced pressure, and the residue was subjected to silica gel column chromatography (eluent: mixed solvent of heptane/toluene=7/3) to obtain a crude 1-ethoxy-2,3-difluoro-4-(4-(trans-4-(trans-4-propylcyclohexyl)cyclohexyl)butyl)benzene. This crude product was recrystallized from heptane twice to obtain 24.3 g (yield 9.90%) of the subject compound.

Phase transition temperature: C 44.4 $S_A$ 107.2 N 129.0 Iso; $^1$H-NMR: δ: (ppm): 0.45~2.10 (m, 36H), 2.58 (t, 2H, J=7.0 Hz), 4.09 (q, 2H, J=7.0 Hz), 6.50~7.00 (m, 2H); MS: m/e=420 ($M^+$).

EXAMPLE 4

Preparation of 3-(trans-4-(trans-4-propylcyclohexyl)cyclohexyl)propyl 2,3-difluoro-4-(2,3-difluoro-4-pentylphenyl)phenyl ether [Compound expressed by the general formula (1) wherein $R^1$ is propyl group, either ring $A^1$ and ring $A^2$ are trans-1,4-cyclohexylene group, ring $A^3$ is 2,3-difluoro-1,4-phenylene group, either $X^1$ and $X^3$ are single bond, $X^2$ is propyloxylene group, $Y^1$ is pentyl group, m is 1, and n is 1 (Compound No. 237)]

First Step

Under nitrogen gas stream, a solution of 400 g (1510 mmol) of the crude 3-(trans-4-(trans-4-propylcyclohexyl)cyclohexyl)propanal obtained in the same manner as in the third step in Example 1 in 2.0 l of THF was added by drops to a mixture which was prepared by adding 43.0 g (1130 mmol) of lithium aluminum hydride to 400 ml of THF cooled down to a temperature lower than 5° C., while being maintained at the same temperature. After finishing of the adding, they were stirred at room temperature for 6 hours. This reaction mixture was gradually added to 500 ml of 2N aqueous sodium hydroxide solution and stirred at 50° C. for 30 minutes. The reaction mixture was filtered with Celite, the solvent was distilled off under a reduced pressure, and the residue was extracted with 2.0 l of ethyl acetate. The organic layer was dried over anhydrous magnesium sulfate, and the solvent was distilled off under a reduced pressure to obtain 341 g of a crude 3-(trans-4-(trans-4-propylcyclohexyl)cyclohexyl)propanol.

Second Step

To 350 ml of xylene were added 341 g (1280 mmol) of the crude 3-(trans-4-(trans-4-propylcyclohexyl)cyclohexyl)propanol obtained by the procedures described above and 881 g (5120 mmol) of 47% hydrobromic acid, water was removed by azeotropic distillation, and then the mixture was stirred at 150° C. for 2 hours. To the reaction mixture was added 1.0 l of toluene, and it was washed with 300 ml of saturated aqueous sodium carbonate solution twice and with 400 ml of water thrice, and then dried over anhydrous magnesium sulfate. The solvent was distilled off under a reduced pressure, and the residue was subjected to silica gel column chromatography (eluent: heptane) to obtain 156 g of a crude 1-bromo-3-(trans-4-(trans-4-propylcyclohexyl)cyclohexyl)propane.

Third Step

Under nitrogen gas stream, 29.8 g (683 mmol) of 55% sodium hydride was added to 100 ml of DMF and cooled with water, a solution of 74.0 g (569 mmol) of 2,3-difluorophenol in 700 ml of DMF was added by drops thereto, and they were stirred for 1 hour. To the reaction mixture was added by drops a solution of 156 g (474 mmol) of the crude 1-bromo-3-(trans-4-(trans-4-propylcyclohexyl)cyclohexyl)propane in 400 ml of mixed solvent of DMF/toluene (3/1), and then they were stirred at 80° C. for 3 hours. The reaction mixture was added to 500 ml of water to terminate the reaction, and the organic layer was separated, washed with 500 ml of water thrice, and then dried over anhydrous magnesium sulfate. The solvent was distilled off under a reduced pressure, and the residue was subjected to silica gel column chromatography (eluent: heptane) and recrystallized from heptane to obtain 101 g of 3-(trans-4-(trans-4-propylcyclohexyl)cyclohexyl)propyl 2,3-difluorophenyl ether.

Fourth Step

Under nitrogen gas stream, 101 g (267 mmol) of the 3-(trans-4-(trans-4-propylcyclohexyl)cyclohexyl)propyl 2,3-difluorophenyl ether obtained by the procedures described above was dissolved in 1.0 l of THF and cooled down to −70° C. To this solution was added by drops 320 ml of sec-butyl lithium (1.0M, cyclohexane solution) while being maintained at the same temperature, and stirred at the same temperature for 2 hours. To the reaction mixture was added by drops 640 ml of zinc chloride (0.5M, THF solution), and stirred at the same temperature for 1 hour, the reaction temperature was gradually raised up to room temperature, and they were stirred for 1 hour. To the reaction mixture was added 1.00 g of tetrakis(triphenylphosphine) palladium (0), and a solution of 61.8 g (15.9 mmol) of 2,3-difluoro-1-bromobenzene in 600 ml of THF was added by drops thereto, and heated to reflux for 3 hours. The reaction mixture was added to 1.0 l of water to terminate the reaction, the solvent was distilled off under a reduced pressure, and the residue was extracted with 3.0 l of toluene. The organic layer was washed with 1.0 l of water thrice and dried over anhydrous magnesium sulfate. The solvent was distilled off under a reduced pressure, and the residue was subjected to silica gel column chromatography (eluent: toluene) to obtain 55.3 g of a crude 3-(trans-4-(trans-4-propylcyclohexyl)cyclohexyl)propyl 2,3-difluoro-4-(2,3-difluorophenyl)phenyl ether.

Fifth Step

Under nitrogen gas stream, a solution prepared by dissolving 55.3 g (112 mmol) of the 3-(trans-4-(trans-4-propylcyclohexyl)cyclohexyl)propyl 2,3-difluoro-4-(2,3-difluorophenyl)phenyl ether obtained by the procedures described above in 550 ml of THF was cooled down to −70° C., and 134 ml of sec-butyl lithium (1.0M, cyclohexane solution) was added by drops thereto while being maintained at the same temperature and stirred at the same temperature for 2 hours. To the reaction mixture was added by drops a suspension which was prepared by adding 15.0 g (134 mmol) of t-BuOK to 150 ml of THF, while being maintained at the same temperature, and stirred at the same temperature for further 1 hour. To the reaction mixture was added by drops a solution of 26.5 g (134 mmol) of pentyliodide in 300 ml of THF while being maintained at the same temperature and stirred at the same temperature for 5 hours. The reaction mixture was added to 300 ml of water to terminate the reaction, and the solvent was distilled off under a reduced pressure. The residue was extracted with 700 ml of toluene, and the organic layer was washed with 300 ml of water thrice and dried over anhydrous magnesium sulfate. The solvent was distilled off under a reduced pressure, and the residue was subjected to silica gel column chromatography (eluent: mixed solvent of heptane/toluene=7/3) to obtain a crude 3-(trans-4-(trans-4-propylcyclohexyl)propyl 2,3-difluoro-4-(2,3-difluoro-4-pentylphenyl)phenyl ether. This crude product was recrystallized from heptane twice and from mixed solvent of heptane/ethanol (4/1) once to obtain 10.2 g (yield 1.21%) of the subject compound.

MS: m/e=560 ($M^+$).

EXAMPLE 5

Preparation of 1-ethoxy-2,3-difluoro-4-(2,3-difluoro-4-(4-(trans-4-(trans-4-propylcyclohexyl)cyclohexyl)butyl) phenyl)benzene [Compound expressed by the general formula (1) wherein $R^1$ is propyl group, either ring $A^1$ and ring $A^2$ are trans-1,4-cyclohexylene group, ring $A^3$ is 2,3-difluoro-1,4-phenylene group, either $X^1$ and $X^3$ are single bond, $X^2$ is butylene group, $Y^1$ is ethoxy group, m is 1, and n is 1 (Compound No. 238)]

First Step

Under nitrogen gas stream, 8.05 g (331 mmol) of magnesium was added to 20.0 ml of THF, and a solution of 58.1 g (301 mmol) of 2,3-difluoro-1-bromobenzene in 600 ml of THF was added by drops thereto so that the reaction temperature was maintained at about 50° C. and then stirred at room temperature for 1 hour. To the reaction solution was added by drops a solution of 70.0 g (251 mmol) of the crude 4-(trans-4-(trans-4-propylcyclohexyl)cyclohexyl)butanal obtained by the same manner as in the fifth step of Example 1 in 700 ml of THF, stirred at 50 to 60° C. for 2 hours, and then 200 ml of saturated aqueous ammonium chloride solution was added thereto to terminate the reaction. The reaction mixture was filtered with Celite, the solvent was distilled off under a reduced pressure, and then the residue was extracted with 700 ml of toluene. The organic layer was washed with 400 ml of water thrice and then dried over anhydrous magnesium sulfate. After the anhydrous magnesium sulfate was filtered off, 3.56 g of p-toluenesulfonic acid monohydrate was added to the filtrate, and heated to reflux for 4 hours. The organic layer was washed with 300 ml of water thrice and dried over anhydrous magnesium sulfate. The solvent was distilled off under a reduced pressure, and the residue was subjected to silica gel column chromatography (eluent: heptane) to obtain 63.5 g of a crude 2,3-difluoro-4-(4-(trans-4-(trans-4-propylcyclohexyl) cyclohexyl)-1-butenyl)benzene.

Second Step

To 600 ml of mixed solvent of toluene/Solmix (1/1) was dissolved 63.5 g (170 mmol) of the crude product obtained by the procedures described above, 3.18 g of 5% by weight-palladium/carbon catalyst was added thereto, and then they were stirred at room temperature under the condition of a hydrogen gas pressure of 1 to 2 kg/$cm^2$ for 6 hours. After the catalyst was removed from the reaction mixture by filtration, the solvent was distilled off under a reduced pressure, and the residue was subjected to silica gel column chromatography (eluent: heptane) to obtain 60.0 g of a crude 2,3-difluoro-4-(4-(trans-4-(trans-4-propylcyclohexyl) cyclohexyl)butyl)benzene.

Third Step

Under nitrogen gas stream, 60.0 g (159 mmol) of the crude 2,3-difluoro-4-(4-(trans-4-(trans-4-propylcyclohexyl) cyclohexyl)butyl)benzene was dissolved in 600 ml of THF, cooled down to −70° C., and 191 ml of sec-butyl lithium (1.0M, cyclohexane solution) was added by drops thereto while being maintained at the same temperature and stirred at the same temperature for 2 hours. To the reaction mixture was added by drops a solution of 60.7 g (239 mmol) of iodine in 600 ml of THF while being maintained at the same temperature, the reaction temperature was gradually raised up to room temperature, and then they were stirred for 30 minutes. The reaction mixture was added to 300 ml of saturated aqueous sodium thiosulfate solution to terminate the reaction, and the solvent was distilled off under a reduced pressure. The residue was extracted with 700 ml of toluene, and the organic layer was washed with 300 ml of saturated aqueous sodium thiosulfate solution twice and 200 ml of saturated aqueous sodium carbonate solution once, and 300 ml of water thrice, and then dried over anhydrous magnesium sulfate. The solvent was distilled off under a reduced pressure, and the residue was subjected to silica gel column chromatography (eluent: heptane) to obtain 72.5 g. of a crude 2,3-difluoro-1-iodo-4-(4-(trans-4-(trans-4-propylcyclohexyl)cyclohexyl)butyl)benzene.

Fourth Step

Under nitrogen gas stream, a solution prepared by dissolving 9.46 g (59.8 mmol) of 2,3-difluoro-1-ethoxybenzene in 100 ml of THF was cooled down to −70° C., and 59.8 ml of sec-butyl lithium (1.0M, cyclohexane solution) was added by drops thereto while being maintained at the same temperature and stirred at the same temperature for 2 hors. To the reaction mixture was added by drops 120 ml of zinc chloride (0.5M, THF solution), stirred at the same temperature for 1 hour, the reaction temperature was gradually raised up to room temperature, and they were stirred for further 1 hour. To the reaction mixture was added 1.00 g of tetrakis (triphenylphosphine)palladium (0), and a solution of 25.0 g (49.8 mmol) of the crude 2,3-difluoro-1-iodo-4-(4-(trans-4-(trans-4-propylcyclohexyl)cyclohexyl)butyl)benzene in 250 ml of THF was added by drops thereto and heated to reflux for 3 hours. The reaction mixture was added to 200 ml of water to terminate the reaction, the solvent was distilled off under a reduced pressure, and the concentrated residue was extracted with 500 ml of toluene. The organic layer was washed with 300 ml of water thrice and dried over anhydrous magnesium sulfate. The solvent was distilled off under a reduced pressure, and the residue was subjected to silica gel column chromatography (eluent: mixed solvent of heptane/toluene=7/3) to obtain a crude 1-ethoxy-2,3-difluoro-4-(2,3-difluoro-4-(4-(trans-4-(trans-4-propylcyclohexyl)cyclohexyl)butyl)phenyl)benzene. This crude product was recrystallized from heptane once and from mixed solvent of heptane/ethanol (5/1) once to obtain 13.1 g (yield 28.3%) of the subject compound.

Phase transition temperature: C 89.5 N 193.2 Iso; $^1$H-NMR: δ: (ppm): 0.40~2.10 (m, 36H), 2.70 (t, 2H, J=6.9 Hz), 4.17 (q, 2H, J=7.2 Hz), 6.60~7.20 (m, 4H); MS: m/e=532 ($M^+$).

Following the methods of Example 1 to 5, the following compounds can be prepared:

| | $R^1$ | 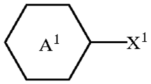 | 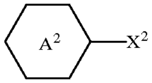 | 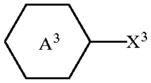 | m | n | $Y^1$ |
|---|---|---|---|---|---|---|---|
| 1 | $C_3H_7$ | 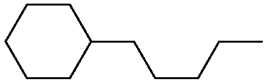 | | | 0 | 0 | $C_5H_{11}$ |
| 2 | $C_5H_{11}$ | 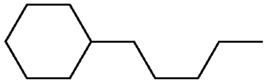 | | | 0 | 0 | $C_7H_{15}$ |
| 3 | $C_7H_{15}$ | 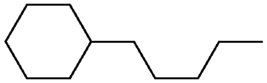 | | | 0 | 0 | $C_3H_7$ |
| 4 | $C_3H_7$ | 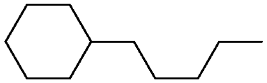 | | | 0 | 0 | $OC_2H_5$ |
| 5 | $C_5H_{11}O$ | 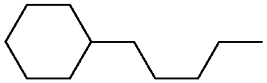 | | | 0 | 0 | $OC_4H_9$ |
| 6 | $C_5H_{11}$ | 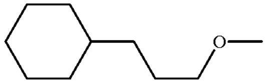 | | | 0 | 0 | $OC_2H_5$ |
| 7 | $C_3H_7$ | 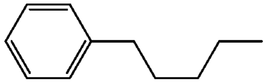 | | | 0 | 0 | $C_3H_7$ |
| 8 | $C_5H_{11}$ | 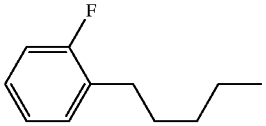 | | | 0 | 0 | $C_7H_{15}$ |

-continued
| | $R^1$ | 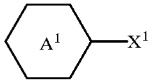 | 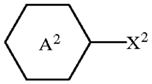 | 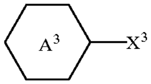 | m | n | $Y^1$ |
|---|---|---|---|---|---|---|---|
| 9 | $C_7H_{15}$ | 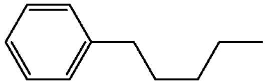 | | | 0 | 0 | $C_5H_{11}$ |
| 10 | 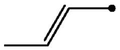 | 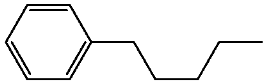 | | | 0 | 0 | $OC_4H_9$ |
| 11 | $C_5H_{11}$ | 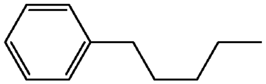 | | | 0 | 0 | $OC_2H_5$ |
| 12 | $C_7H_{15}$ | 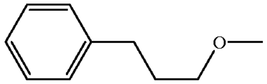 | | | 0 | 0 | $OCH_3$ |
| 13 | $C_3H_7$ | 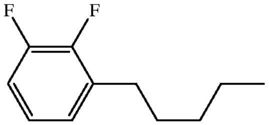 | | | 0 | 0 | $C_7H_{15}$ |
| 14 | $C_5H_{11}$ | 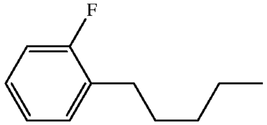 | | | 0 | 0 | $C_5H_{11}$ |
| 15 | $C_7H_{15}$ | 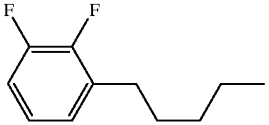 | | | 0 | 0 | $C_3H_7$ |

-continued
| | $R^1$ | 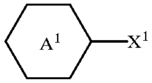 | 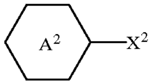 | 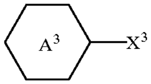 | m | n | $Y^1$ | |
|---|---|---|---|---|---|---|---|---|
| 16 | $C_3H_7$ | 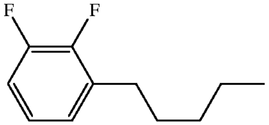 | | | 0 | 0 | $OC_2H_5$ | |
| 17 | $C_5H_{11}$ | 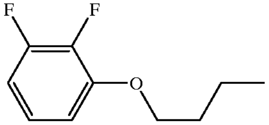 | | | 0 | 0 | $OC_4H_9$ | |
| 18 | $C_3H_7O$ | 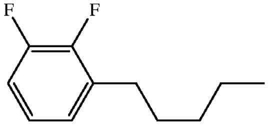 | | | 0 | 0 | $OC_5H_{11}$ | |
| 19 | $C_3H_7$ | 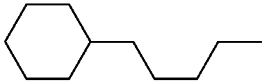 | 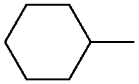 | | 1 | 0 | $C_5H_{11}$ | |
| 20 | $C_5H_{11}$ | 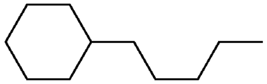 | 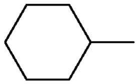 | | 1 | 0 | $C_3H_7$ | C 40.2 $S_B$ 90.9 N 98.0 Iso |
| 21 | $C_3H_7O$ | 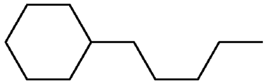 | 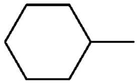 | | 1 | 0 | $C_7H_{15}$ | |
| 22 | $C_3H_7$ | 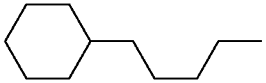 | 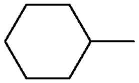 | | 1 | 0 | $OC_4H_9$ | |

-continued
| | $R^1$ | 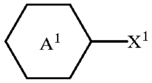 | 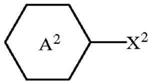 | 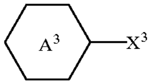 | m | n | $Y^1$ | |
|---|---|---|---|---|---|---|---|---|
| 23 | $C_5H_{11}$ | 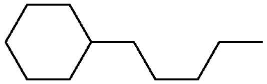 | 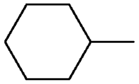 | | 1 | 0 | $OC_2H_5$ | C 79.2 $S_A$ 94.5 N 125.5 Iso |
| 24 | $C_7H_{15}$ | 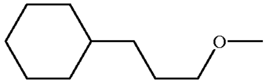 | 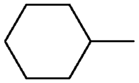 | | 1 | 0 | $OCH_3$ | |
| 25 | $C_3H_7$ | 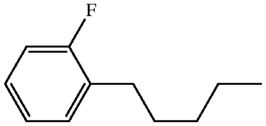 | 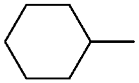 | | 1 | 0 | $C_7H_{15}$ | |
| 26 | $C_5H_{11}$ | 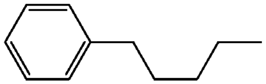 | 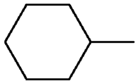 | | 1 | 0 | $C_5H_{11}$ | |
| 27 | $C_7H_{15}$ | 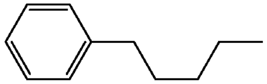 | 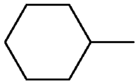 | | 1 | 0 | $C_3H_7$ | |
| 28 | $C_3H_7$ | 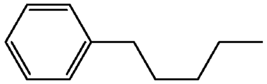 | 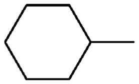 | | 1 | 0 | $OC_4H_9$ | |
| 29 | $C_5H_{11}$ | 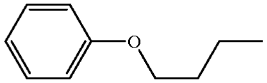 | 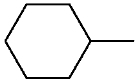 | | 1 | 0 | $OC_2H_5$ | |
| 30 | $C_5H_{11}O$ | 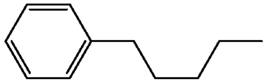 | 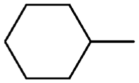 | | 1 | 0 | $OCH_3$ | |

-continued
| | $R^1$ | 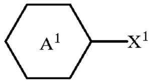 | 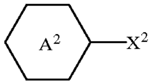 | 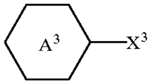 | m | n | $Y^1$ |
|---|---|---|---|---|---|---|---|
| 31 | $C_3H_7$ | 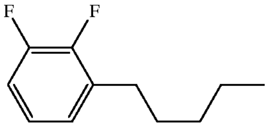 | 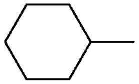 | | 1 | 0 | $C_5H_{11}$ |
| 32 | $C_5H_{11}$ | 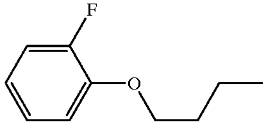 | 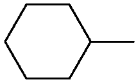 | | 1 | 0 | $C_3H_7$ |
| 33 | 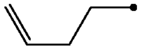 | 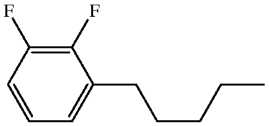 | 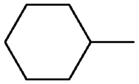 | | 1 | 0 | $CH_3$ |
| 34 | $C_3H_7$ | 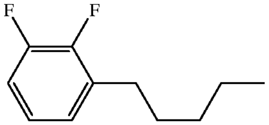 | 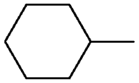 | | 1 | 0 | $OC_4H_9$ |
| 35 | $C_5H_{11}$ | 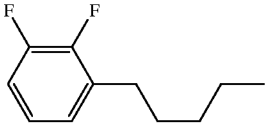 | 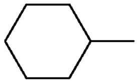 | | 1 | 0 | $OC_2H_5$ |
| 36 | $C_7H_{15}$ | 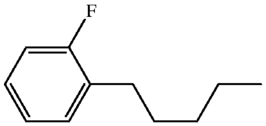 | 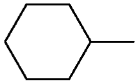 | | 1 | 0 | $OC_3H_7$ |

-continued
| | $R^1$ | 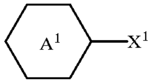 | 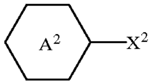 | 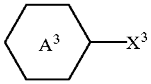 | m | n | $Y^1$ |
|---|---|---|---|---|---|---|---|
| 37 | $C_3H_7$ | 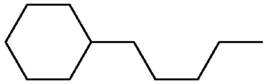 | 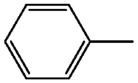 | | 1 | 0 | $C_3H_7$ |
| 38 | $C_5H_{11}$ | 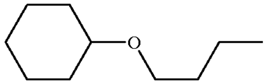 | 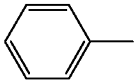 | | 1 | 0 | $C_5H_{11}$ |
| 39 | $C_2H_5$ | 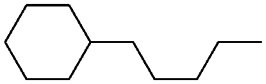 | 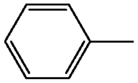 | | 1 | 0 | $C_5H_{11}$ |
| 40 | $C_3H_7$ | 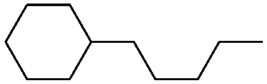 | 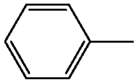 | | 1 | 0 | $OC_4H_9$ |
| 41 | $C_5H_{11}$ | 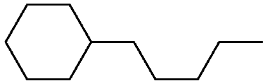 | 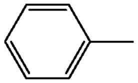 | | 1 | 0 | $OC_2H_5$ |
| 42 | $C_6H_{13}O$ | 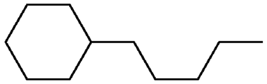 | 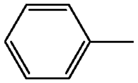 | | 1 | 0 | $OCH_3$ |
| 43 | $C_3H_7$ | 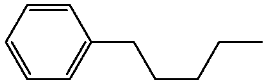 | 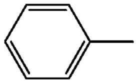 | | 1 | 0 | $C_5H_{11}$ |
| 44 | $C_5H_{11}$ | 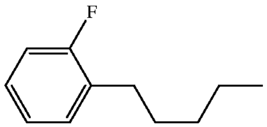 | 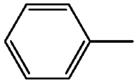 | | 1 | 0 | $C_3H_7$ |

-continued
| | R[1] | 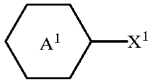 | 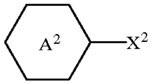 | 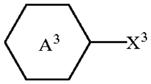 | m | n | $Y^1$ |
|---|---|---|---|---|---|---|---|
| 45 | $C_2H_5O$ | 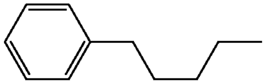 | 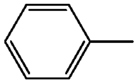 | | 1 | 0 | $C_7H_{15}$ |
| 46 | $C_3H_7$ | 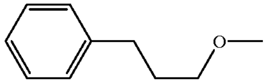 | 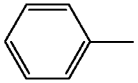 | | 1 | 0 | $OC_2H_5$ |
| 47 | $C_5H_{11}$ | 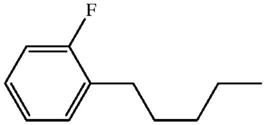 | 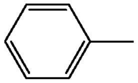 | | 1 | 0 | $OC_4H_9$ |
| 48 | $C_7H_{15}$ | 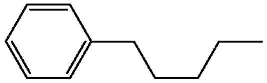 | 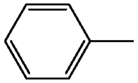 | | 1 | 0 | $OCH_3$ |
| 49 | $C_3H_7$ | 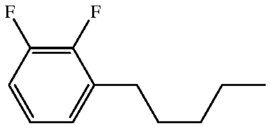 | 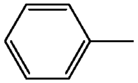 | | 1 | 0 | $C_3H_7$ |
| 50 | $C_5H_{11}$ | 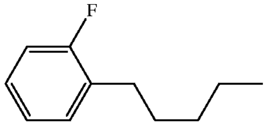 | 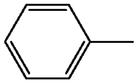 | | 1 | 0 | $C_5H_{11}$ |
| 51 | 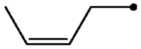 | 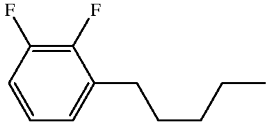 | 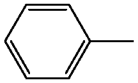 | | 1 | 0 | $C_2H_5$ |

-continued
| | $R^1$ | 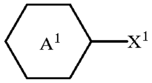 | 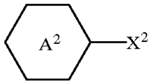 | 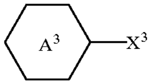 | m | n | $Y^1$ |
|---|---|---|---|---|---|---|---|
| 52 | $C_3H_7$ | 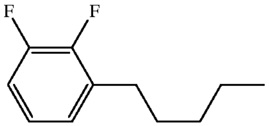 | 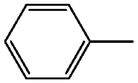 | | 1 | 0 | $OC_4H_9$ |
| 53 | $C_5H_{11}$ | 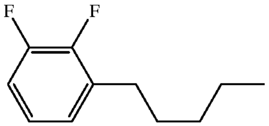 | 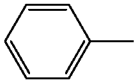 | | 1 | 0 | $OC_3H_7$ |
| 54 | $C_7H_{15}$ | 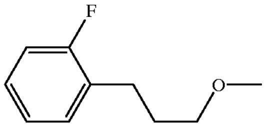 | 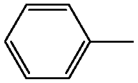 | | 1 | 0 | $OC_2H_5$ |
| 55 | $C_5H_{11}$ | 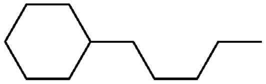 | 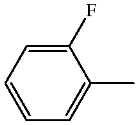 | | 1 | 0 | $C_3H_7$ |
| 56 | $C_3H_7$ | 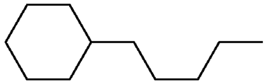 | 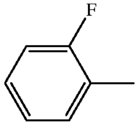 | | 1 | 0 | $C_5H_{11}$ |
| 57 | $C_5H_{11}O$ | 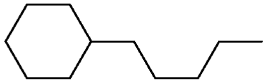 | 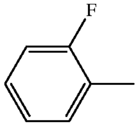 | | 1 | 0 | $C_3H_7$ |

-continued
| | $R^1$ | 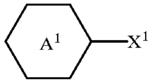 | 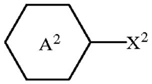 | 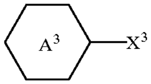 | m | n | $Y^1$ |
|---|---|---|---|---|---|---|---|
| 58 | $C_3H_7$ | 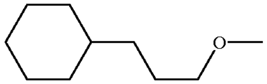 | 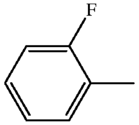 | | 1 | 0 | $OC_2H_5$ |
| 59 | $C_5H_{11}$ | 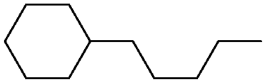 | 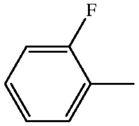 | | 1 | 0 | $OC_4H_9$ |
| 60 | 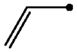 | 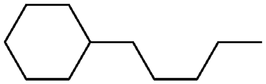 | 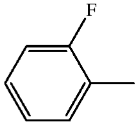 | | 1 | 0 | $OC_3H_7$ |
| 61 | $C_3H_7$ | 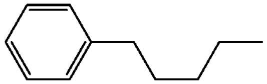 | 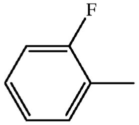 | | 1 | 0 | $C_7H_{15}$ |
| 62 | $C_5H_{11}$ | 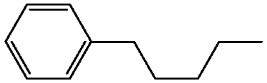 | 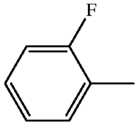 | | 1 | 0 | $C_3H_7$ |
| 63 | $C_7H_{15}$ | 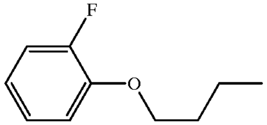 | 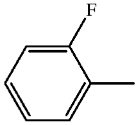 | | 1 | 0 | $C_5H_{11}$ |

-continued
| | R¹ | 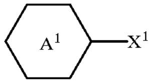 | 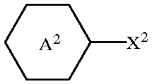 | 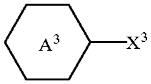 | m | n | $Y^1$ |
|---|---|---|---|---|---|---|---|
| 64 | $C_3H_7$ | 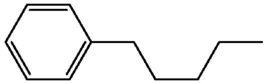 | 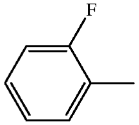 | | 1 | 0 | $OC_2H_5$ |
| 65 | $C_5H_{11}$ | 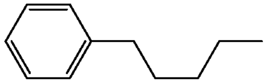 | 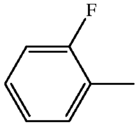 | | 1 | 0 | $OC_4H_9$ |
| 66 | 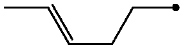 | 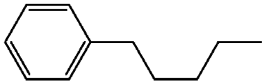 | 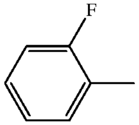 | | 1 | 0 | $OCH_3$ |
| 67 | $C_3H_7$ | 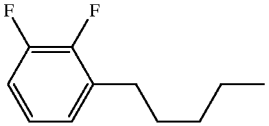 | 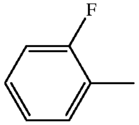 | | 1 | 0 | $C_5H_{11}$ |
| 68 | $C_5H_{11}$ | 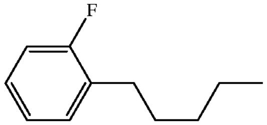 | 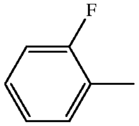 | | 1 | 0 | $C_3H_7$ |
| 69 | $C_7H_{15}$ | 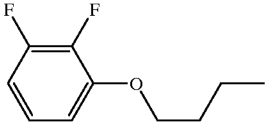 | 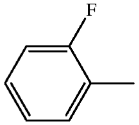 | | 1 | 0 | $C_2H_5$ |

-continued
| | $R^1$ | 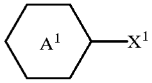 | 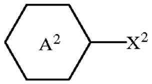 | 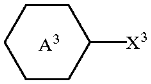 | m | n | $Y^1$ |
|---|---|---|---|---|---|---|---|
| 70 | $C_3H_7$ | 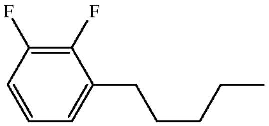 | 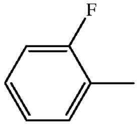 | | 1 | 0 | $OC_2H_9$ |
| 71 | $C_5H_{11}$ | 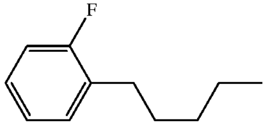 | 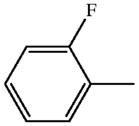 | | 1 | 0 | $OC_3H_7$ |
| 72 | $C_7H_{15}$ | 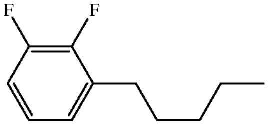 | 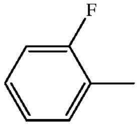 | | 1 | 0 | $OC_4H_9$ |
| 73 | $C_3H_7$ | 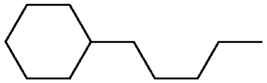 | 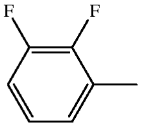 | | 1 | 0 | $C_3H_7$ |
| 74 | $C_5H_{11}$ | 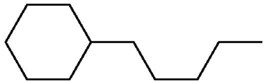 | 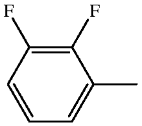 | | 1 | 0 | $C_5H_{11}$ |
| 75 | $C_5H_{11}$ | 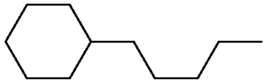 | 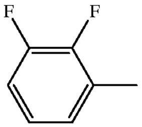 | | 1 | 0 | $C_3H_7$ |

-continued
| | $R^1$ | 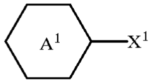 | 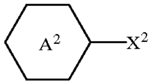 | 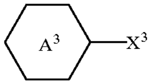 | m | n | $Y^1$ |
|---|---|---|---|---|---|---|---|
| 76 | $C_3H_7$ | 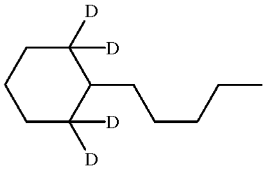 | 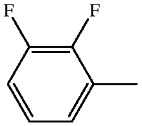 | | 1 | 0 | $OC_2H_5$ |
| 77 | $C_3H_7$ | 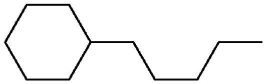 | 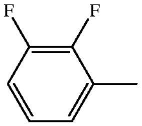 | | 1 | 0 | $OC_3H_7$ |
| 78 | $C_7H_{15}$ | 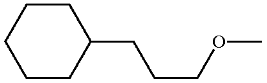 | 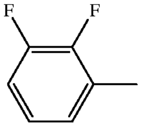 | | 1 | 0 | $OC_3H_7$ |
| 79 | $C_3H_7$ | 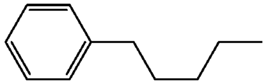 | 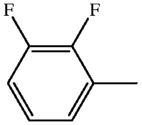 | | 1 | 0 | $C_5H_{11}$ |
| 80 | $C_5H_{11}$ | 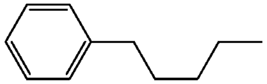 | 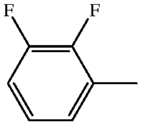 | | 1 | 0 | $C_3H_7$ |
| 81 | $C_7H_{15}$ | 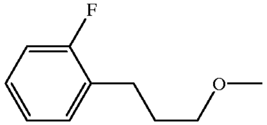 | 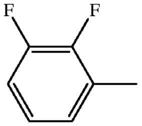 | | 1 | 0 | $C_5H_{11}$ |

-continued
| | $R^1$ | 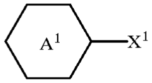 | 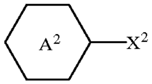 | 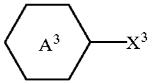 | m | n | $Y^1$ |
|---|---|---|---|---|---|---|---|
| 82 | $C_3H_7$ | 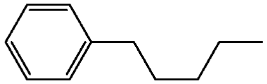 | 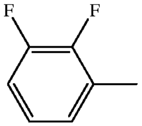 | | 1 | 0 | $OC_2H_5$ |
| 83 | $C_5H_{11}$ | 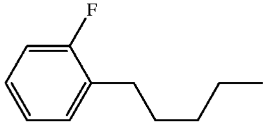 | 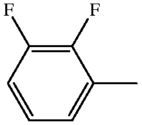 | | 1 | 0 | $OC_4H_9$ |
| 84 | 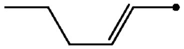 | 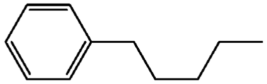 | 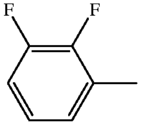 | | 1 | 0 | $OC_2H_5$ |
| 85 | $C_3H_7$ | 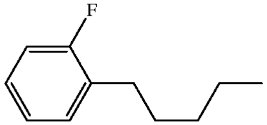 | 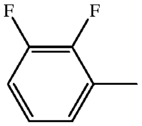 | | 1 | 0 | $C_3H_7$ |
| 86 | $C_5H_{11}$ | 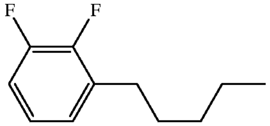 | 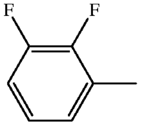 | | 1 | 0 | $C_5H_{11}$ |
| 87 | $C_5H_{11}$ | 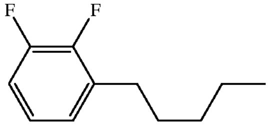 | 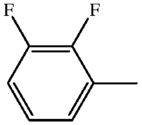 | | 1 | 0 | $C_3H_7$ |

-continued
| | $R^1$ | 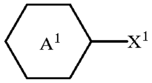 | 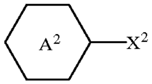 | 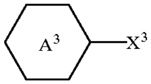 | m | n | $Y^1$ | |
|---|---|---|---|---|---|---|---|---|
| 88 | $C_3H_7$ | 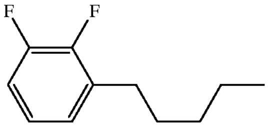 | 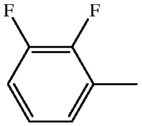 | | 1 | 0 | $OC_2H_5$ | |
| 89 | $C_5H_{11}$ | 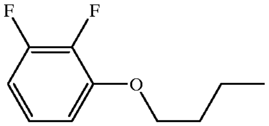 | 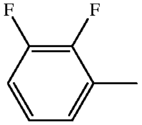 | | 1 | 0 | $OC_4H_9$ | |
| 90 | $C_7H_{15}$ | 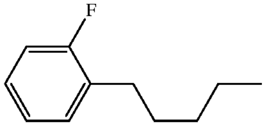 | 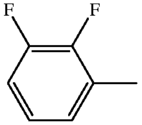 | | 1 | 0 | $OC_2H_5$ | |
| 91 | $C_3H_7$ | 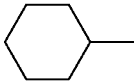 | 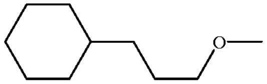 | | 1 | 0 | $C_3H_7$ | |
| 92 | $C_5H_{11}$ | 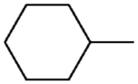 | 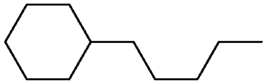 | | 1 | 0 | $C_3H_7$ | |
| 93 | 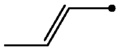 | 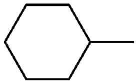 | 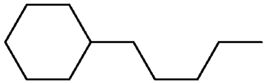 | | 1 | 0 | $C_5H_{11}$ | |
| 94 | $C_3H_7$ | 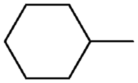 | 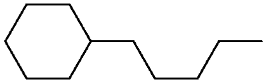 | | 1 | 0 | $OC_2H_5$ | C 44.4 $S_A$ 107.2 N 129.0 Iso |

-continued
| | $R^1$ | 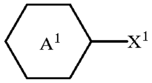 | 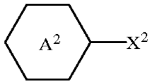 | 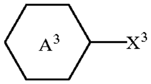 | m | n | $Y^1$ |
|---|---|---|---|---|---|---|---|
| 95 | $C_5H_{11}$ | 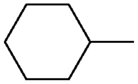 | 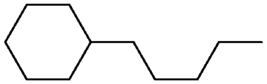 | | 1 | 0 | $OC_4H_9$ |
| 96 | $C_5H_{11}$ | 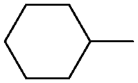 | 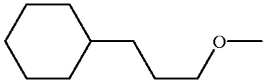 | | 1 | 0 | $OC_2H_5$ |
| 97 | $C_3H_7$ | 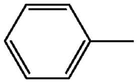 | 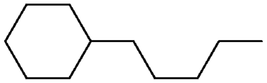 | | 1 | 0 | $C_3H_7$ |
| 98 | $C_5H_{11}O$ | 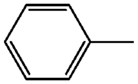 | 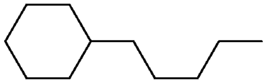 | | 1 | 0 | $C_5H_{11}$ |
| 99 | $C_7H_{15}$ | 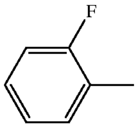 | 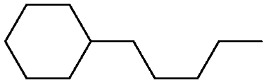 | | 1 | 0 | $C_7H_{15}$ |
| 100 | $C_3H_7$ | 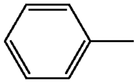 | 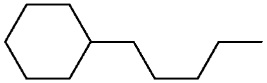 | | 1 | 0 | $OC_4H_9$ |
| 101 | $C_5H_{11}$ | 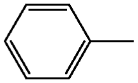 | 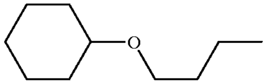 | | 1 | 0 | $OC_2H_5$ |
| 102 | $C_5H_{11}$ | 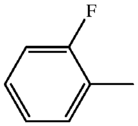 | 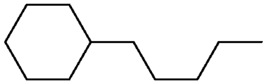 | | 1 | 0 | $OC_3H_7$ |

-continued
| | R¹ | 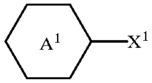 | 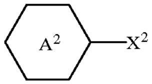 | 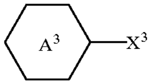 | m | n | Y¹ |
|---|---|---|---|---|---|---|---|
| 103 | $C_3H_7$ | 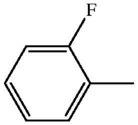 | 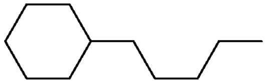 | | 1 | 0 | $C_5H_{11}$ |
| 104 | $C_5H_{11}$ | 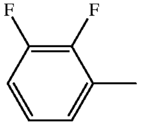 | 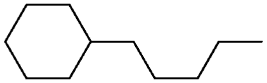 | | 1 | 0 | $C_3H_7$ |
| 105 | $C_7H_{15}$ | 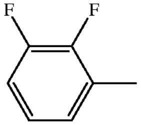 | 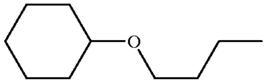 | | 1 | 0 | $CH_3$ |
| 106 | $C_3H_7$ | 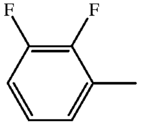 | 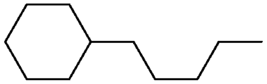 | | 1 | 0 | $OC_2H_5$ |
| 107 | $C_5H_{11}$ | 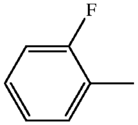 | 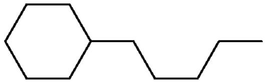 | | 1 | 0 | $OC_4H_9$ |
| 108 | $C_2H_5O$ | 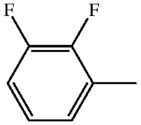 | 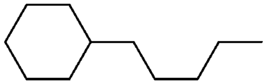 | | 1 | 0 | $OCH_3$ |

-continued
| | $R^1$ | 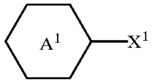 | 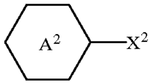 | 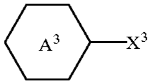 | m | n | $Y^1$ |
|---|---|---|---|---|---|---|---|
| 109 | $C_3H_7$ | 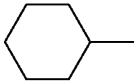 | 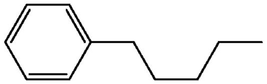 | | 1 | 0 | $C_3H_7$ |
| 110 | $C_5H_{11}$ | 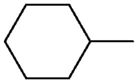 | 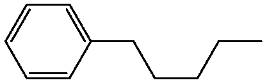 | | 1 | 0 | $C_5H_{11}$ |
| 111 | $C_5H_{11}$ | 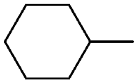 | 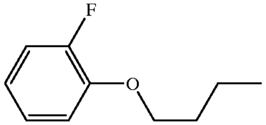 | | 1 | 0 | $C_3H_7$ |
| 112 | $C_3H_7O$ | 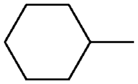 | 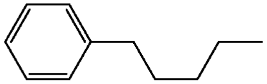 | | 1 | 0 | $OC_4H_9$ |
| 113 | $C_5H_{11}$ | 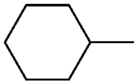 | 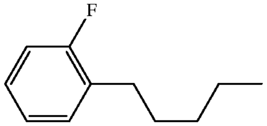 | | 1 | 0 | $OC_2H_5$ |
| 114 | $C_7H_{15}$ | 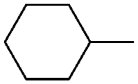 | 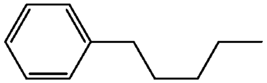 | | 1 | 0 | $OCH_3$ |
| 115 | $C_3H_7$ | 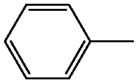 | 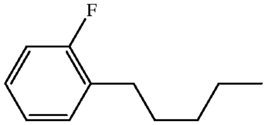 | | 1 | 0 | $C_7H_{15}$ |

-continued
| | $R^1$ | 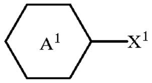 | 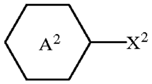 | 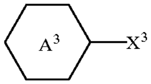 | m | n | $Y^1$ |
|---|---|---|---|---|---|---|---|
| 116 | $C_5H_{11}$ | 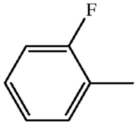 | 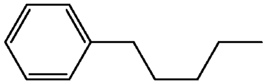 | | 1 | 0 | $C_3H_7$ |
| 117 | 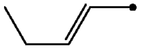 | 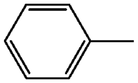 | 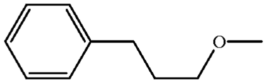 | | 1 | 0 | $C_5H_{11}$ |
| 118 | $C_3H_7$ | 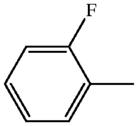 | 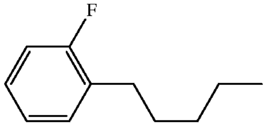 | | 1 | 0 | $OC_2H_5$ |
| 119 | $C_5H_{11}O$ | 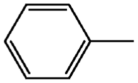 | 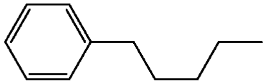 | | 1 | 0 | $OC_4H_9$ |
| 120 | $C_5H_{11}$ | 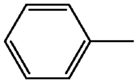 | 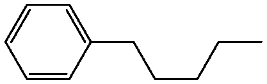 | | 1 | 0 | $OC_3H_7$ |
| 121 | $C_3H_7$ | 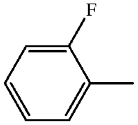 | 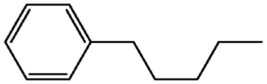 | | 1 | 0 | $C_5H_{11}$ |
| 122 | $C_5H_{11}$ | 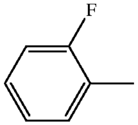 | 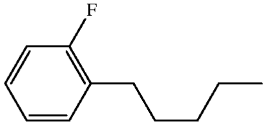 | | 1 | 0 | $C_3H_7$ |

-continued
| | $R^1$ | 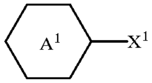 | 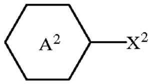 | 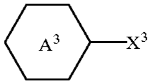 | m | n | $Y^1$ |
|---|---|---|---|---|---|---|---|
| 123 | $C_7H_{15}$ | 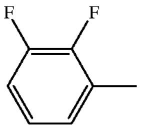 | 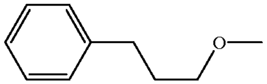 | | 1 | 0 | $C_2H_5$ |
| 124 | 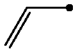 | 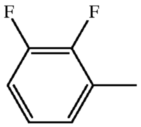 | 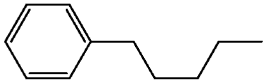 | | 1 | 0 | $OC_2H_5$ |
| 125 | $C_5H_{11}$ | 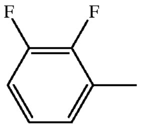 | 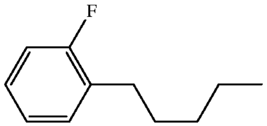 | | 1 | 0 | $OC_4H_9$ |
| 126 | $C_7H_{15}$ | 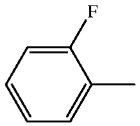 | 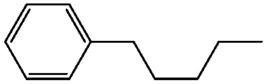 | | 1 | 0 | $OC_3H_7$ |
| 127 | $C_3H_7$ | 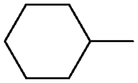 | 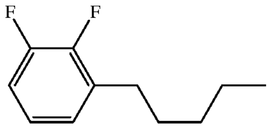 | | 1 | 0 | $C_4H_9$ |
| 128 | $C_5H_{11}$ | 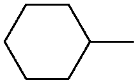 | 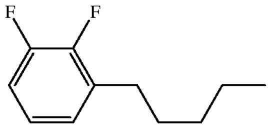 | | 1 | 0 | $C_3H_7$ |

-continued
| | $R^1$ | 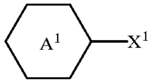 | 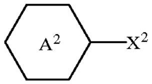 | 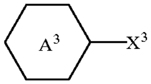 | m | n | $Y^1$ |
|---|---|---|---|---|---|---|---|
| 129 | $C_5H_{11}O$ | 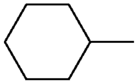 | 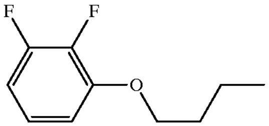 | | 1 | 0 | $C_5H_{11}$ |
| 130 | $C_5H_{11}$ | 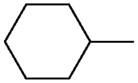 | 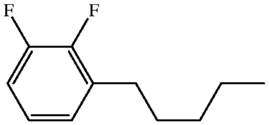 | | 1 | 0 | $OC_4H_9$ |
| 131 | $C_5H_{11}$ | 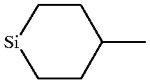 | 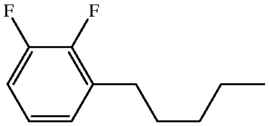 | | 1 | 0 | $OC_2H_5$ |
| 132 | $C_7H_{15}$ | 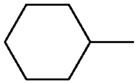 | 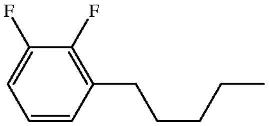 | | 1 | 0 | $OCH_3$ |
| 133 | $C_3H_7$ | 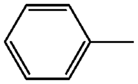 | 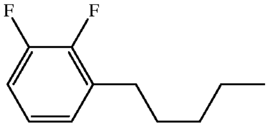 | | 1 | 0 | $C_3H_7$ |
| 134 | $C_5H_{11}$ | 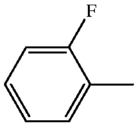 | 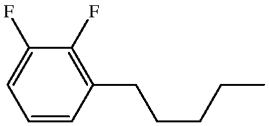 | | 1 | 0 | $C_2H_5$ |

-continued
| | $R^1$ | 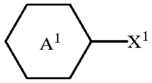 | 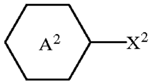 | 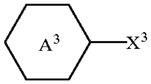 | m | n | $Y^1$ |
|---|---|---|---|---|---|---|---|
| 135 | $C_7H_{15}$ | 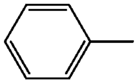 | 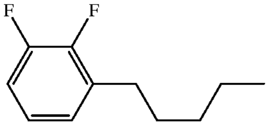 | | 1 | 0 | $C_5H_{11}$ |
| 136 | $C_3H_7$ | 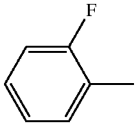 | 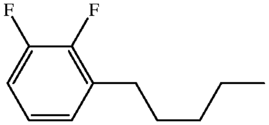 | | 1 | 0 | $OC_2H_5$ |
| 137 | $C_5H_{11}$ | 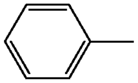 | 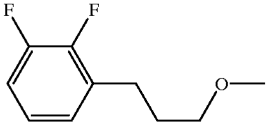 | | 1 | 0 | $OC_4H_9$ |
| 138 | $C_5H_{11}$ | 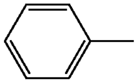 | 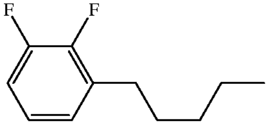 | | 1 | 0 | $OC_3H_7$ |
| 139 | $C_3H_7$ | 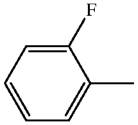 | 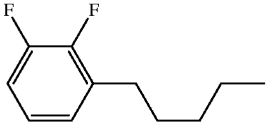 | | 1 | 0 | $C_5H_{11}$ |
| 140 | 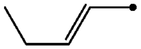 | 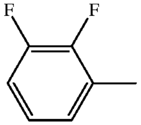 | 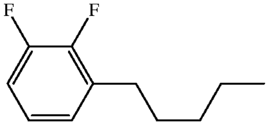 | | 1 | 0 | $C_3H_7$ |

-continued
| | $R^1$ | 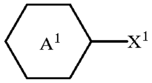 | 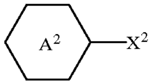 | 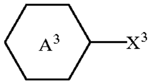 | m | n | $Y^1$ |
|---|---|---|---|---|---|---|---|
| 141 | $C_3H_7O$ | 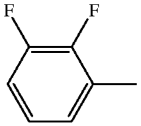 | 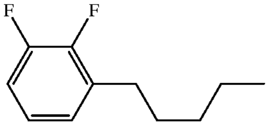 | | 1 | 0 | $C_7H_{15}$ |
| 142 | $C_3H_7$ | 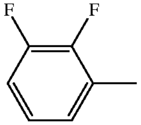 | 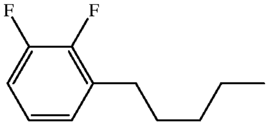 | | 1 | 0 | $OC_2H_5$ |
| 143 | $C_5H_{11}$ | 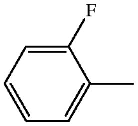 | 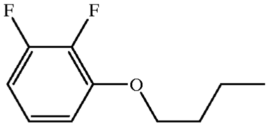 | | 1 | 0 | $OC_3H_7$ |
| 144 | $C_7H_{15}$ | 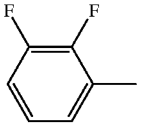 | 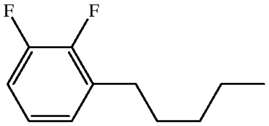 | | 1 | 0 | $OC_4H_9$ |
| 145 | $C_3H_7$ | 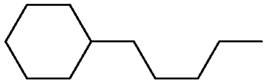 | 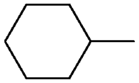 | 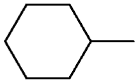 | 1 | 1 | $C_5H_{11}$ |
| 146 | $C_5H_{11}$ | 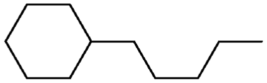 | 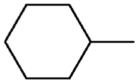 | 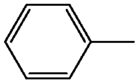 | 1 | 1 | $C_3H_7$ |
| 147 | $C_3H_7O$ | 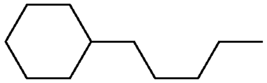 | 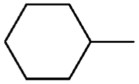 | 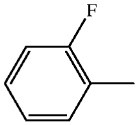 | 1 | 1 | $C_7H_{15}$ |

-continued
| | $R^1$ | 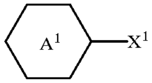 | 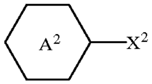 | 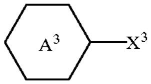 | m | n | $Y^1$ |
|---|---|---|---|---|---|---|---|
| 148 | $C_3H_7$ | 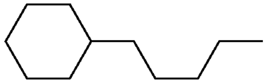 | 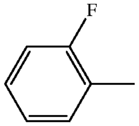 | 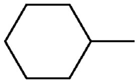 | 1 | 1 | $OC_4H_9$ |
| 149 | $C_5H_{11}$ | 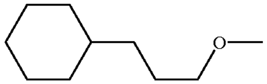 | 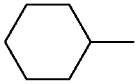 | 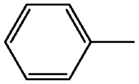 | 1 | 1 | $OC_2H_5$ |
| 150 | 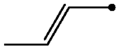 | 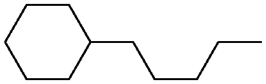 | 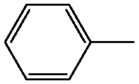 | 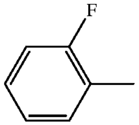 | 1 | 1 | $OCH_3$ |
| 151 | $C_3H_7$ | 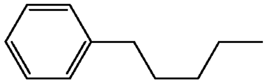 | 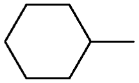 | 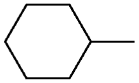 | 1 | 1 | $C_7H_{15}$ |
| 152 | $C_5H_{11}$ | 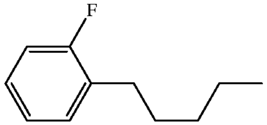 | 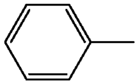 | 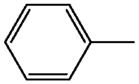 | 1 | 1 | $C_5H_{11}$ |
| 153 | $C_7H_{15}$ | 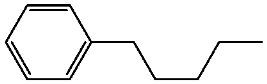 | 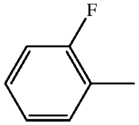 | 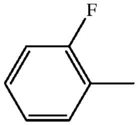 | 1 | 1 | $C_3H_7$ |

-continued
| | R¹ | 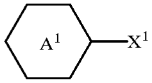 | 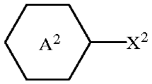 | 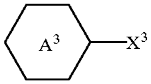 | m | n | Y¹ |
|---|---|---|---|---|---|---|---|
| 154 | $C_3H_7$ | 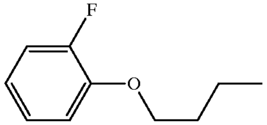 | 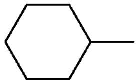 | 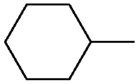 | 1 | 1 | $OC_4H_9$ |
| 155 | $C_5H_{11}$ | 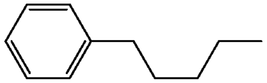 | 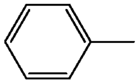 | 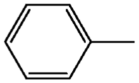 | 1 | 1 | $OC_2H_5$ |
| 156 | $C_7H_{15}$ | 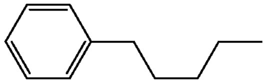 | 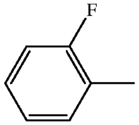 | 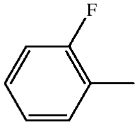 | 1 | 1 | $OCH_3$ |
| 157 | $C_3H_7$ | 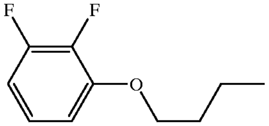 | 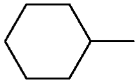 | 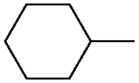 | 1 | 1 | $C_2H_5$ |
| 158 | $C_5H_{11}$ | 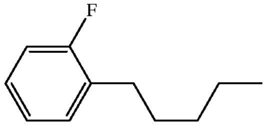 | 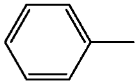 | 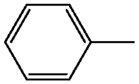 | 1 | 1 | $C_3H_7$ |
| 159 | $C_5H_{11}O$ | 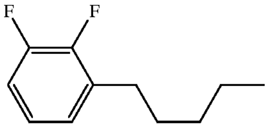 | 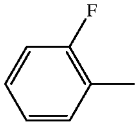 | 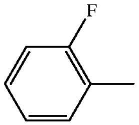 | 1 | 1 | $C_5H_{11}$ |

-continued
| | $R^1$ | 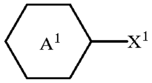 | 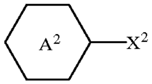 | 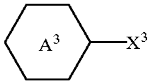 | m | n | $Y^1$ |
|---|---|---|---|---|---|---|---|
| 160 | $C_3H_7$ | 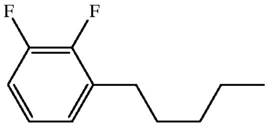 | 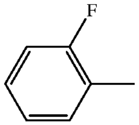 | 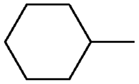 | 1 | 1 | $OC_2H_5$ |
| 161 | $C_5H_{11}$ | 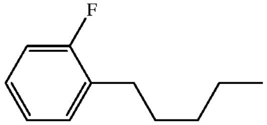 | 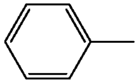 | 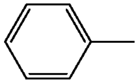 | 1 | 1 | $OC_4H_9$ |
| 162 | $C_7H_{15}$ | 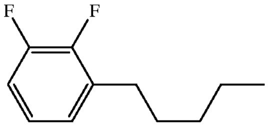 | 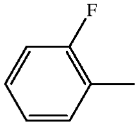 | 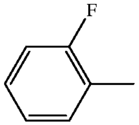 | 1 | 1 | $OC_3H_7$ |
| 163 | $C_3H_7$ | 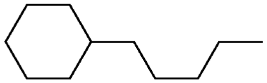 | 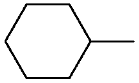 | 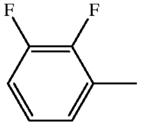 | 1 | 1 | $C_3H_7$ |
| 164 | $C_5H_{11}$ | 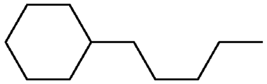 | 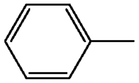 | 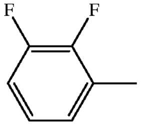 | 1 | 1 | $C_5H_{11}$ |
| 165 | $C_3H_7$ | 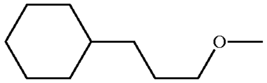 | 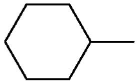 | 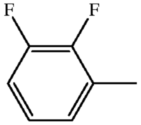 | 1 | 1 | $C_7H_{15}$ |

-continued
| | $R^1$ | 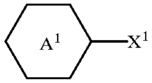 | 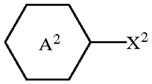 | 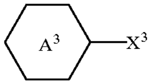 | m | n | $Y^1$ |
|---|---|---|---|---|---|---|---|
| 166 | 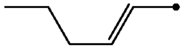 | 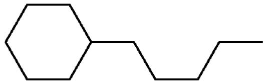 | 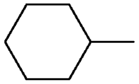 | 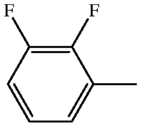 | 1 | 1 | $OCH_3$ |
| 167 | $C_5H_{11}$ | 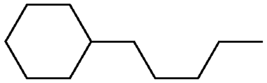 | 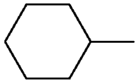 | 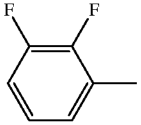 | 1 | 1 | $OC_2H_5$ |
| 168 | $C_7H_{15}$ | 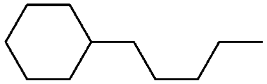 | 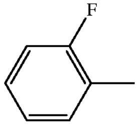 | 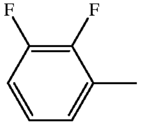 | 1 | 1 | $OC_3H_7$ |
| 169 | $C_3H_7$ | 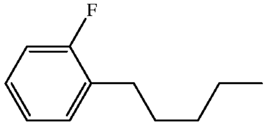 | 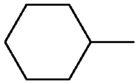 | 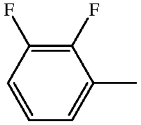 | 1 | 1 | $C_7H_{15}$ |
| 170 | $C_5H_{11}$ | 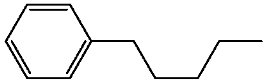 | 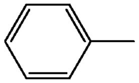 | 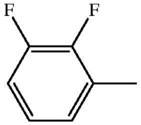 | 1 | 1 | $C_5H_{11}$ |
| 171 | $C_7H_{15}$ | 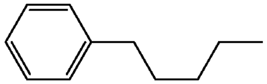 | 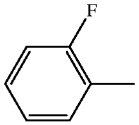 | 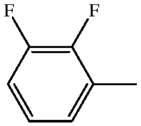 | 1 | 1 | $C_3H_7$ |

-continued
| | R¹ | 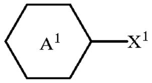 | 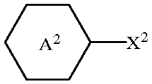 | 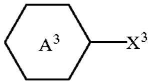 | m | n | Y¹ |
|---|---|---|---|---|---|---|---|
| 172 | $C_3H_7$ | 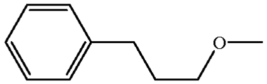 | 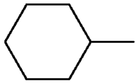 | 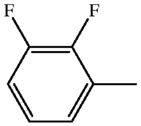 | 1 | 1 | $OC_4H_9$ |
| 173 | $C_5H_{11}O$ | 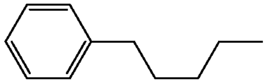 | 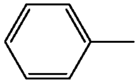 | 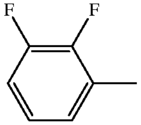 | 1 | 1 | $OC_2H_5$ |
| 174 | $C_7H_{15}$ | 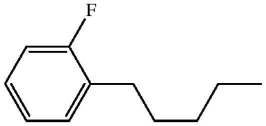 | 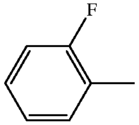 | 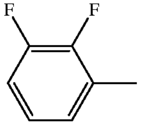 | 1 | 1 | $OC_3H_7$ |
| 175 | $C_3H_7O$ | 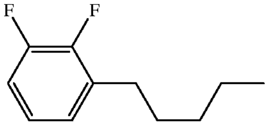 | 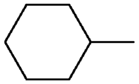 | 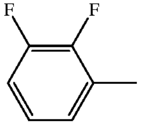 | 1 | 1 | $C_2H_5$ |
| 176 | $C_5H_{11}$ | 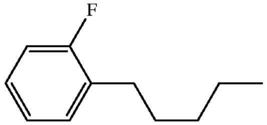 | 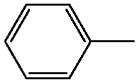 | 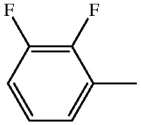 | 1 | 1 | $C_3H_7$ |
| 177 | $C_5H_{11}$ | 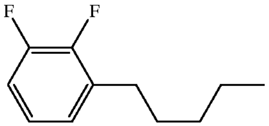 | 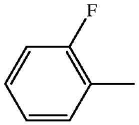 | 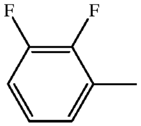 | 1 | 1 | $C_5H_{11}$ |

-continued
| | $R^1$ | 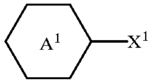 | 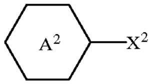 | 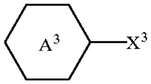 | m | n | $Y^1$ |
|---|---|---|---|---|---|---|---|
| 178 | $C_3H_7$ | 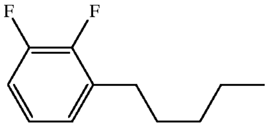 | 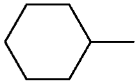 | 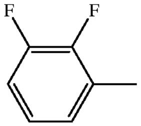 | 1 | 1 | $OC_2H_5$ |
| 179 | $C_5H_{11}$ | 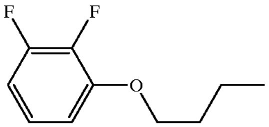 | 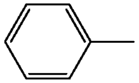 | 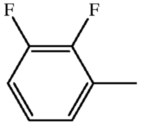 | 1 | 1 | $OC_3H_7$ |
| 180 | $C_3H_7O$ | 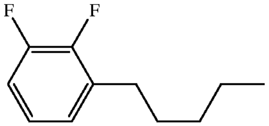 | 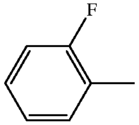 | 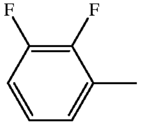 | 1 | 1 | $OC_4H_9$ |
| 181 | $C_3H_7$ | 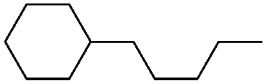 | 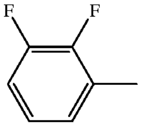 | 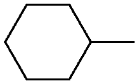 | 1 | 1 | $C_3H_7$ |
| 182 | $C_5H_{11}$ | 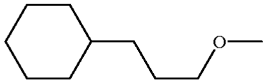 | 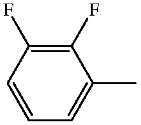 | 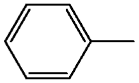 | 1 | 1 | $C_7H_{15}$ |
| 183 | 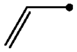 | 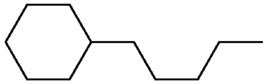 | 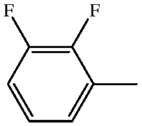 | 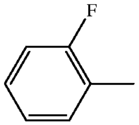 | 1 | 1 | $C_5H_{11}$ |

-continued
| | $R^1$ | 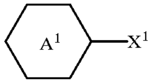 | 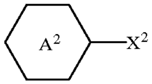 | 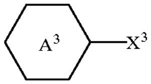 | m | n | $Y^1$ |
|---|---|---|---|---|---|---|---|
| 184 | $C_3H_7O$ | 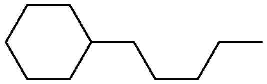 | 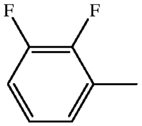 | 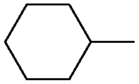 | 1 | 1 | $OCH_3$ |
| 185 | $C_5H_{11}$ | 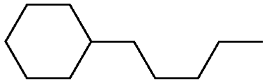 | 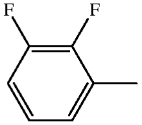 | 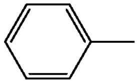 | 1 | 1 | $OC_2H_5$ |
| 186 | $C_7H_{15}$ | 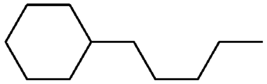 | 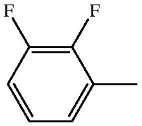 | 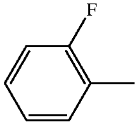 | 1 | 1 | $OC_3H_7$ |
| 187 | $C_3H_7$ | 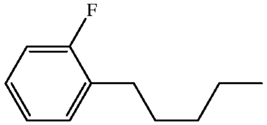 | 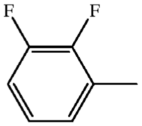 | 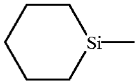 | 1 | 1 | $C_7H_{15}$ |
| 188 | $C_5H_{11}$ | 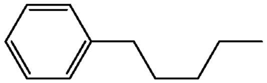 | 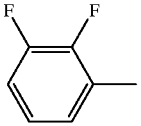 | 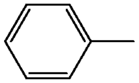 | 1 | 1 | $C_5H_{11}$ |
| 189 | $C_7H_{15}$ | 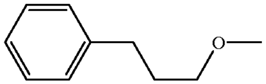 | 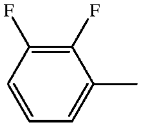 | 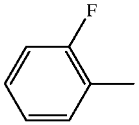 | 1 | 1 | $C_3H_7$ |

-continued
| | R¹ | 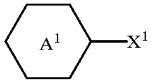 | 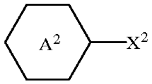 | 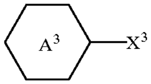 | m | n | $Y^1$ |
|---|---|---|---|---|---|---|---|
| 190 | $C_3H_7$ | 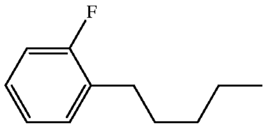 | 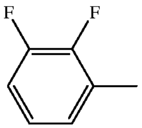 | 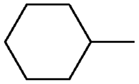 | 1 | 1 | $OC_4H_9$ |
| 191 | $C_5H_{11}$ | 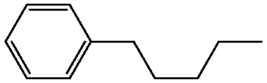 | 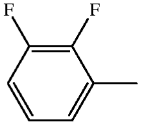 | 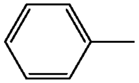 | 1 | 1 | $OC_2H_5$ |
| 192 | $C_7H_{15}$ | 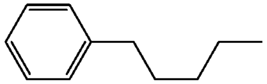 | 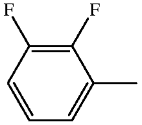 | 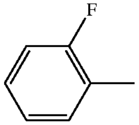 | 1 | 1 | $OC_3H_7$ |
| 193 | $C_3H_7$ | 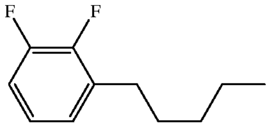 | 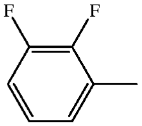 | 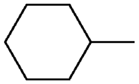 | 1 | 1 | $C_2H_5$ |
| 194 | $C_5H_{11}O$ | 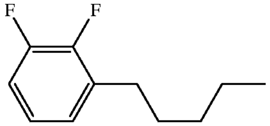 | 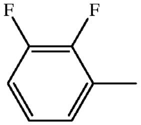 | 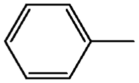 | 1 | 1 | $C_3H_7$ |
| 195 | $C_5H_{11}$ | 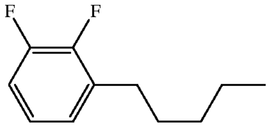 | 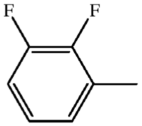 | 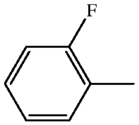 | 1 | 1 | $C_5H_{11}$ |

-continued
| | $R^1$ | 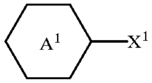 | 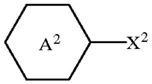 | 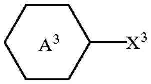 | m | n | $Y^1$ |
|---|---|---|---|---|---|---|---|
| 196 | $C_3H_7$ | 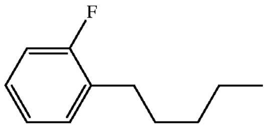 | 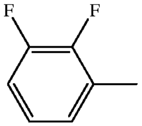 | 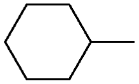 | 1 | 1 | $OC_2H_5$ |
| 197 | $C_5H_{11}$ | 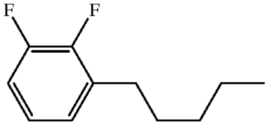 | 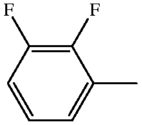 | 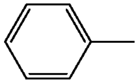 | 1 | 1 | $OC_3H_7$ |
| 198 | $C_3H_7O$ | 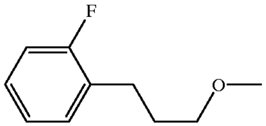 | 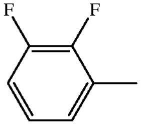 | 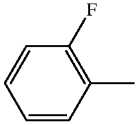 | 1 | 1 | $OC_4H_9$ |
| 199 | $C_3H_7$ | 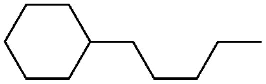 | 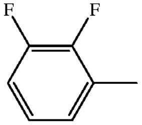 | 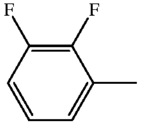 | 1 | 1 | $C_7H_{15}$ |
| 200 | $C_5H_{11}$ | 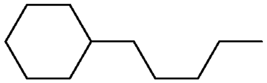 | 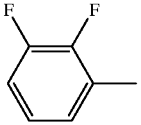 | 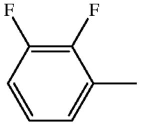 | 1 | 1 | $C_3H_7$ |
| 201 | 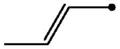 | 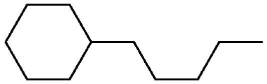 | 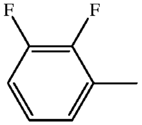 | 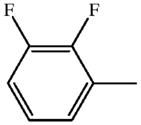 | 1 | 1 | $C_5H_{11}$ |

-continued
| | $R^1$ | 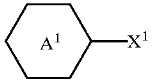 | 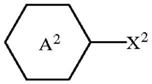 | 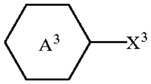 | m | n | $Y^1$ |
|---|---|---|---|---|---|---|---|
| 202 | $C_3H_7$ | 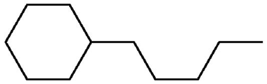 | 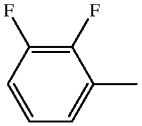 | 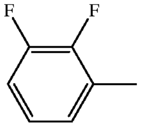 | 1 | 1 | $OC_3H_7$ |
| 203 | $C_5H_{11}$ | 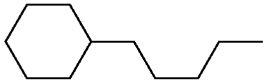 | 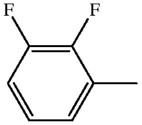 | 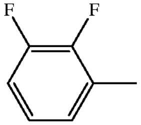 | 1 | 1 | $OC_2H_5$ |
| 204 | $C_7H_{15}$ | 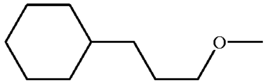 | 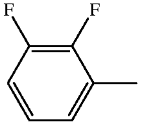 | 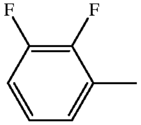 | 1 | 1 | $OC_4H_9$ |
| 205 | $C_3H_7$ | 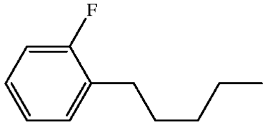 | 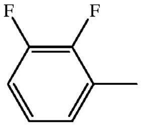 | 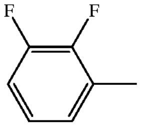 | 1 | 1 | $C_7H_{15}$ |
| 206 | $C_5H_{11}O$ | 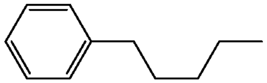 | 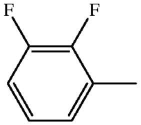 | 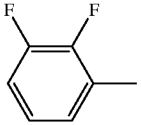 | 1 | 1 | $C_5H_{11}$ |
| 207 | $C_7H_{15}$ | 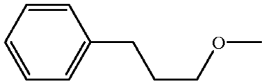 | 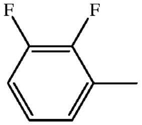 | 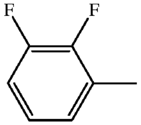 | 1 | 1 | $C_3H_7$ |

-continued
| | R¹ | | | | m | n | Y¹ |
|---|---|---|---|---|---|---|---|
| | $R^1$ | 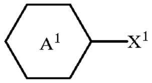 | 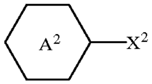 | 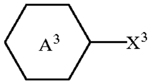 | m | n | $Y^1$ |
| 208 | $C_3H_7$ | 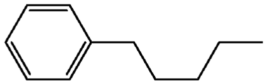 | 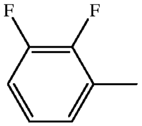 | 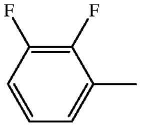 | 1 | 1 | $OC_2H_5$ |
| 209 | $C_5H_{11}$ | 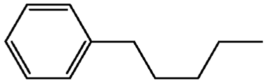 | 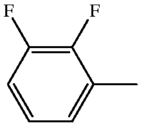 | 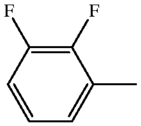 | 1 | 1 | $OCH_3$ |
| 210 | $C_7H_{15}$ | 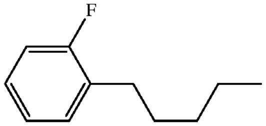 | 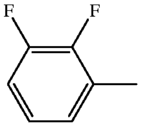 | 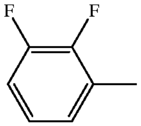 | 1 | 1 | $OC_3H_7$ |
| 211 | $C_3H_7$ | 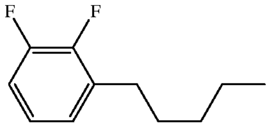 | 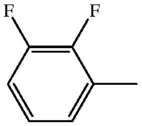 | 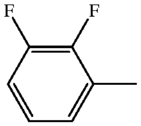 | 1 | 1 | $C_2H_5$ |
| 212 | $C_5H_{11}$ | 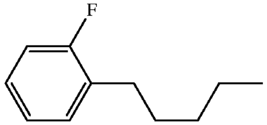 | 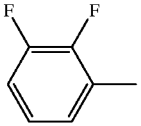 | 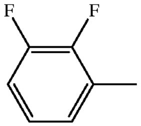 | 1 | 1 | $C_3H_7$ |
| 213 | $C_3H_7O$ | 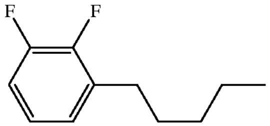 | 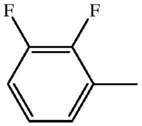 | 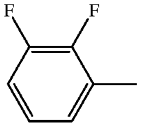 | 1 | 1 | $C_5H_{11}$ |

-continued
| | $R^1$ | 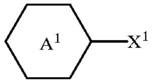 | 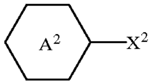 | 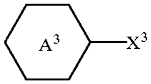 | m | n | $Y^1$ |
|---|---|---|---|---|---|---|---|
| 214 | $C_5H_{11}$ | 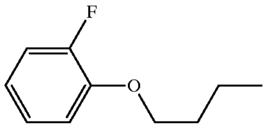 | 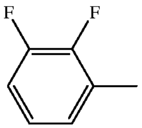 | 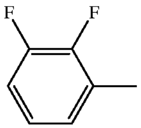 | 1 | 1 | $OC_2H_5$ |
| 215 | $C_5H_{11}$ | 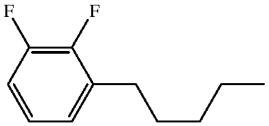 | 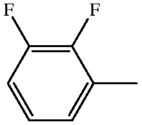 | 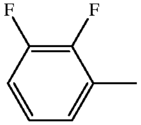 | 1 | 1 | $OC_4H_9$ |
| 216 | $C_3H_7O$ | 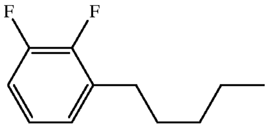 | 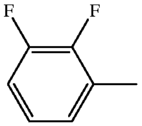 | 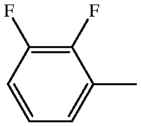 | 1 | 1 | $OC_3H_7$ |
| 217 | $C_3H_7$ | 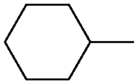 | 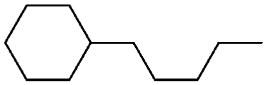 | 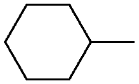 | 1 | 1 | $C_3H_7$ |
| 218 | $C_5H_{11}$ | 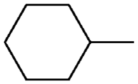 | 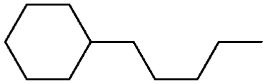 | 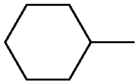 | 1 | 1 | $C_3H_7$ |
| 219 | 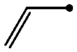 | 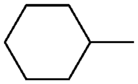 | 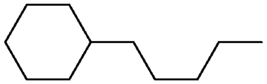 | 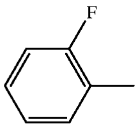 | 1 | 1 | $C_5H_{11}$ |
| 220 | $C_5H_{11}$ | 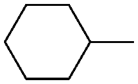 | 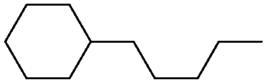 | 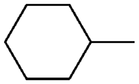 | 1 | 1 | $OC_2H_5$ |

-continued
| | $R^1$ | 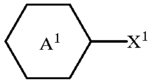 | 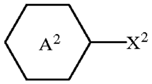 | 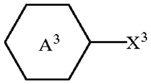 | m | n | $Y^1$ |
|---|---|---|---|---|---|---|---|
| 221 | $C_5H_{11}$ | 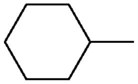 | 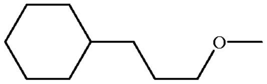 | 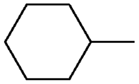 | 1 | 1 | $OC_3H_7$ |
| 222 | $C_5H_{11}$ | 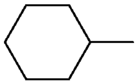 | 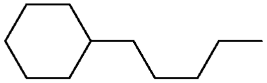 | 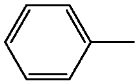 | 1 | 1 | $OC_4H_9$ |
| 223 | $C_3H_7$ | 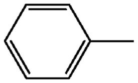 | 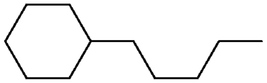 | 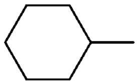 | 1 | 1 | $C_3H_7$ |
| 224 | $C_5H_{11}O$ | 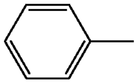 | 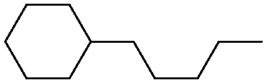 | 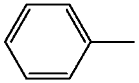 | 1 | 1 | $C_5H_{11}$ |
| 225 | $C_7H_{15}$ | 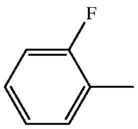 | 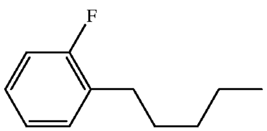 | 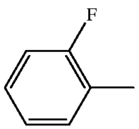 | 1 | 1 | $C_7H_{15}$ |
| 226 | $C_3H_7$ | 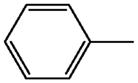 | 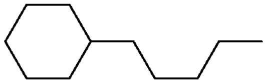 | 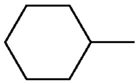 | 1 | 1 | $OC_4H_9$ |
| 227 | $C_5H_{11}$ | 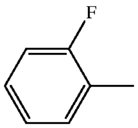 | 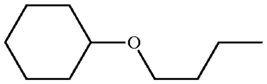 | 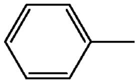 | 1 | 1 | $OC_2H_5$ |

-continued
| | R¹ | 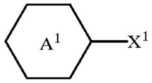 | 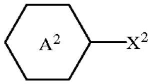 | 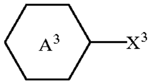 | m | n | Y¹ |
|---|---|---|---|---|---|---|---|
| 228 | $C_5H_{11}$ | 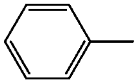 | 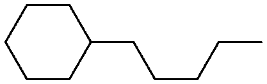 | 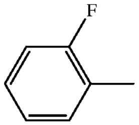 | 1 | 1 | $OC_3H_7$ |
| 229 | $C_3H_7$ | 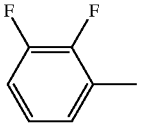 | 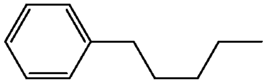 | 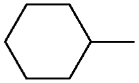 | 1 | 1 | $C_5H_{11}$ |
| 230 | $C_5H_{11}O$ | 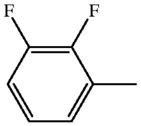 | 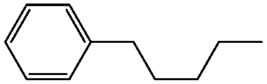 | 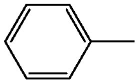 | 1 | 1 | $C_3H_7$ |
| 231 | $C_7H_{15}$ | 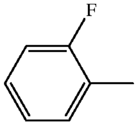 | 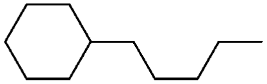 | 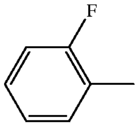 | 1 | 1 | $CH_3$ |
| 232 | $C_3H_7$ | 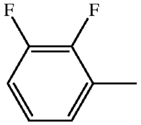 | 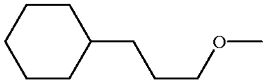 | 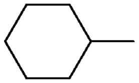 | 1 | 1 | $OC_2H_5$ |
| 233 | $C_5H_{11}$ | 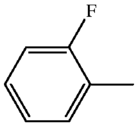 | 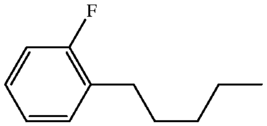 | 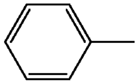 | 1 | 1 | $OC_4H_9$ |

-continued
| | $R^1$ | 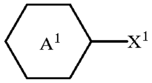 | 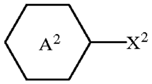 | 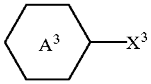 | m | n | $Y^1$ | |
|---|---|---|---|---|---|---|---|---|
| 234 | $C_2H_5O$ | 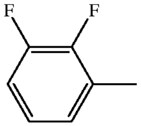 | 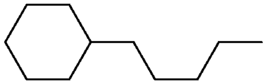 | 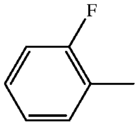 | 1 | 1 | $OCH_3$ | |
| 235 | $C_3H_7$ | 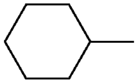 | 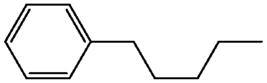 | 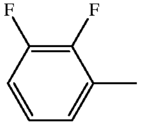 | 1 | 1 | $C_3H_7$ | |
| 236 | $C_5H_{11}$ | 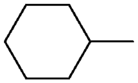 | 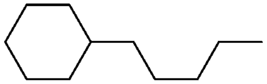 | 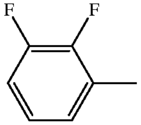 | 1 | 1 | $C_3H_7$ | |
| 237 | $C_3H_7$ | 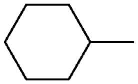 | 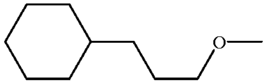 | 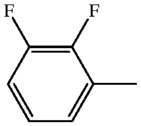 | 1 | 1 | $C_5H_{11}$ | |
| 238 | $C_3H_7$ | 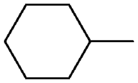 | 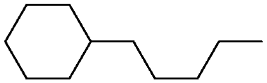 | 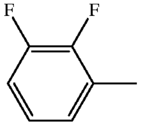 | 1 | 1 | $OC_2H_5$ | C 89.5 N 193.2 Iso |
| 239 | $C_5H_{11}$ | 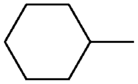 | 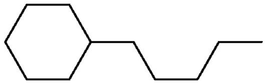 | 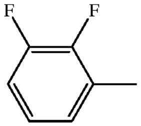 | 1 | 1 | $OC_3H_7$ | |

-continued
| | $R^1$ | 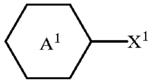 | 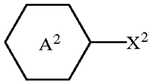 | 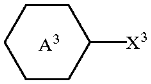 | m | n | $Y^1$ |
|---|---|---|---|---|---|---|---|
| 240 | 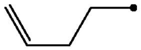 | 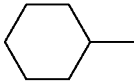 | 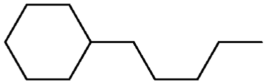 | 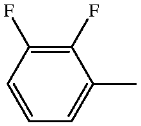 | 1 | 1 | $OC_4H_9$ |
| 241 | $C_3H_7$ | 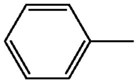 | 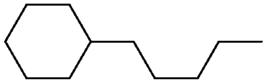 | 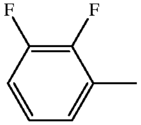 | 1 | 1 | $C_3H_7$ |
| 242 | $C_5H_{11}O$ | 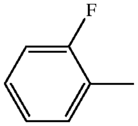 | 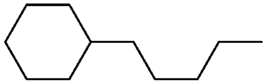 | 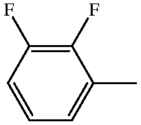 | 1 | 1 | $C_5H_{11}$ |
| 243 | $C_7H_{15}$ | 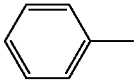 | 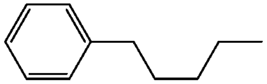 | 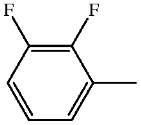 | 1 | 1 | $C_7H_{15}$ |
| 244 | $C_3H_7$ | 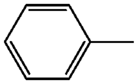 | 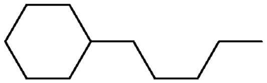 | 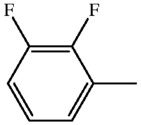 | 1 | 1 | $OC_3H_7$ |
| 245 | $C_5H_{11}$ | 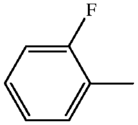 | 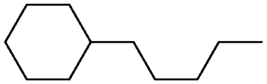 | 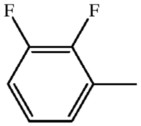 | 1 | 1 | $OC_2H_5$ |

-continued
| | $R^1$ | 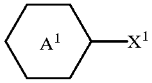 | 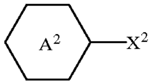 | 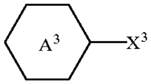 | m | n | $Y^1$ |
|---|---|---|---|---|---|---|---|
| 246 | $C_5H_{11}$ | 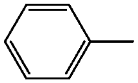 | 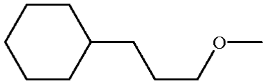 | 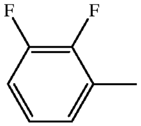 | 1 | 1 | $OC_4H_9$ |
| 247 | $C_3H_7$ | 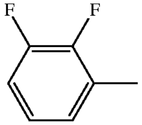 | 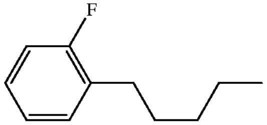 | 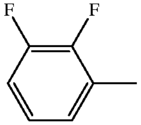 | 1 | 1 | $C_5H_{11}$ |
| 248 | $C_5H_{11}O$ | 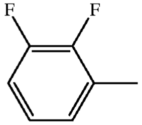 | 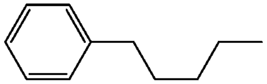 | 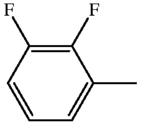 | 1 | 1 | $CH_3$ |
| 249 | $C_7H_{15}$ | 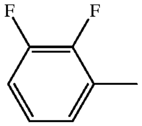 | 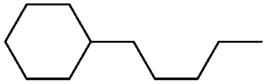 | 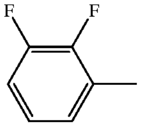 | 1 | 1 | $C_3H_7$ |
| 250 | $C_3H_7$ | 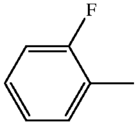 | 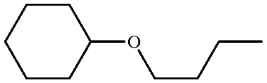 | 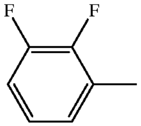 | 1 | 1 | $OCH_3$ |
| 251 | $C_5H_{11}$ | 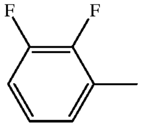 | 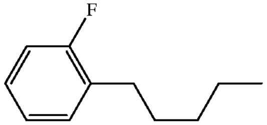 | 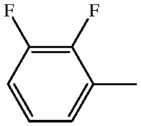 | 1 | 1 | $OC_2H_5$ |

-continued
| | $R^1$ | 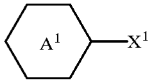 | 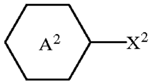 | 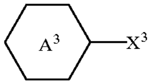 | m | n | $Y^1$ |
|---|---|---|---|---|---|---|---|
| 252 | $C_2H_5O$ | 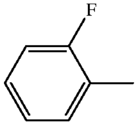 | 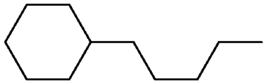 | 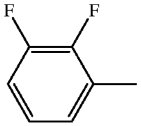 | 1 | 1 | $OC_4H_9$ |
| 253 | $C_3H_7$ | 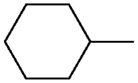 | 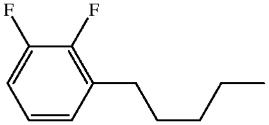 | 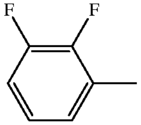 | 1 | 1 | $C_3H_7$ |
| 254 | $C_5H_{11}$ | 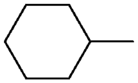 | 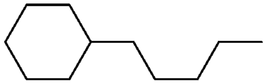 | 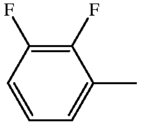 | 1 | 1 | $CH_3$ |
| 255 | 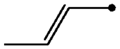 | 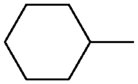 | 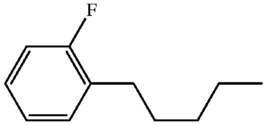 | 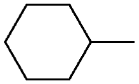 | 1 | 1 | $C_5H_{11}$ |
| 256 | $C_3H_7$ | 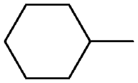 | 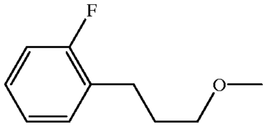 | 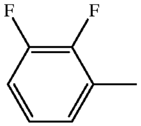 | 1 | 1 | $OC_2H_5$ |
| 257 | $C_5H_{11}$ | 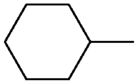 | 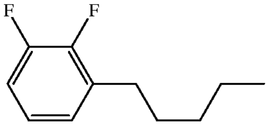 | 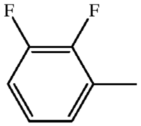 | 1 | 1 | $OC_3H_7$ |

-continued
| | $R^1$ | 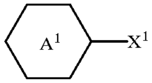 | 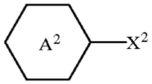 | 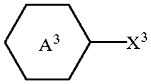 | m | n | $Y^1$ |
|---|---|---|---|---|---|---|---|
| 258 | $C_5H_{11}$ | 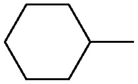 | 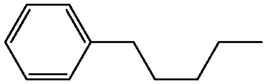 | 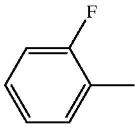 | 1 | 1 | $OC_4H_9$ |
| 259 | $C_3H_7$ | 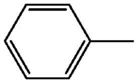 | 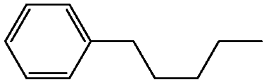 | 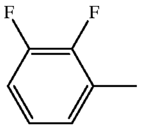 | 1 | 1 | $C_3H_7$ |
| 260 | $C_5H_{11}$ | 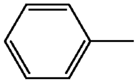 | 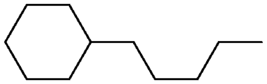 | 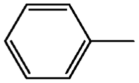 | 1 | 1 | $C_5H_{11}$ |
| 261 | $C_7H_{15}$ | 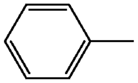 | 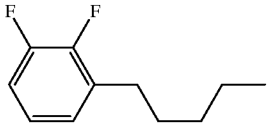 | 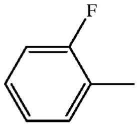 | 1 | 1 | $C_7H_{15}$ |
| 262 | $C_3H_7$ | 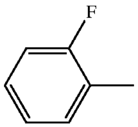 | 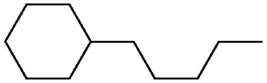 | 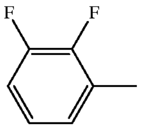 | 1 | 1 | $OC_2H_5$ |
| 263 | $C_5H_{11}$ | 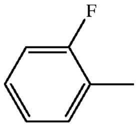 | 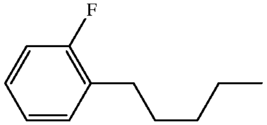 | 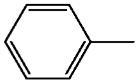 | 1 | 1 | $OC_3H_7$ |

-continued
| | $R^1$ | 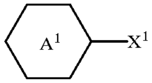 | 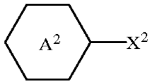 | 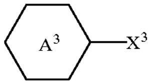 | m | n | $Y^1$ |
|---|---|---|---|---|---|---|---|
| 264 | $C_5H_{11}O$ | 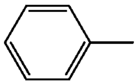 | 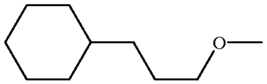 | 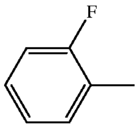 | 1 | 1 | $OC_4H_9$ |
| 265 | $C_3H_7$ | 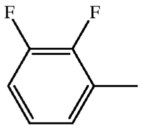 | 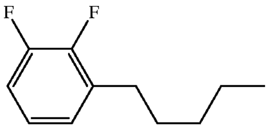 | 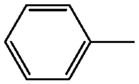 | 1 | 1 | $C_5H_{11}$ |
| 266 | $C_5H_{11}O$ | 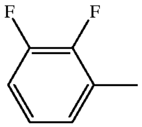 | 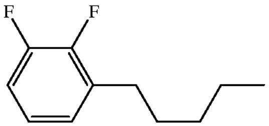 | 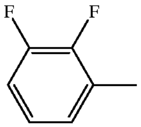 | 1 | 1 | $C_3H_7$ |
| 267 | $C_7H_{15}$ | 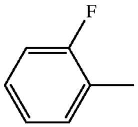 | 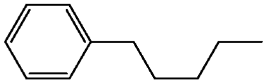 | 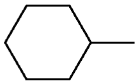 | 1 | 1 | $C_3H_7$ |
| 268 | $C_3H_7O$ | 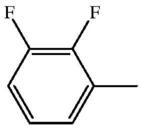 | 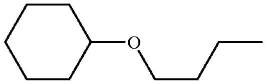 | 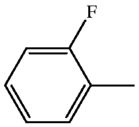 | 1 | 1 | $OCH_3$ |
| 269 | $C_5H_{11}$ | 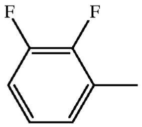 | 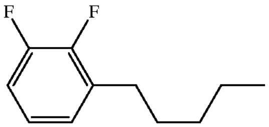 | 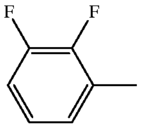 | 1 | 1 | $OC_4H_9$ |

-continued
| | $R^1$ | 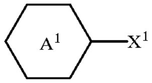 | 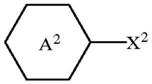 | 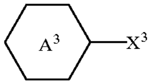 | m | n | $Y^1$ |
|---|---|---|---|---|---|---|---|
| 270 | $C_2H_5$ | 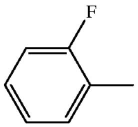 | 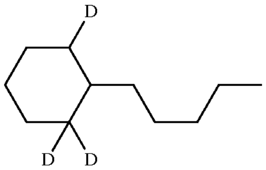 | 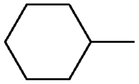 | 1 | 1 | $OC_2H_5$ |
| 271 | $C_2H_5$ | 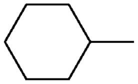 | 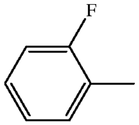 | 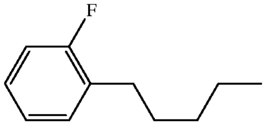 | 1 | 1 | $C_3H_7$ |
| 272 | $C_5H_{11}$ | 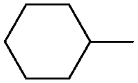 | 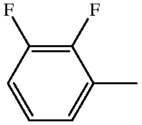 | 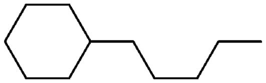 | 1 | 1 | $C_3H_7$ |
| 273 | 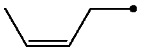 | 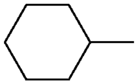 | 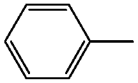 | 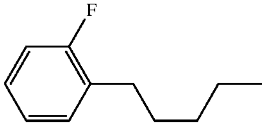 | 1 | 1 | $C_7H_{15}$ |
| 274 | $C_3H_7$ | 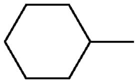 | 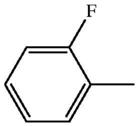 | 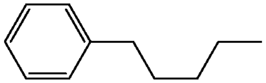 | 1 | 1 | $OC_2H_5$ |
| 275 | $C_5H_{11}$ | 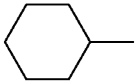 | 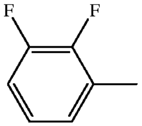 | 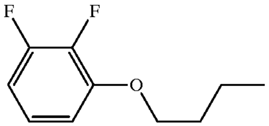 | 1 | 1 | $OC_3H_7$ |

-continued
| | $R^1$ | 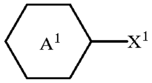 | 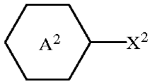 | 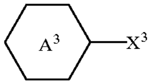 | m | n | $Y^1$ |
|---|---|---|---|---|---|---|---|
| 276 | $C_7H_{15}$ | 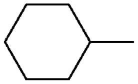 | 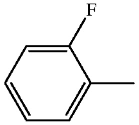 | 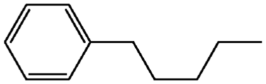 | 1 | 1 | $OC_4H_9$ |
| 277 | $C_3H_7$ | 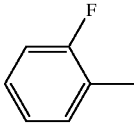 | 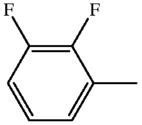 | 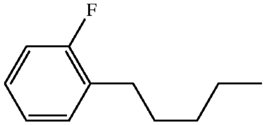 | 1 | 1 | $C_3H_7$ |
| 278 | $C_5H_{11}$ | 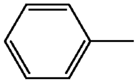 | 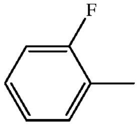 | 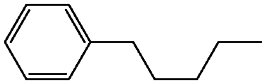 | 1 | 1 | $C_5H_{11}$ |
| 279 | $C_7H_{15}$ | 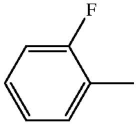 | 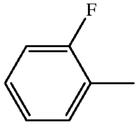 | 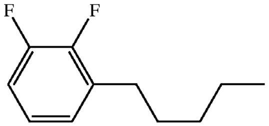 | 1 | 1 | $CH_3$ |
| 280 | $C_5H_{11}O$ | 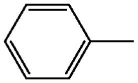 | 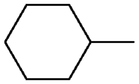 | 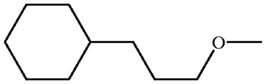 | 1 | 1 | $OC_2H_5$ |
| 281 | $C_5H_{11}$ | 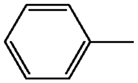 | 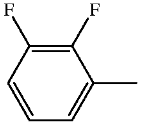 | 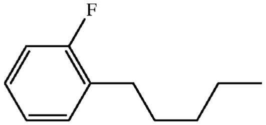 | 1 | 1 | $OC_4H_9$ |

-continued
| | $R^1$ | 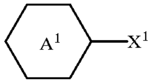 | 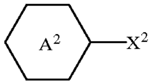 | 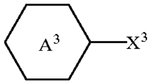 | m | n | $Y^1$ |
|---|---|---|---|---|---|---|---|
| 282 | $C_3H_7$ | 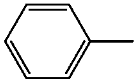 | 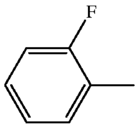 | 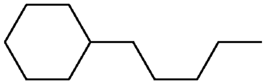 | 1 | 1 | $OC_3H_7$ |
| 283 | $C_3H_7$ | 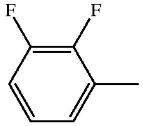 | 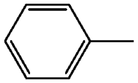 | 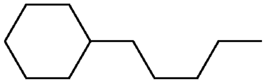 | 1 | 1 | $C_5H_{11}$ |
| 284 | $C_5H_{11}O$ | 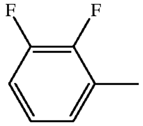 | 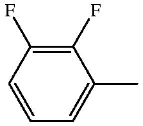 | 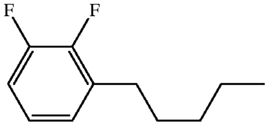 | 1 | 1 | $C_3H_7$ |
| 285 | $C_5H_{11}$ | 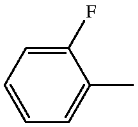 | 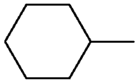 | 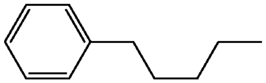 | 1 | 1 | $C_5H_{11}$ |
| 286 | $C_3H_7O$ | 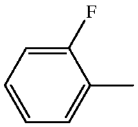 | 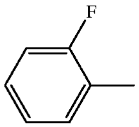 | 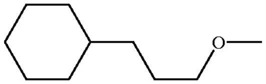 | 1 | 1 | $OC_4H_9$ |
| 287 | $C_3H_7$ | 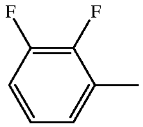 | 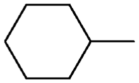 | 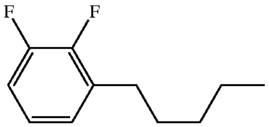 | 1 | 1 | $OCH_3$ |

-continued
| | $R^1$ | 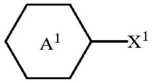 | 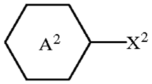 | 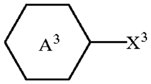 | m | n | $Y^1$ |
|---|---|---|---|---|---|---|---|
| 288 | $C_5H_{11}$ | 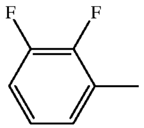 | 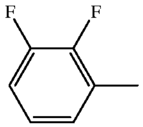 | 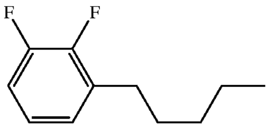 | 1 | 1 | $OC_2H_5$ |
| 289 | $C_3H_7$ | 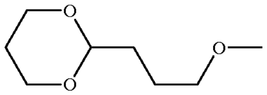 | | | 0 | 0 | $C_3H_7$ |
| 290 | $C_5H_{11}$ | 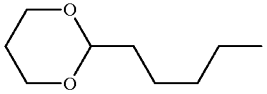 | | | 0 | 0 | $OC_2H_5$ |
| 291 | $C_3H_7O$ | 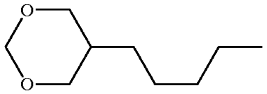 | | | 0 | 0 | $OC_3H_7$ |
| 292 | $C_3H_7$ | 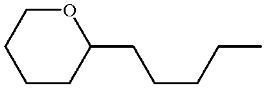 | | | 0 | 0 | $C_3H_7$ |
| 293 | $C_5H_{11}$ | 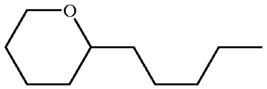 | | | 0 | 0 | $OC_2H_5$ |
| 294 | $C_7H_{15}$ | 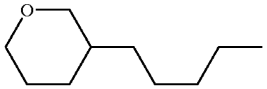 | | | 0 | 0 | $OCH_3$ |
| 295 | $C_3H_7$ | 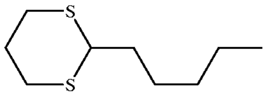 | | | 0 | 0 | $C_7H_{15}$ |

-continued
| | $R^1$ | 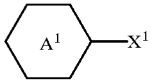 | 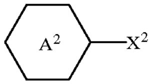 | 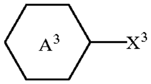 | m | n | $Y^1$ |
|---|---|---|---|---|---|---|---|
| 296 | $C_2H_5O$ | 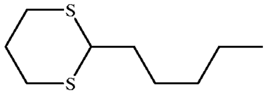 | | | 0 | 0 | $C_5H_{11}$ |
| 297 | $C_5H_{11}$ | 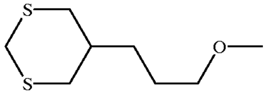 | | | 0 | 0 | $OC_4H_9$ |
| 298 | 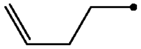 | 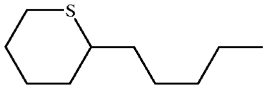 | | | 0 | 0 | $OC_4H_9$ |
| 299 | $C_5H_{11}$ | 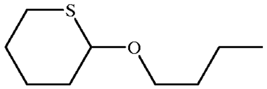 | | | 0 | 0 | $C_3H_7$ |
| 300 | $C_5H_{11}O$ | 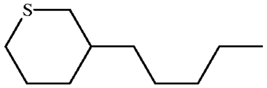 | | | 0 | 0 | $OCH_3$ |
| 301 | $C_3H_7$ | 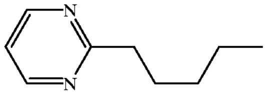 | | | 0 | 0 | $OC_2H_5$ |
| 302 | $C_5H_{11}$ | 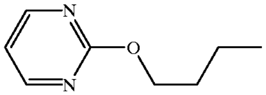 | | | 0 | 0 | $C_3H_7$ |
| 303 | $C_3H_7$ | 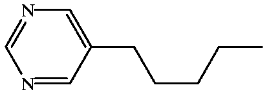 | | | 0 | 0 | $CH_3$ |

-continued
| | $R^1$ | 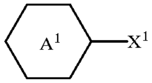 | 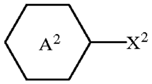 | 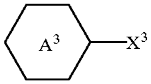 | m | n | $Y^1$ |
|---|---|---|---|---|---|---|---|
| 304 | $C_3H_7$ | 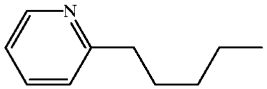 | | | 0 | 0 | $C_5H_{11}$ |
| 305 | $C_5H_{11}$ | 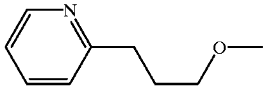 | | | 0 | 0 | $OC_2H_5$ |
| 306 | $C_7H_{15}O$ | 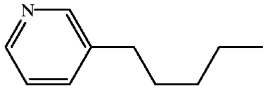 | | | 0 | 0 | $OC_3H_7$ |
| 307 | $C_3H_7$ | 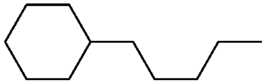 | 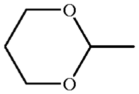 | | 1 | 0 | $C_5H_{11}$ |
| 308 | $C_5H_{11}O$ | 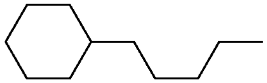 | 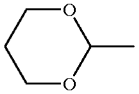 | | 1 | 0 | $OC_2H_5$ |
| 309 | $C_3H_7$ | 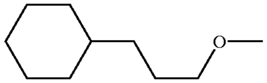 | 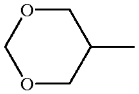 | | 1 | 0 | $C_3H_7$ |
| 310 | 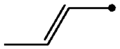 | 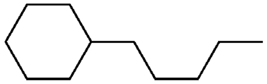 | 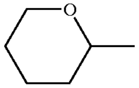 | | 1 | 0 | $C_3H_7$ |
| 311 | $C_5H_{11}$ | 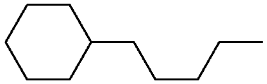 | 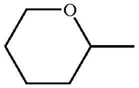 | | 1 | 0 | $OC_2H_5$ |

-continued
| | R[1] | 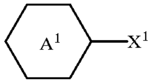 | 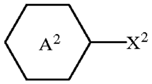 | 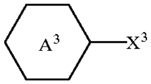 | m | n | $Y^1$ |
|---|---|---|---|---|---|---|---|
| 312 | $C_7H_{15}$ | 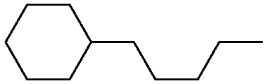 | 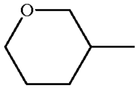 | | 1 | 0 | $C_3H_7$ |
| 313 | $C_3H_7$ | 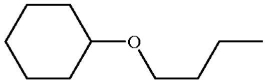 | 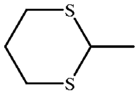 | | 1 | 0 | $C_7H_{15}$ |
| 314 | $C_2H_5O$ | 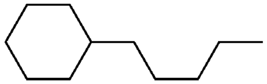 | 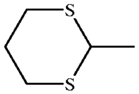 | | 1 | 0 | $C_5H_{11}$ |
| 315 | $C_5H_{11}$ | 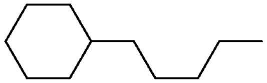 | 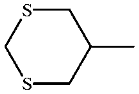 | | 1 | 0 | $OC_4H_9$ |
| 316 | $C_3H_7$ | 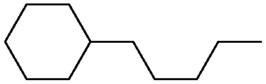 | 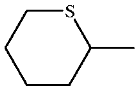 | | 1 | 0 | $OC_2H_5$ |
| 317 | $C_5H_{11}O$ | 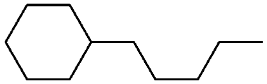 | 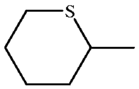 | | 1 | 0 | $C_3H_7$ |
| 318 | $C_5H_{11}$ | 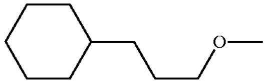 | 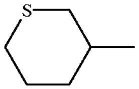 | | 1 | 0 | $OCH_3$ |
| 319 | $C_3H_7$ | 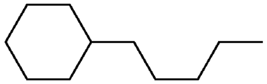 | 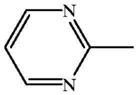 | | 1 | 0 | $OC_2H_5$ |

-continued
| | $R^1$ | 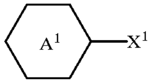 | 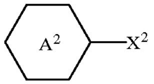 | 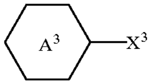 | m | n | $Y^1$ |
|---|---|---|---|---|---|---|---|
| 320 | $C_5H_{11}$ | 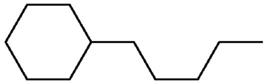 | 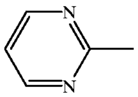 | | 1 | 0 | $C_3H_7$ |
| 321 | $C_3H_7$ | 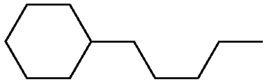 | 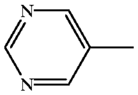 | | 1 | 0 | $OC_3H_7$ |
| 322 | $C_4H_9$ | 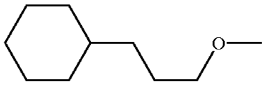 | 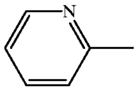 | | 1 | 0 | $C_5H_{11}$ |
| 323 | $C_5H_{11}$ | 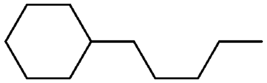 | 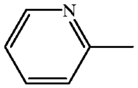 | | 1 | 0 | $OC_2H_5$ |
| 324 | $C_7H_{15}O$ | 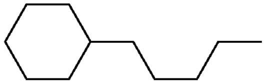 | 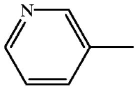 | | 1 | 0 | $CH_3$ |
| 325 | $C_5H_{11}$ | 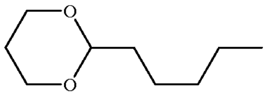 | 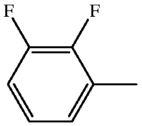 | | 1 | 0 | $OC_3H_7$ |
| 326 | $C_3H_7$ | 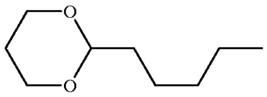 | 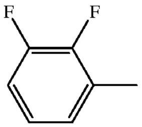 | | 1 | 0 | $OC_2H_5$ |

-continued
| | R¹ | 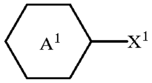 | 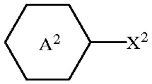 | 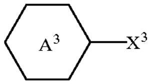 | m | n | Y¹ |
|---|---|---|---|---|---|---|---|
| 327 | $C_5H_{11}$ | 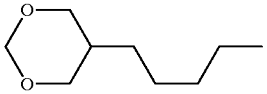 | 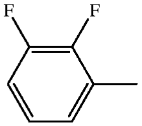 | | 1 | 0 | $C_3H_7$ |
| 328 | $C_3H_7$ | 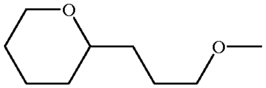 | 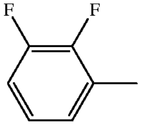 | | 1 | 0 | $C_3H_7$ |
| 329 | $C_3H_7O$ | 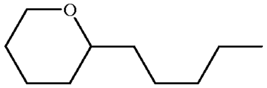 | 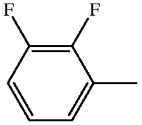 | | 1 | 0 | $C_7H_{15}$ |
| 330 | $C_7H_{15}$ | 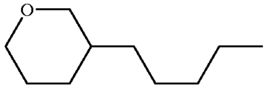 | 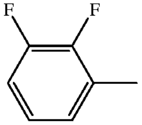 | | 1 | 0 | $OCH_3$ |
| 331 | $C_3H_7$ | 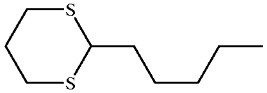 | 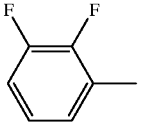 | | 1 | 0 | $OC_2H_5$ |
| 332 | 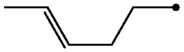 | 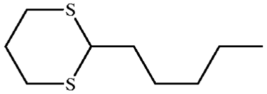 | 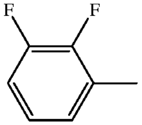 | | 1 | 0 | $C_5H_{11}$ |

-continued
| | $R^1$ | 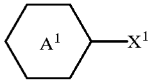 | 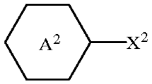 | 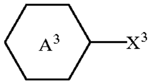 | m | n | $Y^1$ |
|---|---|---|---|---|---|---|---|
| 333 | $C_5H_{11}$ | 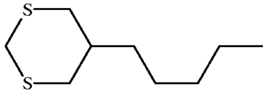 | 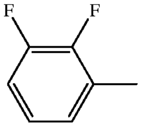 | | 1 | 0 | $OCH_3$ |
| 334 | $C_2H_5O$ | 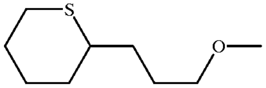 | 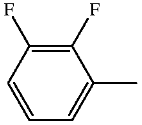 | | 1 | 0 | $OC_4H_9$ |
| 335 | $C_5H_{11}$ | 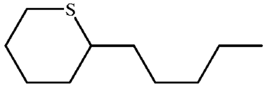 | 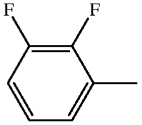 | | 1 | 0 | $C_3H_7$ |
| 336 | $C_3H_7$ | 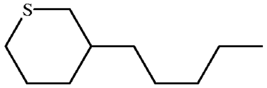 | 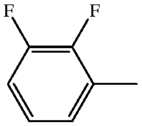 | | 1 | 0 | $OC_4H_9$ |
| 337 | $C_5H_{11}$ | 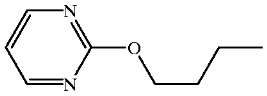 | 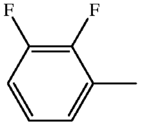 | | 1 | 0 | $OC_2H_5$ |
| 338 | $C_5H_{11}$ | 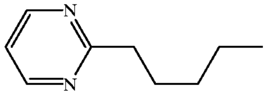 | 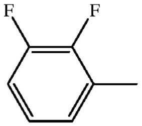 | | 1 | 0 | $C_3H_7$ |

-continued
| | $R^1$ | 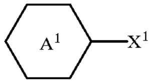 | 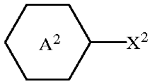 | 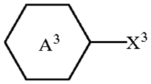 | m | n | $Y^1$ |
|---|---|---|---|---|---|---|---|
| 339 | $C_3H_7$ | 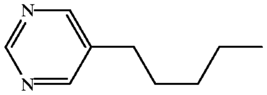 | 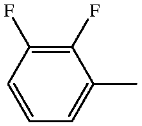 | | 1 | 0 | $C_5H_{11}$ |
| 340 | $C_5H_{11}O$ | 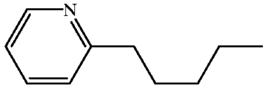 | 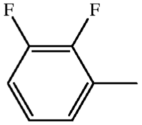 | | 1 | 0 | $CH_3$ |
| 341 | $C_3H_7$ | 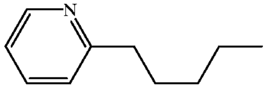 | 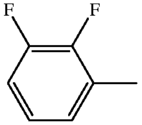 | | 1 | 0 | $OC_2H_5$ |
| 342 | $C_7H_{15}O$ | 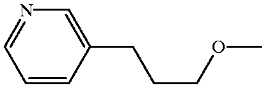 | 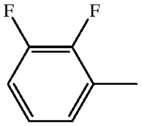 | | 1 | 0 | $OC_3H_7$ |
| 343 | $C_5H_{11}$ | 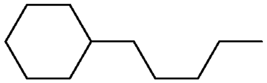 | 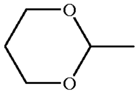 | 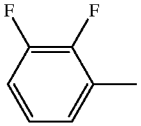 | 1 | 1 | $C_3H_7$ |
| 344 | $C_2H_5O$ | 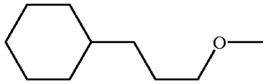 | 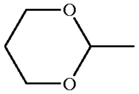 | 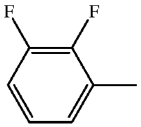 | 1 | 1 | $OC_2H_5$ |

-continued
| | $R^1$ | 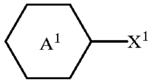 | 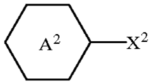 | 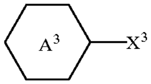 | m | n | $Y^1$ |
|---|---|---|---|---|---|---|---|
| 345 | $C_3H_7$ | 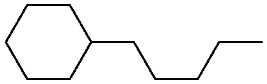 | 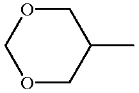 | 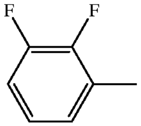 | 1 | 1 | $OC_4H_9$ |
| 346 | 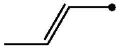 | 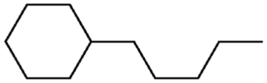 | 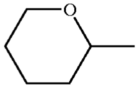 | 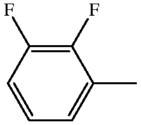 | 1 | 1 | $C_3H_7$ |
| 347 | $C_5H_{11}O$ | 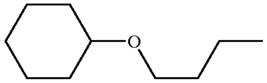 | 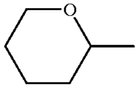 | 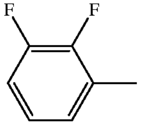 | 1 | 1 | $OC_2H_5$ |
| 348 | $C_7H_{15}$ | 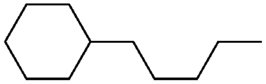 | 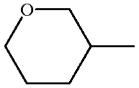 | 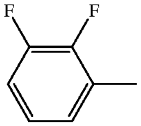 | 1 | 1 | $C_5H_{11}$ |
| 349 | $C_5H_{11}$ | 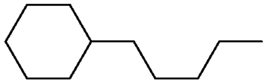 | 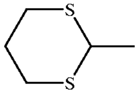 | 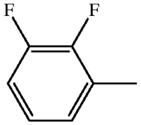 | 1 | 1 | $C_7H_{15}$ |
| 350 | $C_3H_7$ | 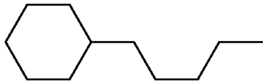 | 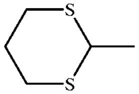 | 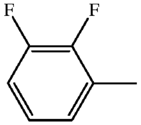 | 1 | 1 | $C_5H_{11}$ |

-continued
| | R¹ | 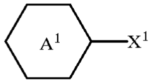 | 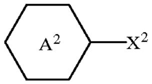 | 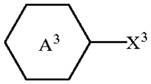 | m | n | $Y^1$ |
|---|---|---|---|---|---|---|---|
| 351 | $C_5H_{11}$ | 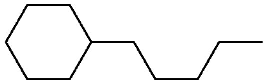 | 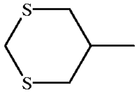 | 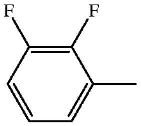 | 1 | 1 | $C_3H_7$ |
| 352 | $C_3H_7$ | 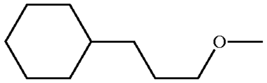 | 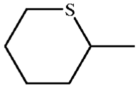 | 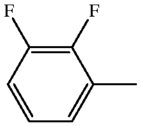 | 1 | 1 | $OC_2H_5$ |
| 353 | $C_5H_{11}O$ | 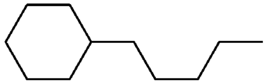 | 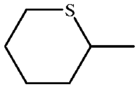 | 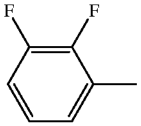 | 1 | 1 | $C_3H_7$ |
| 354 | $C_4H_9$ | 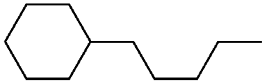 | 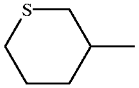 | 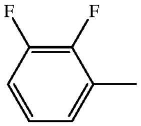 | 1 | 1 | $OC_3H_7$ |
| 355 | $C_3H_7$ | 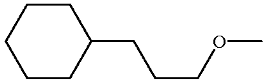 | 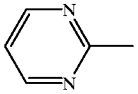 | 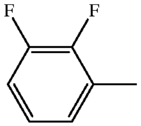 | 1 | 1 | $OC_2H_5$ |
| 356 | $C_5H_{11}$ | 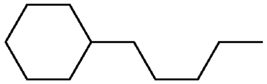 | 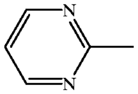 | 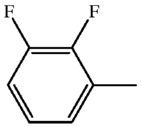 | 1 | 1 | $C_3H_7$ |

-continued
| | $R^1$ | 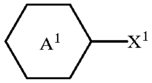 | 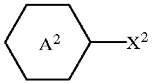 | 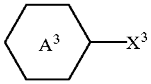 | m | n | $Y^1$ |
|---|---|---|---|---|---|---|---|
| 357 | $C_3H_7$ | 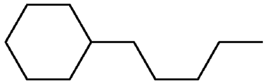 | 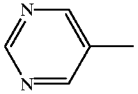 | 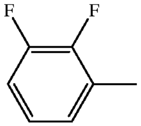 | 1 | 1 | $OCH_3$ |
| 358 | $C_3H_7O$ | 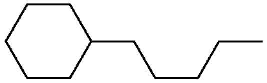 | 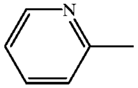 | 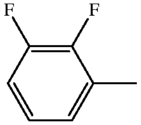 | 1 | 1 | $C_5H_{11}$ |
| 359 | $C_5H_{11}$ | 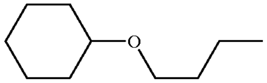 | 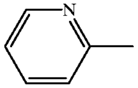 | 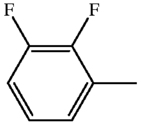 | 1 | 1 | $OC_2H_5$ |
| 360 | $C_7H_{15}O$ | 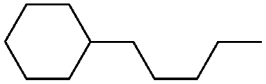 | 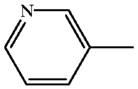 | 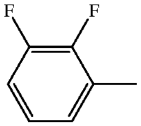 | 1 | 1 | $CH_3$ |
| 361 | $C_3H_7$ | 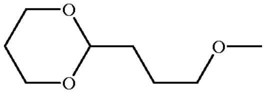 | 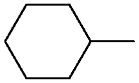 | | 1 | 0 | $C_3H_7$ |
| 362 | $C_5H_{11}O$ | 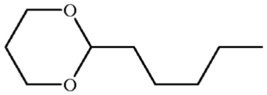 | 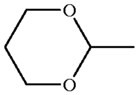 | | 1 | 0 | $OC_2H_5$ |

-continued
| | $R^1$ | 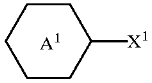 | 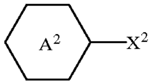 | 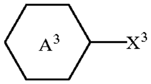 | m | n | $Y^1$ |
|---|---|---|---|---|---|---|---|
| 363 | $C_3H_7$ | 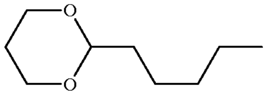 | 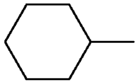 | 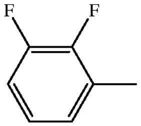 | 1 | 1 | $C_3H_7$ |
| 364 | 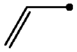 | 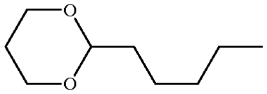 | 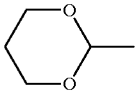 | 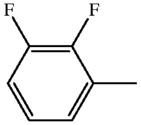 | 1 | 1 | $C_5H_{11}$ |
| 365 | $C_5H_{11}$ | 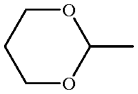 | 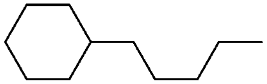 | | 1 | 0 | $OC_2H_5$ |
| 366 | $C_7H_{15}$ | 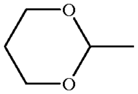 | 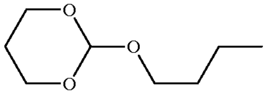 | | 1 | 0 | $C_3H_7$ |
| 367 | $C_3H_7$ | 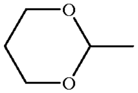 | 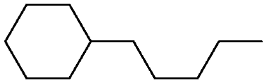 | 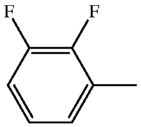 | 1 | 1 | $OC_2H_5$ |
| 368 | $C_2H_5O$ | 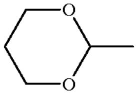 | 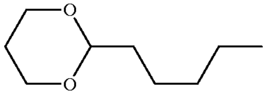 | 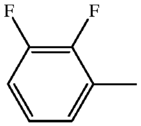 | 1 | 1 | $C_5H_{11}$ |

-continued
| | $R^1$ | 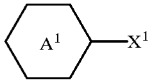 | 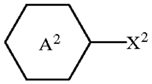 | 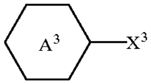 | m | n | $Y^1$ |
|---|---|---|---|---|---|---|---|
| 369 | $C_5H_{11}$ | 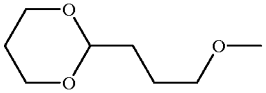 | 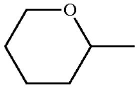 | 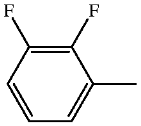 | 1 | 1 | $OC_2H_5$ |
| 370 | $C_3H_7$ | 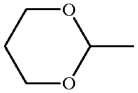 | 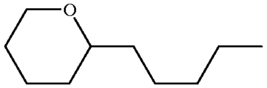 | | 1 | 0 | $C_7H_{15}$ |
| 371 | $C_5H_{11}O$ | 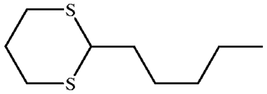 | 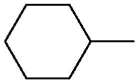 | | 1 | 0 | $C_3H_7$ |
| 372 | $C_5H_{11}$ | 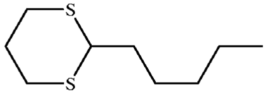 | 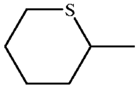 | 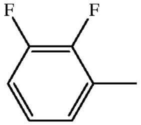 | 1 | 1 | $OCH_3$ |
| 373 | $C_3H_7$ | 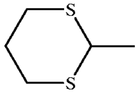 | 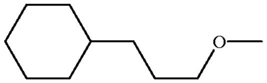 | | 1 | 0 | $CH_3$ |
| 374 | $C_5H_{11}$ | 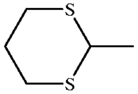 | 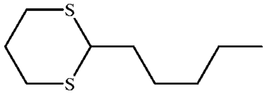 | 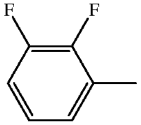 | 1 | 1 | $C_3H_7$ |
| 375 | $C_3H_7$ | 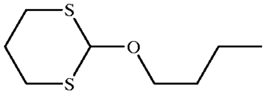 | 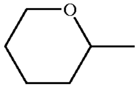 | | 1 | 0 | $OC_3H_7$ |

-continued
| | $R^1$ | 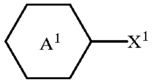 | 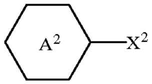 | 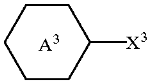 | m | n | $Y^1$ |
|---|---|---|---|---|---|---|---|
| 376 | $C_4H_9$ | 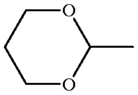 | 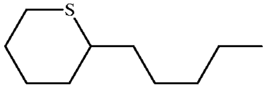 | 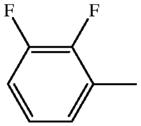 | 1 | 1 | $C_5H_{11}$ |
| 377 | $C_5H_{11}$ | 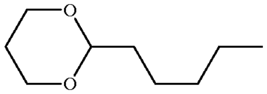 | 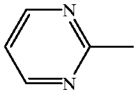 | 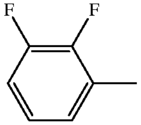 | 1 | 1 | $OC_2H_5$ |
| 378 | $C_7H_{15}O$ | 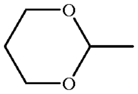 | 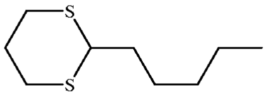 | | 1 | 0 | $OC_4H_9$ |

As nematic liquid crystal compositions comprising the liquid crystalline compound of the present invention produced by such methods as described above, the following Composition Examples (Use Examples 1 through 34) can be shown. In this connection, compounds in the Composition Examples are designated by abbreviation according to the definition shown in Table 1. Further, when the hydrogen atom of trans-1,4-cyclohexylene in the following partial structure was replaced by deuterium (heavy hydrogen) at positions $Q_1$, $Q_2$, and $Q_3$, it is designated by symbol H [1D, 2D, 3D], and when replaced by deuterium at positions $Q_5$, $Q_6$, and $Q_7$, it is designated by symbol H [5D, 6D, 7D]. In other words, the positions where deuterium substituted are indicated by the numeral in the bracket [ ].

In the Composition Examples (Use Examples), "%" means % by weight unless otherwise specified, and "part" means part by weight of an optically active compound based on 100 parts by weight of liquid crystal composition.

Determination of viscosity (η) was conducted at 20.0° C., and determination of each of optical anisotropy (Δn), dielectric anisotropy (Δε), threshold voltage (Vth), and twist pitch (P) was conducted at 25.0° C.

TABLE 1

$R—(A_1)—Z_1—. . . —Z_n—(A_n)—X$

| 1) Left side terminal group R- | Symbol |
|---|---|
| $CH_{2n+1}$— | n- |
| $C_nH_{2n+}O$— | nO- |
| $C_nH_{2n+1}OC_mH_{2m}$— | nOm- |
| $CH_2{=}CH$— | V- |
| $CH_2{=}CHC_nH_{2n}$— | Vn- |
| $C_nH_{2n+1}CH{=}CHC_mH_{2m}$— | nVm- |
| $C_nH_{2n+1}CH{=}CHC_mH_{2m}CH{=}CHC_kH_{2k}$— | nVmVk- |
| **2) Ring structure $—(A_1)—, —(A_n)—$** | **Symbol** |
| 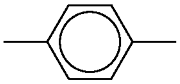 | B |
| 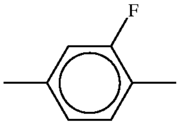 | (B)F |
| 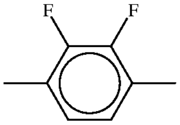 | B(2F,3F) |
| 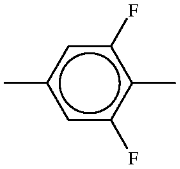 | B(F,F) |
| 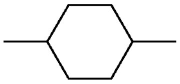 | H |
| 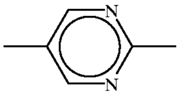 | Py |
| 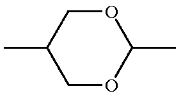 | D |

TABLE 1-continued

| | |
|---|---|
| 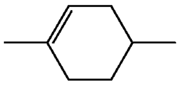 | Ch |
| 3) Bonding group<br>$-Z_1-$, $-Z_n-$ | Symbol |
| $-C_2H_4-$ | 2 |
| $-C_4H_8-$ | 4 |
| $-COO-$ | E |
| $-C{\equiv}C-$ | T |
| $-CH{=}CH-$ | V |
| $-CF_2O-$ | CF2O |
| $-OCF_2-$ | OCF2 |
| 4) Right side terminal<br>group -X | Symbol |
| $-F$ | —F |
| $-Cl$ | —CL |
| $-CN$ | —C |
| $-CF_3$ | —CF3 |
| $-OCF_3$ | —OCF3 |
| $-OCF_2H$ | —OCF2H |
| $-C_nH_{2n+1}$ | -n |
| $-OC_nH_{2n+1}$ | —On |
| $-COOCH_3$ | -EMe |
| $-C_nH_{2n}CH{=}CH_2$ | -nV |
| $-C_mH_{2m}CH{=}CHC_nH_{2n+1}$ | -mVn |
| $-C_mH_{2m}CH{=}CHC_nH_{2n}F$ | -mVnF |
| $-CH{=}CF_2$ | —VFF |
| $-C_nH_{2n}CH{=}CF_2$ | -nVFF |
| $-C{\equiv}C-CN$ | -TC |
| 5) Example of designation | |

Example 1 3-H2B(F,F)B(F)—F

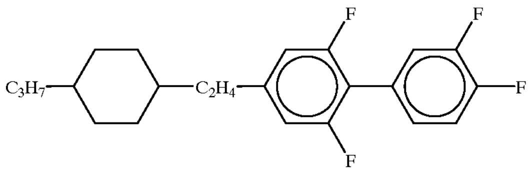

Example 2 3-HB(F)TB-2

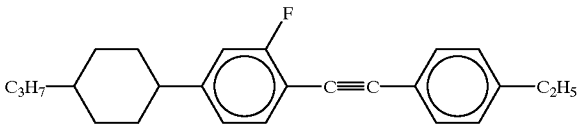

Example 3 1V2-BEB(F,F)—C

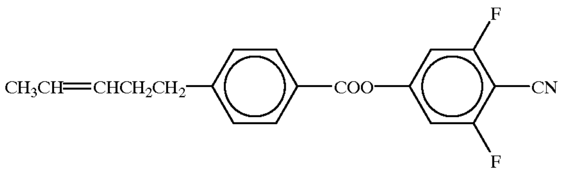

TABLE 1-continued

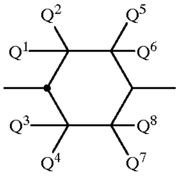

USE EXAMPLE 1

| | | |
|---|---|---|
| 5-H4HB(2F, 3F)-3 | (No. 20) | 15.0% |
| 3-HEB-O4 | | 23.4% |
| 4-HEB-O2 | | 17.6% |
| 5-HEB-O1 | | 17.6% |
| 3-HEB-O2 | | 14.7% |
| 5-HEB-O2 | | 11.7% |
| $T_{NI}$ = 77.0 (° C.) | | |
| $\Delta\epsilon$ = −1.5 | | |

USE EXAMPLE 2

| | | |
|---|---|---|
| 5-H4HB(2F, 3F)-O2 | (No. 23) | 15.0% |
| 3-HEB-O4 | | 23.4% |
| 4-HEB-O2 | | 17.6% |
| 5-HEB-O1 | | 17.6% |
| 3-HEB-O2 | | 14.7% |
| 5-HEB-O2 | | 11.7% |
| $T_{NI}$ = 81.8 (° C.) | | |
| $\Delta\epsilon$ = −2.1 | | |

USE EXAMPLE 3

| | | |
|---|---|---|
| 3-HH4B(2F, 3F)-O2 | (No. 94) | 15.0% |
| 3-HEB-O4 | | 23.4% |
| 4-HEB-O2 | | 17.6% |
| 5-HEB-O1 | | 17.6% |
| 3-HEB-O2 | | 14.7% |
| 5-HEB-O2 | | 11.7% |
| $T_{NI}$ = 81.0 (° C.) | | |
| $\Delta\epsilon$ = −1.9 | | |

USE EXAMPLE 4

| | | |
|---|---|---|
| 3-HH4B(2F, 3F)B(2F, 3F)-O2 | (No. 238) | 15.0% |
| 3-HEB-O4 | | 23.4% |
| 4-HEB-O2 | | 17.6% |
| 5-HEB-O1 | | 17.6% |
| 3-HEB-O2 | | 14.7% |
| 5-HEB-O2 | | 11.7% |
| $T_{NI}$ = 90.2 (° C.) | | |
| $\Delta\epsilon$ = −2.3 | | |

USE EXAMPLE 5

| | | |
|---|---|---|
| 3-HH4B(2F, 3F)-O2 | (No. 94) | 10.0% |
| 1V2-BEB(F, F)-C | | 5.0% |
| 3-HB-C | | 25.0% |
| 1-BTB-3 | | 5.0% |
| 2-BTB-1 | | 10.0% |
| 3-HH-4 | | 6.0% |
| 3-HHB-1 | | 11.0% |
| 3-HHB-3 | | 4.0% |
| 3-H2BTB-2 | | 4.0% |
| 3-H2BTB-3 | | 4.0% |
| 3-H2BTB-4 | | 4.0% |
| 3-HB(F)TB-2 | | 6.0% |
| 3-HB(F)TB-3 | | 6.0% |
| CM33 | | 0.8 part |
| $T_{NI}$ = 90.3 (° C.) | | |
| $\eta$ = 17.8 (mPa · s) | | |
| $\Delta n$ = 0.165 | | |
| $\Delta\epsilon$ = 6.5 | | |
| $V_{th}$ = 2.18 (V) | | |
| P = 11.3 $\mu$m | | |

USE EXAMPLE 6

| | | |
|---|---|---|
| 5-H4HB(2F, 3F)-3 | (No. 20) | 7.0% |
| V2-HB-C | | 12.0% |
| 1V2-HB-C | | 12.0% |
| 3-HB-C | | 15.0% |
| 3-H[1D, 2D, 3D]-C | | 9.0% |
| 3-HB(F)-C | | 5.0% |
| 2-BTB-1 | | 2.0% |
| 3-HH-4 | | 4.0% |
| 3-HH-VFF | | 6.0% |
| 2-H[1D, 2D, 3D]HB-C | | 3.0% |
| 3-HHB-C | | 6.0% |
| 3-HB(F)TB-2 | | 5.0% |
| 3-H2BTB-2 | | 5.0% |
| 3-H2BTB-3 | | 5.0% |
| 3-H2BTB-4 | | 4.0% |
| $T_{NI}$ = 87.3 (° C.) | | |
| $\eta$ = 19.9 (mPa · s) | | |
| $\Delta n$ = 0.154 | | |
| $\Delta\epsilon$ = 8.5 | | |
| $V_{th}$ = 2.05 (V) | | |

USE EXAMPLE 7

| | | |
|---|---|---|
| 5-H4HB(2F, 3F)-O2 | (No. 23) | 5.0% |
| 2O1-BEB(F)-C | | 5.0% |
| 3O1-BEB(F)-C | | 15.0% |
| 4O1-BEB(F)-C | | 13.0% |
| 5O1-BEB(F)-C | | 13.0% |
| 2-HHB(F)-C | | 15.0% |
| 3-HHB(F)-C | | 15.0% |

-continued

| | | |
|---|---|---|
| 3-HB(F)TB-2 | | 4.0% |
| 3-HB(F)TB-3 | | 4.0% |
| 3-HB(F)TB-4 | | 4.0% |
| 3-HHB-1 | | 3.0% |
| 3-HHB-O1 | | 4.0% |
| $T_{NI}$ = 88.4 (° C.) | | |
| η = 88.0 (mPa · s) | | |
| Δn = 0.149 | | |
| Δε = 30.6 | | |
| $V_{th}$ = 0.90 (V) | | |

USE EXAMPLE 8

| | | |
|---|---|---|
| 3-HH4B(2F, 3F)-O2 | (No. 94) | 6.0% |
| 5-PyB-F | | 4.0% |
| 3-PyB(F)-F | | 4.0% |
| 2-BB-C | | 5.0% |
| 4-BB-C | | 4.0% |
| 5-BB-C | | 5.0% |
| 2-PyB-2 | | 2.0% |
| 3-PyB-2 | | 2.0% |
| 4-PyB-2 | | 2.0% |
| 6-PyB-O5 | | 3.0% |
| 6-PyB-O6 | | 3.0% |
| 6-PyB-O7 | | 3.0% |
| 6-PyB-O8 | | 3.0% |
| 3-PyBB-F | | 6.0% |
| 4-PyBB-F | | 6.0% |
| 5-PyBB-F | | 6.0% |
| 3-HHB-3 | | 8.0% |
| 2-H2BTB-2 | | 4.0% |
| 2-H2BTB-3 | | 4.0% |
| 2-H2BTB-4 | | 5.0% |
| 3-H2BTB-2 | | 5.0% |
| 3-H2BTB-3 | | 5.0% |
| 3-H2BTB-4 | | 5.0% |
| $T_{NI}$ = 90.8 ° C.) | | |
| η = 36.4 (mPa · s) | | |
| Δn = 0.201 | | |
| Δε = 6.1 | | |
| $V_{th}$ = 2.31 (V) | | |

USE EXAMPLE 9

| | | |
|---|---|---|
| 5-H4HB(2F, 3F)-3 | (No. 20) | 4.0% |
| 3-HH4B(2F, 3F)-O2 | (No. 94) | 3.0% |
| 3-DB-C | | 10.0% |
| 4-DB-C | | 10.0% |
| 2-BEB-C | | 12.0% |
| 3-BEB-C | | 4.0% |
| 3-PyB(F)-F | | 6.0% |
| 3-HEB-O4 | | 8.0% |
| 4-HEB-O2 | | 6.0% |
| 5-HEB-O1 | | 6.0% |
| 3-HEB-O2 | | 5.0% |
| 5-HEB-5 | | 5.0% |
| 4-HEB-5 | | 5.0% |
| 1O-BEB-2 | | 4.0% |
| 3-HHB-1 | | 3.0% |
| 3-HHEBB-C | | 3.0% |
| 3-HBEBB-C | | 3.0% |
| 5-HBEBB-C | | 3.0% |
| $T_{NI}$ = 68.1 (° C.) | | |
| η = 40.5 (mPa · s) | | |
| Δn = 0.121 | | |
| Δε = 11.1 | | |
| $V_{th}$ = 1.35 (V) | | |

USE EXAMPLE 10

| | | |
|---|---|---|
| 5-H4HB(2F, 3F)-3 | (No. 20) | 4.0% |
| 5-H4HB(2F, 3F)-O2 | (No. 23) | 4.0% |
| 3-HH4B(2F, 3F)-O2 | (No. 94) | 4.0% |
| 3-HH4B(2F, 3F)B(2F, 3F)-O2 | (No. 238) | 4.0% |
| 3-HB-C | | 18.0% |
| 7-HB-C | | 3.0% |
| 1O1-HB-C | | 10.0% |
| 3-HB(F)-C | | 10.0% |
| 2-PyB-2 | | 2.0% |
| 3-PyB-2 | 2.0% | |
| 4-PyB-2 | | 2.0% |
| 1O1-HH-3 | | 7.0% |
| 2-BTB-O1 | | 7.0% |
| 3-HHB-1 | | 2.0% |
| 3-HHB-F | | 2.0% |
| 3-HHB-O1 | | 3.0% |
| 3-H2BTB-2 | | 3.0% |
| 3-H2BTB-3 | | 3.0% |
| 2-PyBH-3 | | 4.0% |
| 3-PyBH-3 | | 3.0% |
| 3-PyBB-2 | | 3.0% |
| $T_{NI}$ = 72.1 (° C.) | | |
| η = 23.2 (mPa · s) | | |
| Δn = 0.140 | | |
| Δε = 7.1 | | |
| $V_{th}$ = 1.90 (V) | | |

USE EXAMPLE 11

| | | |
|---|---|---|
| 5-H4HB(2F, 3F)-3 | (No. 20) | 10.0% |
| 2O1-BEB(F)-C | | 5.0% |
| 3O1-BEB(F)-C | | 12.0% |
| 5O1-BEB(F)-C | | 4.0% |
| IV2-BEB(F, F)-C | | 10.0% |
| 3-HH-EMe | | 10.0% |
| 3-HB-O2 | | 18.0% |
| 7-HEB-F | | 2.0% |
| 3-HHEB-F | | 2.0% |
| 5-HHEB-F | | 2.0% |
| 3-HBEB-F | | 4.0% |
| 2O1-HBEB(F)-C | | 2.0% |
| 3-HB(F)EB(F)-C | | 2.0% |
| 3-HBEB(F, F)-C | | 2.0% |
| 3-HHB-F | | 4.0% |
| 3-HHB-O1 | | 4.0% |
| 3-HHB-3 | | 3.0% |
| 3-HEBEB-F | | 2.0% |
| 3-HEBEB-1 | | 2.0% |
| $T_{NI}$ = 70.0 (° C.) | | |
| η = 38.0 (mPa · s) | | |
| Δn = 0.112 | | |
| Δε = 23.0 | | |
| $V_{th}$ = 1.04 (V) | | |

USE EXAMPLE 12

| | | |
|---|---|---|
| 3-HH4B(2F, 3F)-O2 | (No. 94) | 7.0% |
| 5-BEB(F)-C | | 5.0% |
| V-HB-C | | 14.0% |
| 5-PyB-C | | 6.0% |
| 4-BB-3 | | 10.0% |
| 3-HH-2V | | 10.0% |
| 5-HH-V | | 6.0% |
| V-HHB-1 | | 7.0% |
| V2-HHB-1 | | 15.0% |
| 3-HHB-1 | | 5.0% |
| 1V2-HBB-2 | | 10.0% |
| 3-HHEBH-3 | | 5.0% |

-continued

| | | |
|---|---|---|
| $T_{NI}$ = 90.1 (° C.) | | |
| η = 17.9 (mPa · s) | | |
| Δn = 0.115 | | |
| Δε = 4.8 | | |
| $V_{th}$ = 2.37 (V) | | |

USE EXAMPLE 13

| | | |
|---|---|---|
| 5-H4HB(2F, 3F)-3 | (No. 20) | 5.0% |
| 5-H4HB(2F, 3F)-O2 | (No. 23) | 5.0% |
| 2O1-BEB(F)-C | | 5.0% |
| 3O1-BEB(F)-C | | 12.0% |
| 5O1-BEB(F)-C | | 4.0% |
| 1V2-BEB(F, F)-C | | 16.0% |
| 3-HB-O2 | | 10.0% |
| 3-HH-4 | | 3.0% |
| 3-HHB-F | | 3.0% |
| 3-HHB-O1 | | 2.0% |
| 3-HBEB-F | | 4.0% |
| 3-HHEB-F | | 7.0% |
| 5-HHEB-F | | 7.0% |
| 3-H2BTB-2 | | 4.0% |
| 3-H2BTB-3 | | 4.0% |
| 3-H2BTB-4 | | 4.0% |
| 3-HB(F)TB-2 | | 5.0% |
| $T_{NI}$ = 84.7 (° C.) | | |
| η = 43.2 (mPa · s) | | |
| Δn = 0.140 | | |
| Δε = 27.5 | | |
| $V_{th}$ = 1.06 (V) | | |

USE EXAMPLE 14

| | | |
|---|---|---|
| 3-HH4B(2F, 3F)-O2 | (No. 94) | 5.0% |
| 3-HH3OB(2F, 3F)B(2F, 3F)-5 | (No. 237) | 4.0% |
| 2-BEB-C | | 12.0% |
| 3-BEB-C | | 4.0% |
| 4-BEB-C | | 6.0% |
| 3-HB-C | | 28.0% |
| 3-HEB-O4 | | 12.0% |
| 4-HEB-O2 | | 8.0% |
| 5-HEB-O1 | | 8.0% |
| 3-HEB-O2 | | 6.0% |
| 3-HHB-1 | | 3.0% |
| 3-HHB-O1 | | 4.0% |
| $T_{NI}$ = 65.1 (° C.) | | |
| η = 29.1 (mPa · s) | | |
| Δn = 0.116 | | |
| Δε = 9.2 | | |
| $V_{th}$ = 1.43 (V) | | |

USE EXAMPLE 15

| | | |
|---|---|---|
| 5-H4HB(2F, 3F)-3 | (No. 20) | 5.0% |
| 2-BEB-C | | 10.0% |
| 5-BB-C | | 12.0% |
| 7-BB-C | | 7.0% |
| 1-BTB-3 | | 7.0% |
| 2-BTB-1 | | 10.0% |
| 1O-BEB-2 | | 10.0% |
| 1O-BEB-5 | | 12.0% |
| 2-HHB-1 | | 4.0% |
| 3-HHB-F | | 4.0% |
| 3-HHB-1 | | 7.0% |
| 3-HHB-O1 | | 4.0% |

-continued

| | | |
|---|---|---|
| 3-HHB-3 | | 8.0% |
| $T_{NI}$ = 63.4 (° C.) | | |
| η = 21.2 (mPa · s) | | |
| Δn = 0.160 | | |
| Δε = 6.2 | | |
| $V_{th}$ = 1.82 (V) | | |

USE EXAMPLE 16

| | | |
|---|---|---|
| 5-H4HB(2F, 3F)-3 | (No. 20) | 5.0% |
| 5-H4HB(2F, 3F)-O2 | (No. 23) | 5.0% |
| 3-HH4B(2F, 3F)-O2 | (No. 94) | 5.0% |
| 1V2-BEB(F, F)-C | | 8.0% |
| 3-HB-C | | 10.0% |
| V2V-HB-C | | 14.0% |
| V2V-HH-3 | | 14.0% |
| 3-HB-O2 | | 4.0% |
| 3-HHB-1 | | 10.0% |
| 3-HHB-3 | | 5.0% |
| 3-HB(F)TB-2 | | 4.0% |
| 3-HB(F)TB-3 | | 4.0% |
| 3-H2BTB-2 | | 4.0% |
| 3-H2BTB-3 | | 4.0% |
| 3-H2BTB-4 | | 4.0% |
| $T_{NI}$ = 98.1 (° C.) | | |
| η = 20.8 (mPa · s) | | |
| Δn = 0.130 | | |
| Δε = 7.2 | | |
| $V_{th}$ = 2.18 (V) | | |

USE EXAMPLE 17

| | | |
|---|---|---|
| 5-H4HB(2F, 3F)-O2 | (No. 23) | 5.0% |
| 3-HH4B(2F, 3F)-O2 | (No. 94) | 5.0% |
| 5-BTB(F)TB-3 | | 10.0% |
| V2-HB-TC | | 10.0% |
| 3-HB-TC | | 10.0% |
| 3-HB-C | | 10.0% |
| 5-HB-C | | 7.0% |
| 5-BB-C | | 3.0% |
| 2-BTB-1 | | 10.0% |
| 2-BTB-O1 | | 5.0% |
| 3-HH-4 | | 5.0% |
| 3-HHB-3 | | 11.0% |
| 3-H2BTB-2 | | 3.0% |
| 3-H2BTB-3 | | 3.0% |
| 3-HB(F)TB-2 | | 3.0% |
| $T_{NI}$ = 92.8 (° C.) | | |
| η = 16.7 (mPa · s) | | |
| Δn = 0.203 | | |
| Δε = 6.3 | | |
| $V_{th}$ = 2.15 (V) | | |

USE EXAMPLE 18

| | | |
|---|---|---|
| 5-H4HB(2F, 3F)-3 | (No. 20) | 10.0% |
| 2-HHB(F)-F | | 17.0% |
| 3-HHB(F)-F | | 17.0% |
| 5-HHB(F)-F | | 16.0% |
| 2-H2HB(F)-F | | 10.0% |
| 3-H2HB(F)-F | | 5.0% |
| 2-HBB(F)-F | | 6.0% |
| 3-HBB(F)-F | | 6.0% |
| 5-HBB(F)-F | | 13.0% |
| CN | | 0.3 part |

-continued

| |
|---|
| $T_{NI}$ = 100.8 (° C.) |
| η = 27.3 (mPa · s) |
| Δn = 0.094 |
| Δε = 4.6 |
| $V_{th}$ = 2.25 (V) |
| p = 81 μm |

USE EXAMPLE 19

| | | |
|---|---|---|
| 5-H4HB(2F, 3F)-O2 | (No. 23) | 6.0% |
| 7-HB(F)-F | | 5.0% |
| 5-H2B(F)-F | | 5.0% |
| 3-HB-O2 | | 10.0% |
| 3-HH-4 | | 2.0% |
| 3-HH[5D, 6D, 7D]-4 | | 3.0% |
| 2-HHB(F)-F | | 10.0% |
| 3-HHB(F)-F | | 10.0% |
| 5-HH[5D, 6D, 7D]B(F)-F | | 10.0% |
| 3-H2HB(F)-F | | 5.0% |
| 2-HBB(F)-F | | 3.0% |
| 3-HBB(F)-F | | 3.0% |
| 5-HBB(F)-F | | 6.0% |
| 2-H2BB(F)-F | | 5.0% |
| 3-H2BB(F)-F | | 6.0% |
| 3-HHB-1 | | 2.0% |
| 3-HHB-O1 | | 5.0% |
| 3-HHB-3 | | 4.0% |
| $T_{NI}$ = 83.9 (° C.) | | |
| η = 19.9 (mPa · s) | | |
| Δn = 0.091 | | |
| Δε = 3.0 | | |
| $V_{th}$ = 2.69 (V) | | |

USE EXAMPLE 20

| | | |
|---|---|---|
| 5-H4HB(2F,3F)—O2 | (No. 23) | 5.0% |
| 3-HH4B(2F,3F)—O2 | (No. 94) | 5.0% |
| 7-HB(F,F)—F | | 3.0% |
| 3-HB—O2 | | 7.0% |
| 2-HHB(F)—F | | 10.0% |
| 3-HHB(F)—F | | 10.0% |
| 2-HBB(F)—F | | 9.0% |
| 3-HBB(F)—F | | 9.0% |
| 5-HBB(F)—F | | 16.0% |
| 2-HBB—F | | 4.0% |
| 3-HBB—F | | 4.0% |
| 5-HBB—F | | 3.0% |
| 3-HBB(F,F)—F | | 5.0% |
| 5-HBB(F,F)—F | | 10.0% |

$T_{NI}$ = 85.5 (° C.)
η = 27.9 (mPa · s)
Δn = 0.116
Δε = 5.4
$V_{th}$ = 2.03 (V)

USE EXAMPLE 21

| | | |
|---|---|---|
| 5-H4HB(2F,3F)—3 | (No. 20) | 5.5% |
| 5-H4HB(2F,3F)—O2 | (No. 23) | 5.0% |
| 3-HH4B(2F,3F)—O2 | (No. 94) | 5.0% |
| 7-HB(F,F)—F | | 3.0% |
| 3-H2HB(F,F)—F | | 12.0% |
| 4-H2HB(F,F)—F | | 10.0% |
| 5-H2HB(F,F)—F | | 10.0% |
| 3-HHB(F,F)—F | | 5.0% |

-continued

| | |
|---|---|
| 4-HHB(F,F)—F | 5.0% |
| 3-HH2B(F,F)—F | 10.0% |
| 3-HBB(F,F)—F | 12.0% |
| 5-HBB(F,F)—F | 12.0% |
| 3-HBCF2OB(F,F)—F | 6.0% |

$T_{NI}$ = 72.1 (° C.)
η = 29.5 (mPa · s)
Δn = 0.087
Δε = 8.1
$V_{th}$ = 1.61 (V)

USE EXAMPLE 22

| | | |
|---|---|---|
| 5-H4HB(2F,3F)—O2 | (No. 23) | 4.0% |
| 3-HH4B(2F,3F)—O2 | (No. 94) | 3.0% |
| 3-HH4B(2F,3F)B(2F,3F)—O2 | (No. 238) | 3.0% |
| 7-HB(F,F)—F | | 5.0% |
| 3-H2HB(F,F)—F | | 12.0% |
| 3-HHB(F,F)—F | | 10.0% |
| 4-HHB(F,F)—F | | 5.0% |
| 3-HBB(F,F)—F | | 10.0% |
| 3-HHEB(F,F)—F | | 10.0% |
| 4-HHEB(F,F)—F | | 3.0% |
| 5-HHEB(F,F)—F | | 3.0% |
| 2-HBEB(F,F)—F | | 3.0% |
| 3-HBEB(F,F)—F | | 5.0% |
| 5-HBEB(F,F)—F | | 3.0% |
| 3-HDB(F,F)—F | | 15.0% |
| 3-HHBB(F,F)—F | | 6.0% |

$T_{NI}$ = 77.8 (° C.)
η = 37.5 (mPa · s)
Δn = 0.087
Δε = 12.4
$V_{th}$ = 1.44 (V)

USE EXAMPLE 23

| | | |
|---|---|---|
| 5-H4HB(2F,3F)—O2 | (No. 23) | 7.0% |
| 3-HH3OB(2F,3F)B(2F,3F)-5 | (No. 237) | 3.0% |
| 3-HB—CL | | 10.0% |
| 5-HB—CL | | 4.0% |
| 7-HB—CL | | 4.0% |
| 1O1-HH-5 | | 3.0% |
| 2-HBB(F)—F | | 8.0% |
| 3-HBB(F)—F | | 8.0% |
| 5-HBB(F)—F | | 14.0% |
| 4-HHB—CL | | 8.0% |
| 3-H2HB(F)—CL | | 4.0% |
| 3-HBB(F,F)—F | | 10.0% |
| 5-H2BB(F,F)—F | | 9.0% |
| 3-HB(F)VB-2 | | 4.0% |
| 3-HB(F)VB-3 | | 4.0% |

$T_{NI}$ = 91.2 (° C.)
η = 24.9 (mPa · s)
Δn = 0.125
Δε = 4.3
$V_{th}$ = 2.39 (V)

USE EXAMPLE 24

| | | |
|---|---|---|
| 3-HH4B(2F,3F)—O2 | (No. 94) | 8.0% |
| 3-HH3OB(2F,3F)B(2F,3F)-5 | (No. 237) | 4.0% |
| 3-HHB(F,F)—F | | 9.0% |
| 3-H2HB(F,F)—F | | 8.0% |
| 4-H2HB(F,F)—F | | 8.0% |

-continued

| | |
|---|---|
| 3-HBB(F,F)—F | 21.0% |
| 5-HBB(F,)—F | 20.0% |
| 3-H2BB(F,F)—F | 10.0% |
| 5-HHBB(F,F)—F | 3.0% |
| 5-HHEBB—F | 2.0% |
| 3-HH2BB(F,F)—F | 3.0% |
| 1O1-HBBH-4 | 4.0% |

$T_{NI}$ = 95.6 (° C.)
η = 39.8 (mPa · s)
Δn = 0.116
Δϵ = 8.4
$V_{th}$ = 1.82 (V)

USE EXAMPLE 25

| | | |
|---|---|---|
| 3-HH4B(2F,3F)—O2 | (No. 94) | 7.0% |
| 5-HB—F | | 12.0% |
| 6-HB—F | | 9.0% |
| 7-HB—F | | 5.0% |
| 2-HHB—OCF3 | | 7.0% |
| 3-HHB—OCF3 | | 7.0% |
| 4-HHB—OCF3 | | 7.0% |
| 3-HH2B—OCF3 | | 4.0% |
| 5-HH2B—OCF3 | | 4.0% |
| 3-HHB(F,F)—OCF3 | | 5.0% |
| 3-HBB(F)—F | | 10.0% |
| 5-HBB(F)—F | | 10.0% |
| 3-HH2B(F)—F | | 3.0% |
| 3-HB(F)BH-3 | | 3.0% |
| 5-HBBH-3 | | 3.0% |
| 3-HHB(F,F)—OCF2H | | 4.0% |

$T_{NI}$ = 85.5 (° C.)
η = 18.0 (mPa · s)
Δn = 0.094
Δϵ = 4.1
$V_{th}$ = 2.45 (V)

USE EXAMPLE 26

| | | |
|---|---|---|
| 5-H4HB(2F,3F)-3 | (No. 20) | 5.0% |
| 5-H4HB(2F,3F)—O2 | (No. 23) | 5.0% |
| 5-H4HB(F,F)—F | | 7.0% |
| 5-H4HB—OCF3 | | 5.0% |
| 3-H4HB(F,F)—CF3 | | 8.0% |
| 5-H4HB(F,F)—CF3 | | 10.0% |
| 3-HB—CL | | 6.0% |
| 5-HB—CL | | 4.0% |
| 2-H2BB(F)—F | | 5.0% |
| 3-H2BB(F)—F | | 10.0% |
| 5-HVHB(F,F)—F | | 5.0% |
| 3-HHB—OCF3 | | 5.0% |
| 3-H2HB—OCF3 | | 5.0% |
| V—HHB(F)—F | | 5.0% |
| 3-HHB(F)—F | | 5.0% |
| 5-HHEB—OCF3 | | 2.0% |
| 3-HBEB(F,F)—F | | 5.0% |
| 5-HH—V2F | | 3.0% |

$T_{NI}$ = 68.2 (° C.)
η = 27.6 (mPa · s)
Δn = 0.094
Δϵ = 8.0
$V_{th}$ = 1.78 (V)

USE EXAMPLE 27

| | | |
|---|---|---|
| 5-H4HB(2F,3F)-3 | (No. 20) | 15.0% |
| 3-HEB—O4 | | 23.0% |
| 4-HEB—O2 | | 18.0% |
| 5-HEB—O1 | | 18.0% |
| 3-HEB—O2 | | 14.0% |
| 5-HEB—O2 | | 12.0% |

$T_{NI}$ = 77.0 (° C.)
Δn = 0.087
Δϵ = −1.5

USE EXAMPLE 28

| | | |
|---|---|---|
| 5-H4HB(2F,3F)-3 | (No. 20) | 5.0% |
| 3-HH4B(2F,3F)B(2F,3F)—O2 | (No. 238) | 15.0% |
| 3-HB—O2 | | 10.0% |
| 3-HB—O4 | | 10.0% |
| 3-HH-4 | | 2.0% |
| 5-HH-2 | | 3.0% |
| 3-HEB—O4 | | 15.0% |
| 4-HEB—O2 | | 12.0% |
| 5-HEB—O1 | | 12.0% |
| 3-HEB—O2 | | 9.0% |
| 5-HEB—O2 | | 7.0% |

$T_{NI}$ = 81.9 (° C.)
Δn = 0.090
Δϵ = −2.6

USE EXAMPLE 29

| | | |
|---|---|---|
| 3-HH4B(2F,3F)—O2 | (No. 94) | 15.0% |
| 3-HB—O2 | | 15.0% |
| 3-HB—O4 | | 10.0% |
| 3-HEB—O4 | | 10.0% |
| 4-HEB—O2 | | 7.0% |
| 5-HEB—O1 | | 7.0% |
| 3-HEB—O2 | | 6.0% |
| 5-HEB—O2 | | 5.0% |
| 3-HB(2F,3F)—O2 | | 7.0% |
| 5-HHB(2F,3F)—O2 | | 5.0% |
| 5-HBB(2F,3F)-2 | | 5.0% |
| 5-HBB(2F,3F)—O2 | | 4.0% |
| 5-BB(2F,3F)B-3 | | 4.0% |

$T_{NI}$ = 77.2 (° C.)
Δn = 0.105
Δϵ = −3.1

USE EXAMPLE 30

| | | |
|---|---|---|
| 5-H4HB(2F,3F)-3 | (No. 20) | 15.0% |
| 5-H4HB(2F,3F)—O2 | (No. 23) | 10.0% |
| 3-HH4B(2F,3F)—O2 | (No. 94) | 15.0% |
| 3-HH4B(2F,3F)B(2F,3F)—O2 | (No. 238) | 5.0% |
| 3-H4B(2F,3F)—O2 | (No. 4) | 5.0% |
| 3-HB(2F,3F)—O2 | | 20.0% |
| 5-HHB(2F,3F)—O2 | | 10.0% |
| 5-HHB(2F,3F)-1O1 | | 5.0% |
| 5-HBB(2F,3F)-2 | | 10.0% |
| 5-HBB(2F,3F)-1O1 | | 5.0% |

USE EXAMPLE 31

| | | |
|---|---|---|
| 5-H4HB(2F,3F)—O2 | (No. 23) | 10.0% |
| 3-HH4B(2F,3F)—O2 | (No. 94) | 10.0% |
| 3-H4B(2F,3F)B(2F,3F)—O3 | (No. 77) | 10.0% |
| 5-HH4HB(2F,3F)—O2 | (No. 220) | 5.0% |
| 2-HHB(F)—F | | 2.0% |
| 3-HHB(F)—F | | 2.0% |
| 5-HHB(F)—F | | 2.0% |
| 2-HBB(F)—F | | 6.0% |
| 3-HBB(F)—F | | 6.0% |
| 5-HBB(F)—F | | 10.0% |
| 2-H2BB(F)—F | | 9.0% |
| 3-H2BB(F)—F | | 9.0% |
| 3-HBB(F,F)—F | | 14.0% |
| 1O1-HBBH-4 | | 5.0% |

USE EXAMPLE 32

| | | |
|---|---|---|
| 3-H4B(2F,3F)—O2 | (No. 4) | 7.0% |
| 3-HH3OB(2F,3F)-3 | (No. 91) | 4.0% |
| 5-HH4HB(2F,3F)—O2 | (No. 220) | 3.0% |
| 5-HB—CL | | 12.0% |
| 3-HH-4 | | 3.0% |
| 3-HB—O2 | | 17.0% |
| 3-H2HB(F,F)—F | | 4.0% |
| 3-HHB(F,F)—F | | 8.0% |
| 3-HBB(F,F)—F | | 6.0% |
| 2-HHB(F)—F | | 5.0% |
| 3-HHB(F)—F | | 5.0% |
| 5-HHB(F)—F | | 5.0% |
| 2-H2HB(F)—F | | 2.0% |
| 3-H2HB(F)—F | | 1.0% |
| 5-H2HB(F)—F | | 2.0% |
| 3-HHBB(F,F)—F | | 4.0% |
| 3-HBCF2OB—OCF3 | | 4.0% |
| 5-HBCF2OB(F,F)—CF3 | | 4.0% |
| 3-HHB—O1 | | 4.0% |

USE EXAMPLE 33

| | | |
|---|---|---|
| 3-H4B(2,3F)—O2 | (No. 4) | 5.0% |
| 3-HH3OB(2F,3F)-3 | (No. 91) | 8.0% |
| 1V2-BEB(F,F)—C | | 6.0% |
| 3-HB—C | | 23.0% |
| 2-BTB-1 | | 10.0% |
| 5-HH—VFF | | 20.0% |
| 1-BHH—VFF | | 8.0% |
| 1-BHH-2VFF | | 3.0% |
| 3-H2BTB-2 | | 5.0% |
| 3-H2BTB-3 | | 4.0% |
| 3-H2BTB-4 | | 4.0% |
| 3-HHB-1 | | 4.0% |

USE EXAMPLE 34

| | | |
|---|---|---|
| 5-H3OB(2F,3F)—O2 | (No. 6) | 5.0% |
| 5-H4HB(2F,3F)—O2 | (No. 23) | 15.0% |
| 3-H4B(2F,3F)B(2F,3F)—O3 | (No. 77) | 5.0% |
| 2-HB—C | | 5.0% |
| 3-HB—C | | 17.0% |
| 3-HB—O2 | | 5.0% |
| 2-BTB-1 | | 3.0% |
| 3-HHB—F | | 4.0% |
| 3-HHB—O1 | | 5.0% |

-continued

| | |
|---|---|
| 3-HHEB—F | 4.0% |
| 5-HHEB—F | 4.0% |
| 2-HHB(F)—F | 7.0% |
| 3-HHB(F)—F | 7.0% |
| 5-HHB(F)—F | 7.0% |
| 3-HHB(F,F)—F | 5.0% |

As will be understood from the Examples described above, the compounds of the present invention, that is, any two to four rings compounds having butylene group or propylenoxy group, and 2,3-difluorophenyl group in the skeleton structure at the same time have the following characteristics:

1) The compounds are wide in temperature range of exhibiting a liquid crystal phase, and are extremely high in capability of developing nematic phase.
2) Improvement in response speed in IPS mode is noticed with the compounds, since the compounds have a negative and large $\Delta\epsilon$.
3) A low viscosity, low threshold voltage, and improvement in response speed are noticed with the compounds.
4) Separation of crystals or development of smectic phase is not observed with the compounds even at very low temperatures, and stabilized nematic liquid crystal compositions can be produced from the compounds.

INDUSTRIAL APPLICABILITY

Compounds of the present invention exhibit the characteristics described in 1) to 4) above, are stable against outside environment, and can provide novel liquid crystal compositions and liquid crystal display devices by which realization of expansion of temperature range of use, driving at a low voltage, and a high speed response is possible.

What is claimed is:

1. A liquid crystalline compound expressed by the general formula (1)

(1)

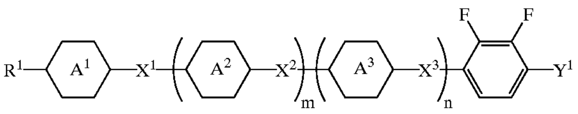

wherein $R^1$ represents an alkyl group having 1 to 15 carbon atoms in which alkyl group not-adjacent any methylene group may be replaced by oxygen atom or vinylene group, and any hydrogen atom in the alkyl group may be replaced by fluorine atom; ring $A^1$, ring $A^2$, and ring $A^3$ independently represent trans-1,4-cyclohexylene group, trans-1,4-silacyclohexylene group, pyrimidine-2,5-diyl group, pyridine-2,5-diyl group, 1,3-dioxane-2,5-diyl group, tetrahydropyran-2,5-diyl group, 1,3-dithian-2,5-diyl group, or tetrahydrothiopyran-2,5-diyl group, or 1,4-phenylene group in which one or more hydrogen atoms on the six-membered ring may be replaced by a fluorine atom; $X^1$, $X^2$, and $X^3$ independently represent —$(CH_2)_4$—, —$(CH_2)_3O$—, —$O(CH_2)_3$—, or single bond, provided that one of $X^1$, $X^2$, and $X^3$ represents —$(CH_2)_4$—, —$(CH_2)_3O$—, or —$O(CH_2)_3$ —, and the others represent single bonds; $Y^1$ represents hydrogen atom or an alkyl group having 1 to 15 carbon atoms in which alkyl group not-adjacent any methylene group may be replaced by oxygen atom or vinylene group; m and n are independently 0 or 1, provided that when both m and n are 0, and ring $A^1$ represents trans-1,4-cyclohexylene group, then $X^1$ represents $—(CH_2)_4—$, that when m is 1, n is 0, and both ring $A^1$ and ring $A^2$ represent trans-1,4-cyclohexylene group, then $X^2$ represents single bond, and that when m is 0, n is 1, and both ring $A^1$ and ring $A^3$ represent trans-1,4-cyclohexylene group, then $X^3$ represents single bond; and any atom which constitutes this compound may be replaced by its isotope.

2. The liquid crystalline compound according to claim 1 wherein ring $A^1$ and ring $A^2$ independently represent trans-1,4-cyclohexylene group, or 1,4-phenylene group in which one or more hydrogen atoms on the six-membered ring may be replaced by fluorine atom; $X^1$ represents $—(CH_2)_4—$ or $—(CH_2)_3O—$; $X^2$ represents single bond; and m is 1 and n is 0 in the general formula (1).

3. The liquid crystalline compound according to claim 1 wherein ring $A^1$ and ring $A^2$ independently represent trans-1,4-cyclohexylene group, or 1,4-phenylene group in which one or more hydrogen atoms on the six-membered ring may be replaced by fluorine atom; $X^2$ represents $—(CH_2)_4—$ or $—(CH_2)_3O—$; $X^1$ represents single bond; and m is 1 and n is 0 in the general formula (1).

4. The liquid crystalline compound according to claim 1 wherein ring $A^1$, ring $A^2$, and ring $A^3$ independently represent trans-1,4-cyclohexylene group, or 1,4-phenylene group in which one or more hydrogen atoms on the six-membered ring may be replaced by fluorine atom; $X^1$ represent $—(CH_2)_4—$ or $—(CH_2)_3O—$; either $X^2$ and $X^3$ represent single bond; and m is 1 and n is 1 in the general formula (1).

5. The liquid crystalline compound according to claim 1 wherein ring $A^1$, ring $A^2$, and ring $A^3$ independently represent trans-1,4-cyclohexylene group, or 1,4-phenylene group in which one or more hydrogen atoms on the six-membered ring may be replaced by fluorine atom; $X^2$ represents $—(CH_2)_4—$ or $—(CH_2)_3O—$; either $X^1$ and $X^3$ represent single bond; and m is 1 and n is 1 in the general formula (1).

6. The liquid crystalline compound according to claim 1 wherein ring $A^1$, ring $A^2$, and ring $A^3$ independently represent trans-1,4-cyclohexylene group, or 1,4-phenylene group in which one or more hydrogen atoms on the six-membered ring may be replaced by fluorine atom; $X^3$ represents $—(CH_2)_4—$ or $—(CH_2)_3O—$; either $X^1$ and $X^2$ represent single bond; and m is 1 and n is 1 in the general formula (1).

7. The liquid crystalline compound according to claim 1 wherein ring $A^1$ represents 1,4-phenylene group in which one or more hydrogen atoms on the six-membered ring may be replaced by fluorine atom; $X^1$ represents $—(CH_2)_4—$ or $—(CH_2)_3O—$; and each of m and n is 0 in the general formula (1).

8. A liquid crystal composition comprising, as a first component, at least one liquid crystalline compound defined in any one of claims 1–7, and comprising, as a second component, at least one compound selected from the group consisting of the compounds expressed by any one of the general formulas (2), (3), and (4)

(2)

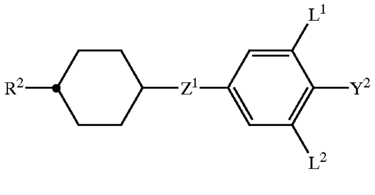

-continued (3)

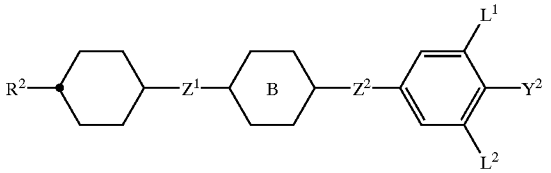

(4)

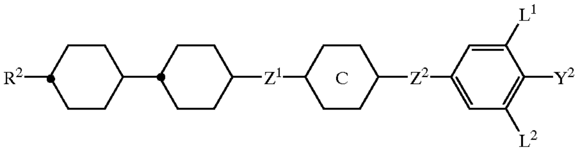

wherein $R^2$ represents an alkyl group having 1 to 10 carbon atoms in which alkyl group not-adjacent any methylene group may be replaced by oxygen atom or vinylene group; and any hydrogen atom in the alkyl group may be replaced by fluorine atom; $Y^2$ represents fluorine atom, chlorine atom, $—OCF_3$, $—OCF_2H$, $—CF_3$, $—CF_2H$, $—CFH_2$, $—OCF_2CF_2H$, or $—OCF_2CFHCF_3$; $L^1$ and $L^2$ independently represent hydrogen atom or fluorine atom; $Z^1$ and $Z^2$ independently represent 1,2-ethylene group, vinylene group, 1,4-butylene group, —COO—, $—CF_2O—$, $—OCF_2—$, or single bond; ring B represents trans-1,4-cyclohexylene group or 1,3-dioxane-2,5-diyl group, or 1,4-phenylene group in which hydrogen atom may be replaced by fluorine atom; ring C represents trans-1,4-cyclohexylene group, or 1,4-phenylene group in which hydrogen atom may be replaced by fluorine atom; and each atom which constitutes those compounds may be replaced by its isotope.

9. A liquid crystal composition comprising, as a first component, at least one liquid crystalline compound defined in any one of claims 1–7, and comprising, as a second component, at least one compound selected from the group consisting of the compounds expressed by the general formula (5) or (6)

(5)

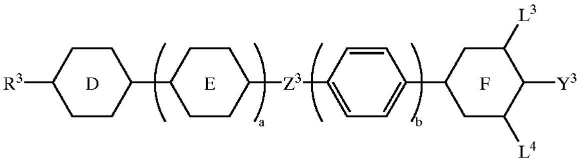

(6)

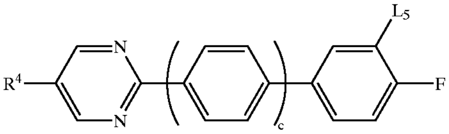

wherein $R^3$ and $R^4$ independently represent an alkyl group having 1 to 10 carbon atoms in which alkyl group not-adjacent any methylene group may be replaced by oxygen atom or vinylene group, and any hydrogen atom in the alkyl group may be replaced by fluorine atom; $Y^3$ represents —CN or —C≡C—CN; ring D represents trans-1,4-cyclohexylene group, 1,4-phenylene group, pyrimidine-2,5-diyl group, or 1,3-dioxane-2,5-diyl group; ring E represents trans-1,4-cyclohexylene group or pyrimidine-2,5-diyl group, or 1,4-phenylene group in which hydrogen atom may be replaced by fluorine atom; ring F represents trans-1,4-cyclohexylene group or 1,4-phenylene group; $Z^3$ represents 1,2-ethylene group, —COO—, or single bond; $L^3$, $L^4$, and $L^5$ independently represent hydrogen atom or fluorine atom; a, b, and c are independently 0 or 1; and each atom which constitutes those compounds may be replaced by its isotope.

10. A liquid crystal composition comprising, as a first component, at least one liquid crystalline compound defined in any one of claims 1–7, and comprising, as a second component, at least one compound selected from the group consisting of the compounds expressed by any one of the general formulas (10), (11), and (12)

(10)

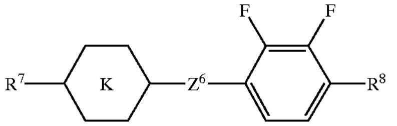

(11)

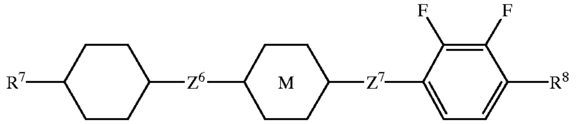

(12)

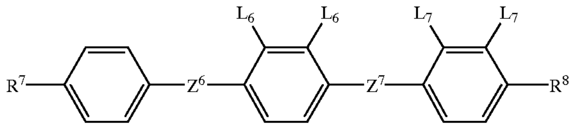

wherein $R^7$ and $R^8$ independently represent an alkyl group having 1 to 10 carbon atoms in which alkyl group not-adjacent any methylene group may be replaced by oxygen atom or vinylene group, and any hydrogen atom in the alkyl group may be replaced by fluorine atom; ring K and ring M independently represent trans-1,4-cyclohexylene or 1,4-phenylene; $L^6$ and $L^7$ independently represent hydrogen atom or fluorine atom, but in no case simultaneously represent $L^6$ and $L^7$ hydrogen atom; $Z^6$ and $Z^7$ independently represent —$CH_2CH_2$—, —COO—, or single bond; and each atom which constitutes those compounds may be replaced by its isotope.

11. A liquid crystal composition comprising at least two components, at least one of which is a liquid crystalline compound expressed by the general formula (1)

(1)

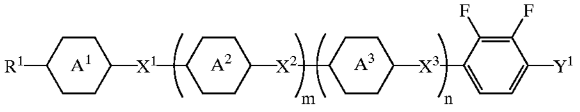

wherein $R^1$ represents an alkyl group having 1 to 15 carbon atoms in which alkyl group not-adjacent any methylene group may be replaced by oxygen atom or vinylene group, and any hydrogen atom in the alkyl group may be replaced by fluorine atom; ring $A^1$, ring $A^2$, and ring $A^3$ independently represent trans-1,4-cyclohexylene group, trans-1,4-silacyclohexylene group, pyrimidine-2,5-diyl group, pyridine-2,5-diyl group, 1,3-dioxane-2,5-diyl group, tetrahydropyran-2,5-diyl group, 1,3-dithian-2,5-diyl group, or tetrahydrothiopyran-2,5-diyl group, or 1,4-phenylene group in which one or more hydrogen atoms on the six-membered ring may be replaced by a fluorine atom; $X^1$, $X^2$, and $X^3$ independently represent —$(CH_2)_4$—, —$(CH_2)_3O$—, —$O(CH_2)_3$—, or single bond, provided that one of $X^1$, $X^2$, and $X^3$ represents —$(CH_2)_4$—, —$(CH_2)_3O$—, or —$O(CH_2)_3$—, and the others represent single bonds; $Y^1$ represents hydrogen atom or an alkyl group having 1 to 15 carbon atoms in which alkyl group not-adjacent any methylene group may be replaced by oxygen atom or vinylene group; m and n are independently 0 or 1, provided that when both m and n are 0, and ring $A^1$ represents trans-1,4-cyclohexylene group, then $X^1$ represents —$(CH_2)_4$—, that when m is 1, n is 0, and both ring $A^1$ and ring $A^2$ represent trans-1,4-cyclohexylene group, then $X^2$ represents single bond, and that when m is 0, n is 1, and both ring $A^1$ and ring $A^3$ represent trans-1,4-cyclohexylene group, then $X^3$ represents single bond; and any atom which constitutes this compound may be replaced by its isotope.

12. A liquid crystal composition comprising at least one optically active compound in addition to the liquid crystal composition defined in claim 11.

13. A liquid crystal display device fabricated by using the liquid crystal composition defined in claim 11.

14. A liquid crystal composition comprising, as a first component, at least one liquid crystalline compound defined in any one of claims 1–7, comprising, as a second component, at least one compound selected from the group consisting of the compounds expressed by any one of the general formulas (2), (3), and (4), and comprising, as a third component, at least one compound selected from the group consisting of the compounds expressed by any one of the general formulas (7), (8), and (9)

(2)

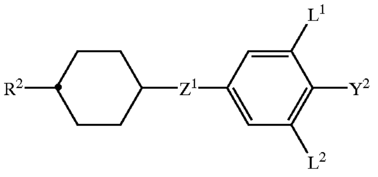

(3)

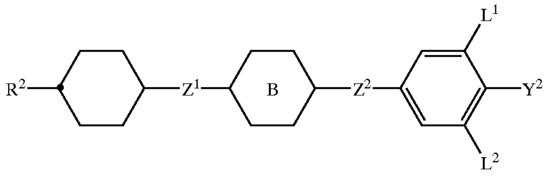

(4)

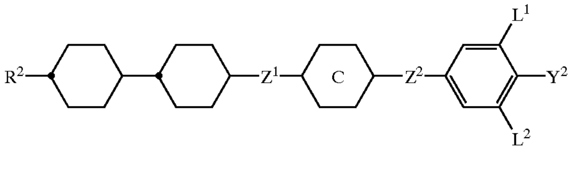

wherein $R^2$ represents an alkyl group having 1 to 10 carbon atoms in which alkyl group not-adjacent any methylene group may be replaced by oxygen atom or vinylene group; and any hydrogen atom in the alkyl group may be replaced by fluorine atom; $Y^2$ represents fluorine atom, chlorine atom, —$OCF_3$, —$OCF_2H$, —$CF_3$, —$CF_2H$, —$CFH_2$, —$OCF_2CF_2H$, or —$OCF_2CFHCF_3$; $L^1$ and $L^2$ independently represent hydrogen atom or fluorine atom; $Z^1$ and $Z^2$ independently represent 1,2-ethylene group, vinylene group, 1,4-butylene group, —COO—, —$CF_2O$—, —$OCF_2$—, or single bond; ring B represents trans-1,4-cyclohexylene group or 1,3-dioxane-2,5-diyl group, or 1,4-phenylene group in which hydrogen atom may be replaced by fluorine atom; ring C represents trans-1,4-cyclohexylene group, or 1,4-phenylene group in which hydrogen atom may be replaced by fluorine atom; and each atom which constitutes those compounds may be replaced by its isotope, (7)

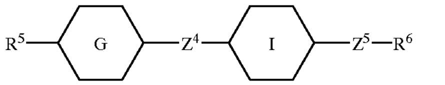

(8)

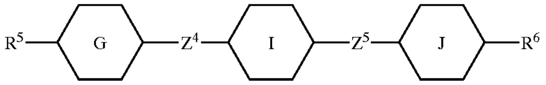

(9)

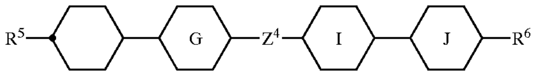

wherein $R^5$ and $R^6$ independently represent an alkyl group having 1 to 10 carbon atoms in which alkyl group not-adjacent any methylene group may be replaced by oxygen atom or vinylene group, and any hydrogen atom in the alkyl group may be replaced by fluorine atom; ring G, ring I, and ring J independently represent trans-1,4-cyclohexylene group or pyrimidine-2,5-diyl group, or 1,4-phenylene group in which one hydrogen atom may be replaced by fluorine atom; $Z^4$ and $Z^5$ independently represent 1,2-ethylene group, vinylene group, —COO—, —C≡C—, or single bond; and each atom which constitutes those compounds may be replaced by its isotope.

15. A liquid crystal composition comprising, as a first component, at least one liquid crystalline compound defined in any one of claims 1–7, comprising, as a second component, at least one compound selected from the group consisting of the compounds expressed by any one of the general formulas (7), (8), and (9), and comprising, as a third component, at least one compound selected from the group consisting of the compounds expressed by any one of the general formulas (10), (11), and (12)

(7)

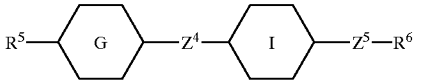

(8)

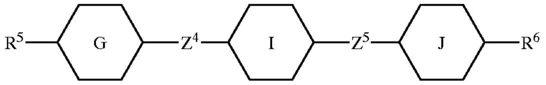

(9)

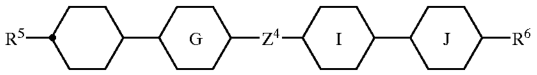

wherein $R^5$ and $R^6$ independently represent an alkyl group having 1 to 10 carbon atoms in which alkyl group not-adjacent any methylene group may be replaced by oxygen atom or vinylene group, and any hydrogen atom in the alkyl group may be replaced by fluorine atom; ring G, ring I, and ring J independently represent trans-1,4-cyclohexylene group or pyrimidine-2,5-diyl group, or 1,4-phenylene group in which one hydrogen atom may be replaced by fluorine atom; $Z^4$ and $Z^5$ independently represent 1,2-ethylene group, vinylene group, —COO—, —C≡C—, or single bond; and each atom which constitutes those compounds may be replaced by its isotope, (10)

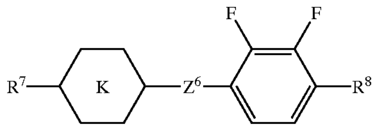

(11)

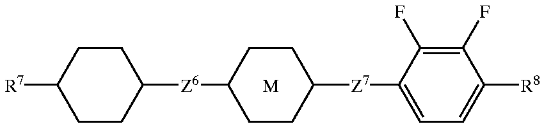

(12)

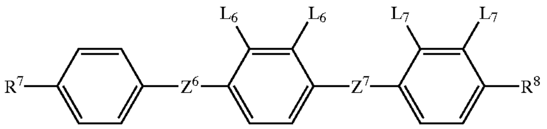

wherein $R^7$ and $R^8$ independently represent an alkyl group having 1 to 10 carbon atoms in which alkyl group not-adjacent any methylene group may be replaced by oxygen atom or vinylene group, and any hydrogen atom in the alkyl group may be replaced by fluorine atom; ring K and ring M independently represent trans-1,4-cyclohexylene or 1,4-phenylene; $L^6$ and $L^7$ independently represent hydrogen atom or fluorine atom, but in no case simultaneously represent $L^6$ and $L^7$ hydrogen atom; $Z^6$ and $Z^7$ independently represent $—CH_2CH_2—$, —COO—, or single bond; and each atom which constitutes those compounds may be replaced by its isotope.

16. A liquid crystal composition comprising, as a first component, at least one liquid crystalline compound defined in any one of claims 1–7, comprising, as a second component, at least one compound selected from the group consisting of the compounds expressed by any one of the general formulas (2), (3), and (4), and comprising, as a third component, at least one compound selected from the group consisting of the compounds expressed by any one of the general formulas (7), (8), and (9)

(2)

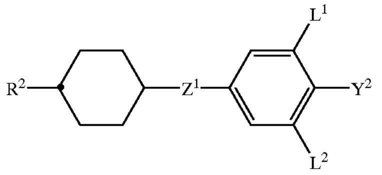

(3)

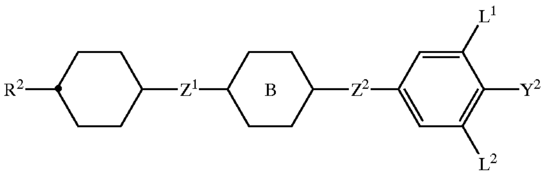

-continued (4)

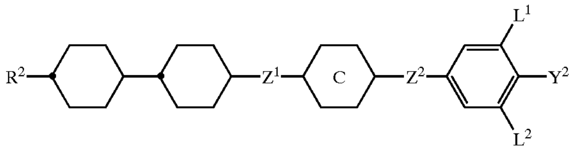

wherein $R^2$ represents an alkyl group having 1 to 10 carbon atoms in which alkyl group not-adjacent any methylene group may be replaced by oxygen atom or vinylene group; and any hydrogen atom in the alkyl group may be replaced by fluorine atom; $Y^2$ represents fluorine atom, chlorine atom, $—OCF_3$, $—OCF_2H$, $—CF_3$, $—CF_2H$, $—CFH_2$, $—OCF_2CF_2H$, or $—OCF_2CFHCF_3$; $L^1$ and $L^2$ independently represent hydrogen atom or fluorine atom; $Z^1$ and $Z^2$ independently represent 1,2-ethylene group, vinylene group, 1,4-butylene group, —COO—, $—CF_2O—$, $—OCF_2—$, or single bond; ring B represents trans-1,4-cyclohexylene group or 1,3-dioxane-2,5-diyl group, or 1,4-phenylene group in which hydrogen atom may be replaced by fluorine atom; ring C represents trans-1,4-cyclohexylene group, or 1,4-phenylene group in which hydrogen atom may be replaced by fluorine atom; and each atom which constitutes those compounds may be replaced by its isotope, (7)

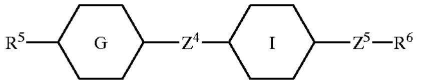

(8)

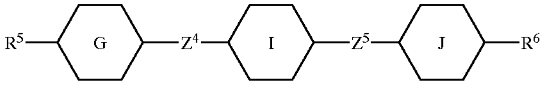

(9)

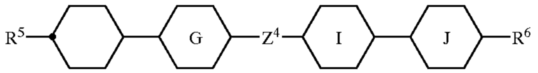

wherein $R^5$ and $R^6$ independently represent an alkyl group having 1 to 10 carbon atoms in which alkyl group not-adjacent any methylene group may be replaced by oxygen atom or vinylene group, and any hydrogen atom in the alkyl group may be replaced by fluorine atom; ring G, ring I, and ring J independently represent trans-1,4-cyclohexylene group or pyrimidine-2,5-diyl group, or 1,4-phenylene group in which one hydrogen atom may be replaced by fluorine atom; $Z^4$ and $Z^5$ independently represent 1,2-ethylene group, vinylene group, —COO—, —C≡C—, or single bond; and each atom which constitutes those compounds may be replaced by its isotope.

17. A liquid crystal composition comprising, as a first component, at least one liquid crystalline compound defined in any one of claims 1–7, comprising, as a second component, at least one compound selected from the group consisting of the compounds expressed by any one of the general formula (5) or (6), and comprising, as a third component, at least one compound selected from the group consisting of the compounds expressed by any one of the general formulas (7), (8), and (9)

(5)

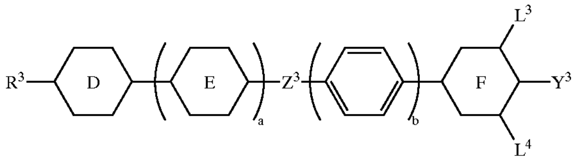

(6)

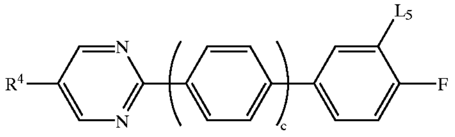

wherein $R^3$ and $R^4$ independently represent an alkyl group having 1 to 10 carbon atoms in which alkyl group not-adjacent any methylene group may be replaced by oxygen atom or vinylene group, and any hydrogen atom in the alkyl group may be replaced by fluorine atom; $Y^3$ represents —CN or —C≡C—CN; ring D represents trans-1,4-cyclohexylene group, 1,4-phenylene group, pyrimidine-2,5-diyl group, or 1,3-dioxane-2,5-diyl group; ring E represents trans-1,4-cyclohexylene group or pyrimidine-2,5-diyl group, or 1,4-phenylene group in which hydrogen atom may be replaced by fluorine atom; ring F represents trans-1,4-cyclohexylene group or 1,4-phenylene group; $Z^3$ represents 1,2-ethylene group, —COO—, or single bond; $L^3$, $L^4$, and $L^5$ independently represent hydrogen atom or fluorine atom; a, b, and c are independently 0 or 1; and each atom which constitutes those compounds may be replaced by its isotope, (7)

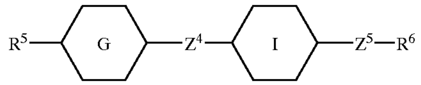

(8)

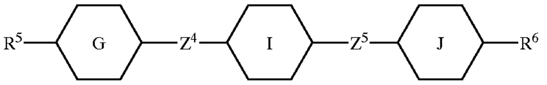

(9)

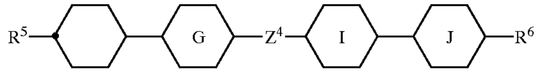

wherein $R^5$ and $R^6$ independently represent an alkyl group having 1 to 10 carbon atoms in which alkyl group not-adjacent any methylene group may be replaced by oxygen atom or vinylene group, and any hydrogen atom in the alkyl group may be replaced by fluorine atom; ring G, ring I, and ring J independently represent trans-1,4-cyclohexylene group or pyrimidine-2,5-diyl group, or 1,4-phenylene group in which one hydrogen atom may be replaced by fluorine atom; $Z^4$ and $Z^5$ independently represent 1,2-ethylene group, vinylene group, —COO—, —C≡C—, or single bond; and each atom which constitutes those compounds may be replaced by its isotope.

18. A liquid crystal composition comprising, as a first component, at least one liquid crystalline compound defined in any one of claims 1–7, comprising, as a second component, at least one compound selected from the group consisting of the compounds expressed by any one of the general formulas (2), (3), and (4), comprising, as a third component, at least one compound selected from the group consisting of the compounds expressed by any one of the general formula (5) or (6), and comprising, as a fourth component, at least one compound selected from the group consisting of the compounds expressed by any one of the general formulas (7), (8), and (9)

(2)

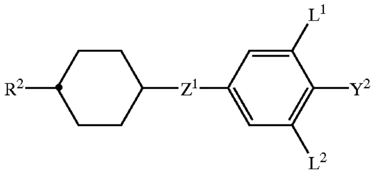

(3)

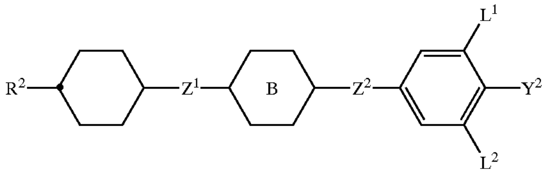

(4)

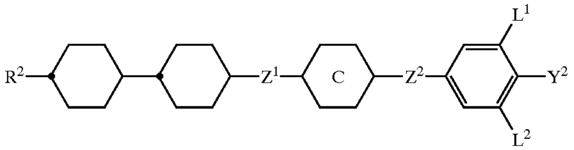

wherein $R^2$ represents an alkyl group having 1 to 10 carbon atoms in which alkyl group not-adjacent any methylene group may be replaced by oxygen atom or vinylene group; and any hydrogen atom in the alkyl group may be replaced by fluorine atom; $Y^2$ represents fluorine atom, chlorine atom, $—OCF_3$, $—OCF_2H$, $—CF_3$, $—CF_2H$, $—CFH_2$, $—OCF_2CF_2H$, or $—OCF_2CFHCF_3$; $L^1$ and $L^2$ independently represent hydrogen atom or fluorine atom; $Z^1$ and $Z^2$ independently represent 1,2-ethylene group, vinylene group, 1,4-butylene group, —COO—, $—CF_2O—$, $—OCF_2—$, or single bond; ring B represents trans-1,4-cyclohexylene group or 1,3-dioxane-2,5-diyl group, or 1,4-phenylene group in which hydrogen atom may be replaced by fluorine atom; ring C represents trans-1,4-cyclohexylene group, or 1,4-phenylene group in which hydrogen atom may be replaced by fluorine atom; and each atom which constitutes those compounds may be replaced by its isotope, (5)

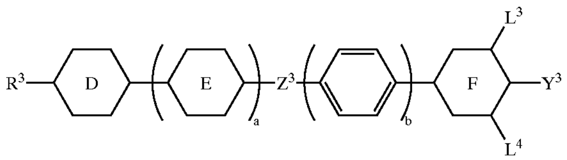

-continued (6)

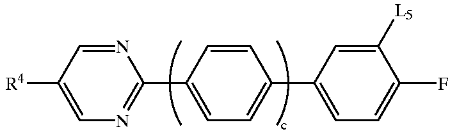

wherein $R^3$ and $R^4$ independently represent an alkyl group having 1 to 10 carbon atoms in which alkyl group not-adjacent any methylene group may be replaced by oxygen atom or vinylene group, and any hydrogen atom in the alkyl group may be replaced by fluorine atom; $Y^3$ represents —CN or —C≡C—CN; ring D represents trans-1,4-cyclohexylene group, 1,4-phenylene group, pyrimidine-2,5-diyl group, or 1,3-dioxane-2,5-diyl group; ring E represents trans-1,4-cyclohexylene group or pyrimidine-2,5-diyl group, or 1,4-phenylene group in which hydrogen atom may be replaced by fluorine atom; ring F represents trans-1,4-cyclohexylene group or 1,4-phenylene group; $Z^3$ represents 1,2-ethylene group, —COO—, or single bond; $L^3$, $L^4$, and $L^5$ independently represent hydrogen atom or fluorine atom; a, b, and c are independently 0 or 1; and each atom which constitutes those compounds may be replaced by its isotope, (7)

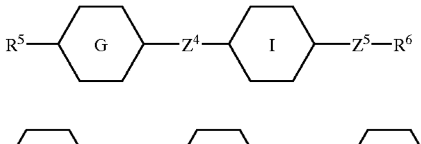

(8)

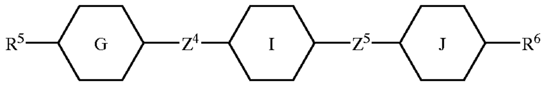

(9)

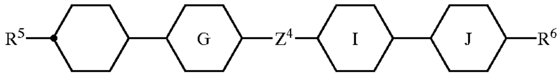

wherein $R^5$ and $R^6$ independently represent an alkyl group having 1 to 10 carbon atoms in which alkyl group not-adjacent any methylene group may be replaced by oxygen atom or vinylene group, and any hydrogen atom in the alkyl group may be replaced by fluorine atom; ring G, ring I, and ring J independently represent trans-1,4-cyclohexylene group or pyrimidine-2,5-diyl group, or 1,4-phenylene group in which one hydrogen atom may be replaced by fluorine atom; $Z^4$ and $Z^5$ independently represent 1,2-ethylene group, vinylene group, —COO—, —C≡C—, or single bond; and each atom which constitutes those compounds may be replaced by its isotope.

* * * * *